(12) United States Patent
Noda et al.

(10) Patent No.: US 8,183,431 B2
(45) Date of Patent: May 22, 2012

(54) ABSORBENT BODY, MULTILAYER ABSORBENT BODY AND ABSORBENT ARTICLE

(75) Inventors: Yuki Noda, Kagawa (JP); Hideyuki Ishikawa, Kagawa (JP); Satoshi Mizutani, Kagawa (JP); Koichiro Tani, Kagawa (JP); Akihiro Kimura, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 986 days.

(21) Appl. No.: 11/762,349

(22) Filed: Jun. 13, 2007

(65) Prior Publication Data
US 2007/0299416 A1 Dec. 27, 2007

(30) Foreign Application Priority Data

Jun. 23, 2006 (JP) ................................. 2006-174505
Sep. 29, 2006 (JP) ................................. 2006-270112

(51) Int. Cl.
*A61F 13/15* (2006.01)
*A61F 13/20* (2006.01)
(52) U.S. Cl. ...................................... 604/384; 604/380
(58) Field of Classification Search .................. 604/358, 604/378, 380, 384; 428/157, 173, 131, 156, 428/167
See application file for complete search history.

(56) References Cited

U.S. PATENT DOCUMENTS

| | | | |
|---|---|---|---|
| 3,458,905 A | 8/1969 | Dodson, Jr. et al. | |
| 3,485,706 A | 12/1969 | Evans | |
| 3,486,168 A | 12/1969 | Evans et al. | |
| 3,766,922 A | * 10/1973 | Krusko | ........................ 604/374 |
| 4,016,317 A | 4/1977 | Kalwaites | |
| 4,016,319 A | 4/1977 | Marshall | |
| 4,038,452 A | 7/1977 | Kobayashi et al. | |
| 4,186,463 A | * 2/1980 | Marshall | ........................ 19/304 |
| 4,190,695 A | 2/1980 | Niederhauser | |
| 4,379,799 A | 4/1983 | Holmes et al. | |

(Continued)

FOREIGN PATENT DOCUMENTS

CN 1294904 5/2001

(Continued)

OTHER PUBLICATIONS

English translation of JP 2002-249965 A to Oka et al.*

(Continued)

*Primary Examiner* — Melanie Hand
(74) *Attorney, Agent, or Firm* — Lowe, Hauptman, Ham & Berner, LLP

(57) ABSTRACT

The present invention provides an absorbent body containing absorbent fibers in which fiber orientation is mainly adjusted, and fiber basis weight and shape are additionally adjusted. The absorbent body 110 of the present invention is an absorbent body containing absorbent fibers, a plurality of low fiber basis weight regions formed continuously in the first direction with a fiber basis weight that is less than an average fiber basis weight of the absorbent body 110, and a plurality of high fiber basis weight regions, formed along and on both sides of the low fiber basis weight regions in relation to the second direction perpendicular to the first direction, with a fiber basis weight that is greater than the average fiber basis weight of the absorbent body 110. The content of longitudinally oriented fibers in the fibers 101 making up the high fiber basis weight regions is greater than that of laterally oriented fibers, and the content of longitudinally oriented fibers in the fibers 101 making up the low fiber basis weight regions is greater than that of laterally oriented fibers.

17 Claims, 23 Drawing Sheets

U.S. PATENT DOCUMENTS

| | | | |
|---|---|---|---|
| 4,582,666 A | 4/1986 | Kenworthy et al. | |
| 4,612,226 A | 9/1986 | Kennette et al. | |
| 4,695,500 A | 9/1987 | Dyer et al. | |
| 4,735,842 A | 4/1988 | Buyofsky et al. | |
| 4,787,947 A | 11/1988 | Mays | |
| 4,835,042 A | 5/1989 | Dohzono et al. | |
| 4,840,829 A | 6/1989 | Suzuki et al. | |
| 5,607,414 A | 3/1997 | Richards et al. | |
| 5,613,962 A | 3/1997 | Kenmochi et al. | |
| 5,618,610 A | 4/1997 | Tomita et al. | |
| 5,733,625 A | 3/1998 | Tsuchiya et al. | |
| 5,897,547 A | 4/1999 | Schmitz | |
| 5,900,109 A | 5/1999 | Sanders et al. | |
| 6,039,555 A | 3/2000 | Tsuji et al. | |
| 6,096,016 A | 8/2000 | Tsuji et al. | |
| 6,395,957 B1 | 5/2002 | Chen et al. | |
| 6,451,718 B1 | 9/2002 | Yamada et al. | |
| 6,582,798 B2 | 6/2003 | Thomas | |
| 6,586,076 B1 | 7/2003 | Mizutani et al. | |
| 6,610,173 B1 | 8/2003 | Lindsay et al. | |
| 6,641,902 B1 | 11/2003 | Kobayashi et al. | |
| 6,802,932 B2 | 10/2004 | Kudo et al. | |
| 6,855,424 B1 | 2/2005 | Thomas et al. | |
| 6,867,156 B1 | 3/2005 | White et al. | |
| 6,936,333 B2 | 8/2005 | Shizuno et al. | |
| 7,507,463 B2 | 3/2009 | Noda et al. | |
| 7,553,535 B2 | 6/2009 | Noda et al. | |
| 7,662,462 B2 | 2/2010 | Noda et al. | |
| 2002/0010449 A1 | 1/2002 | Mizutani | |
| 2003/0198784 A1 | 10/2003 | Mizutani et al. | |
| 2003/0232558 A1 | 12/2003 | Moody, III et al. | |
| 2004/0204697 A1* | 10/2004 | Litvay | 604/367 |
| 2005/0177121 A1 | 8/2005 | Mizutani et al. | |
| 2008/0289157 A1 | 11/2008 | Higashinaka et al. | |

FOREIGN PATENT DOCUMENTS

| | | | |
|---|---|---|---|
| DE | 4437165 A1 | 4/1996 | |
| DE | 102005036759 A1 | 8/2006 | |
| EP | 0703308 | 3/1996 | |
| EP | 0903136 A2 | 3/1999 | |
| EP | 903136 A2 * | 3/1999 | |
| EP | 0926287 A1 | 6/1999 | |
| EP | 1090615 | 4/2001 | |
| EP | 1201213 A2 | 5/2002 | |
| EP | 1269956 | 1/2003 | |
| JP | S56-119249 A | 9/1981 | |
| JP | 02-169718 A | 6/1990 | |
| JP | 02-229255 A | 9/1990 | |
| JP | 03-137257 | 6/1991 | |
| JP | 04-100958 A | 4/1992 | |
| JP | H-04-221556 A | 8/1992 | |
| JP | 08-060509 A | 3/1996 | |
| JP | 08-216310 A | 8/1996 | |
| JP | H-08-302555 A | 11/1996 | |
| JP | 2002-030557 A | 1/2002 | |
| JP | 2002-035036 A | 2/2002 | |
| JP | 2002-136547 A | 5/2002 | |
| JP | 2002243965 | 8/2002 | |
| JP | 2002-249965 A | 9/2002 | |
| JP | 2003126147 | 5/2003 | |
| JP | 2003-291234 A | 10/2003 | |
| JP | 3587831 | 8/2004 | |
| JP | 2005-073921 A | 3/2005 | |
| WO | 2005122817 A1 | 12/2005 | |

OTHER PUBLICATIONS

JP 08-060509 A (Abstract only) to Tomita et al.*
Office Action issued to U.S. Appl. No. 11/762,421, mailed Oct. 6, 2009.
International Search Report of PCT/JP2007/061601 issued Aug. 7, 2007.
International Search Report of PCT/JP2007/060543 issued Jul. 10, 2007.
International Search Report of PCT/JP2007/061444 issued Aug. 7, 2007.
Office Action issued to U.S. Appl. No. 11/755,376 mailed Jun. 30, 2009.
International Search Report of PCT/JP2007/061445 issued Jul. 31, 2007.
Office Action issued Aug. 4, 2009, from U.S. Appl. No. 11/748,712, filed May 15, 2007.
European Search Report for Application No. EP07743982, mailed Apr. 8, 2010.
Office Action issued to U.S. Appl. No. 11/755,376, mailed Nov. 25, 2009.
Final Office Action issued to U.S. Appl. No. 11/748,712, mailed Mar. 23, 2010.
Office Action issued to CN Application No. 200780022784.6 mailed May 12, 2010.
Office Action issued to U.S. Appl. No. 11/762,421 mailed May 11, 2010.
Notice of Allowance Issued to U.S. Appl. No. 11/755,376, mailed Jun. 21, 2010.
Office Action Issued to U.S. Appl. No. 11/748,186, mailed Jun. 22, 2010.
Office Action issued to U.S. Appl. No. 12/511,115, mailed Sep. 14, 2010.
European Search Report for European Patent Application No. 07743977.6 issued Apr. 18, 2011.
European Search Report for European Patent Application No. 07743978.4 issued Apr. 18, 2011.
European Search Report for European Patent Application No. 07743979.2 issued Apr. 18, 2011.
European Search Report for European Patent Application No. 07744787.8 issued Apr. 29, 2011.
European Search Report for European Patent Application No. 07743980.0 issued Apr. 18, 2011.
European Search Report for European Patent Application No. 07743981.8 issued Apr. 18, 2011.
European Search Report for European Patent Application No. 07744921.3 issued Apr. 18, 2011.
European Search Report for European Patent Application No. 07744788.6 issued Apr. 29, 2011.
European Search Report for European Patent Application No. 07767438.0 issued Apr. 29, 2011.
Office Action issued to ID Application No. W00200804035 mailed Apr. 26, 2011.
Office Action issued to U.S. Appl. No. 11/766,867 mailed Aug. 23, 2011.
Japanese Office Action mailed Nov. 22, 2011 in corresponding Japanese Patent Application No. 2006-270111.

* cited by examiner

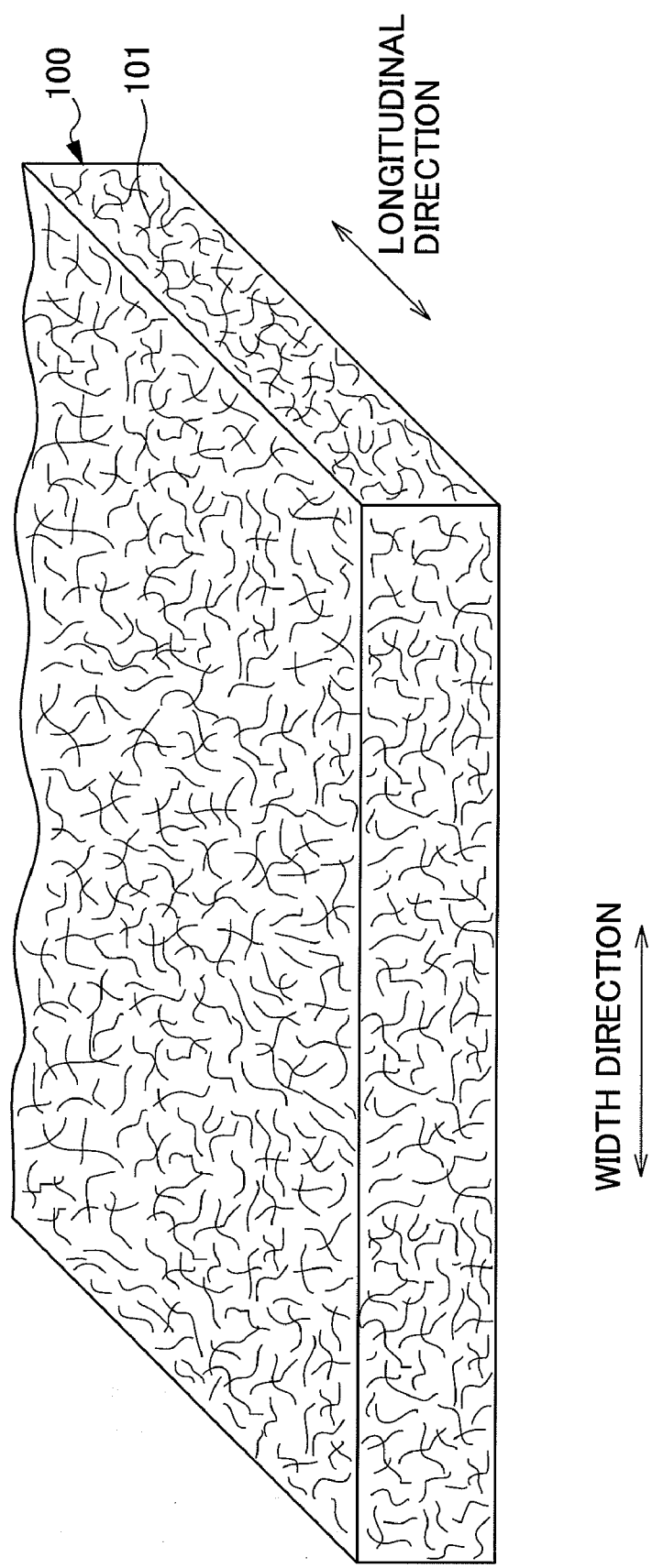

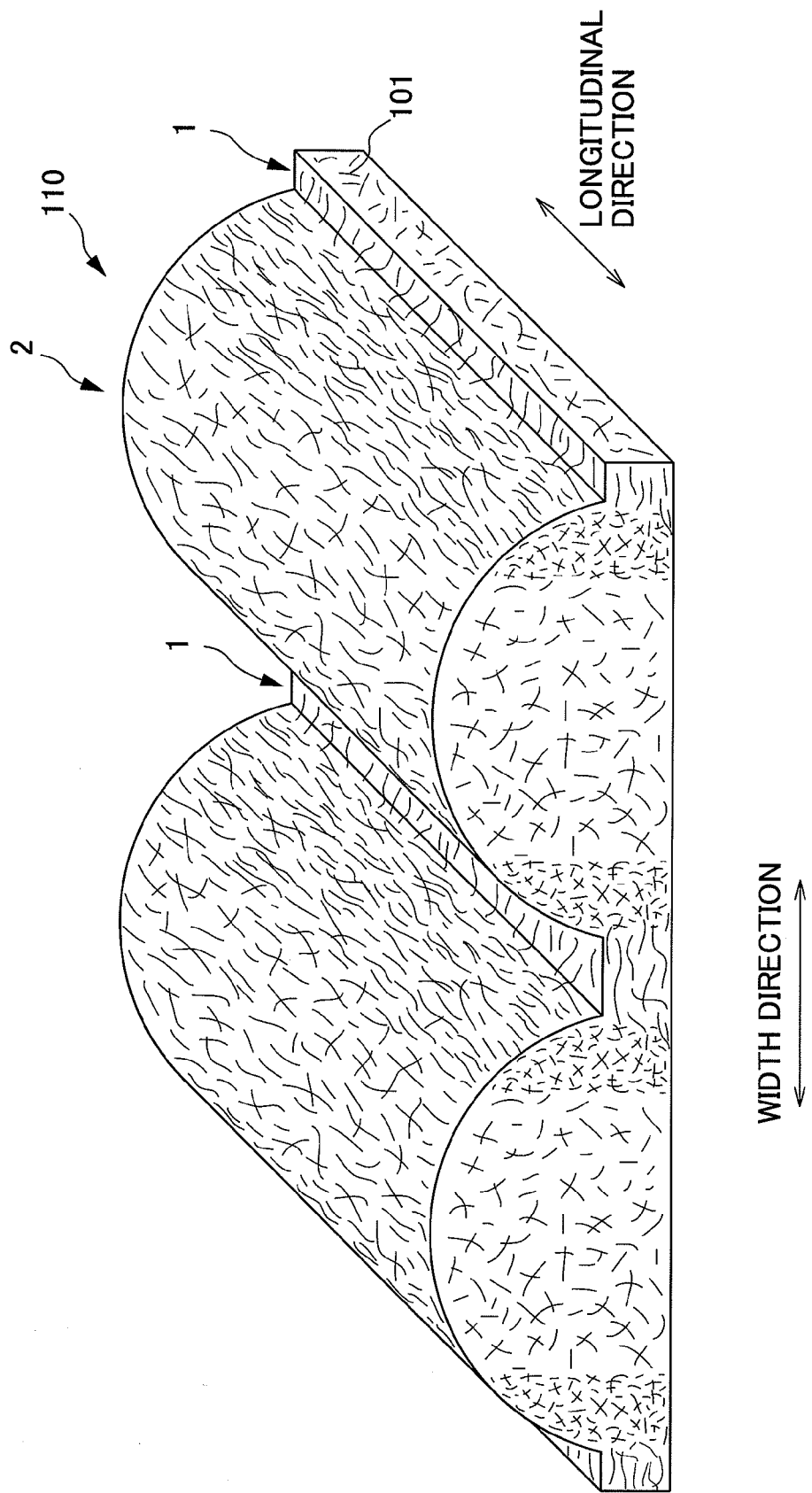

ABSORBENT BODY, MULTILAYER ABSORBENT BODY AND ABSORBENT ARTICLE

This application is based on and claims the benefit of priority from Japanese Patent Application No. 2006-174505 filed on 23 Jun. 2006 and Japanese Patent Application No. 2006-270112 filed on 29 Sep. 2006, the content of which is incorporated herein by reference.

BACKGROUND OF THE INVENTION

1. Field of the Invention

The present invention relates to an absorbent body containing absorbent fiber, and absorbent articles equipped with the absorbent body.

2. Related Art

Absorbent bodies containing absorbent fiber such as cellulose fiber have been used in wide variety of fields including sanitary materials such as diapers and sanitary napkins, cleaning products and medical supplies. Absorbent bodies are used in various different fields as described above, and it is necessary for the absorbent body to be produced so as to have characteristics and structures suitable for use in each product application.

In addition, in recent years, multilayer absorbent bodies in which nonwoven fabrics are layered in the absorbent body may be formed into shapes suitable for use in each product application in order to fulfill the intended function.

For example, oblong diapers in which embossed groove portions are formed in a backward and forward direction of the absorbent body for dispersing discharged urine, etc., are disclosed in Japanese Unexamined Patent Application publication No. 2005-73921.

The absorbent body made of pulp and high water-absorption resins in which a through hole or a non-through depressed area is formed by inserting a needle-like or conical projection is disclosed in Japanese Patent No. 3556581.

Density of the embossed groove portions formed in the absorbent body as disclosed in Japanese Unexamined Patent Application publication No. 2005-73921 may increase, thereby increasing the rigidity of the absorbent body. When diapers equipped with this kind of absorbent body come into contact with the body, voids may be left between the diapers and the body because diapers do not fit the body. This increases possibility of leakage of excretory substances giving users a foreign body sensation.

Fiber in areas other than the openings of the absorbent body disclosed in Japanese Patent No. 3556581 are oriented approximately in the same direction because uniformly layered absorbent body are only equipped with openings formed by secondary processing with needle-like projection, etc. When the fibers in the areas other than the openings are oriented approximately in the same direction as described above, menstrual blood migrated from surface sheets is absorbed almost concentrically along the oriented direction of the hydrophilic fibers while avoiding the openings in the areas other than the openings. This allows menstrual blood to reach both sides of the absorbent body easily causing side leakage if the absorbent body has an oblong shape conforming to the shape of the body.

SUMMARY OF THE INVENTION

An object of the present invention is to provide an absorbent body containing absorbent fibers in which fiber orientation is mainly adjusted, and fiber basis weight and shape are additionally adjusted.

In a first aspect of the present invention an absorbent body including an absorbent fiber, comprising a plurality of low fiber basis weight regions and a plurality of high fiber basis weight regions in which the low fiber basis weight regions formed continuously along a first direction have a fiber basis weight that is less than an average fiber basis weight of the absorbent body, the high fiber basis weight regions are formed on both sides of the low fiber basis weight regions in a second direction perpendicular to the first direction along the low fiber basis weight regions, and have a greater fiber basis weight than the average fiber basis weight of the absorbent body, a content of fibers oriented toward the first direction in the fibers which make up the high fiber basis weight regions is greater than a content of fibers oriented toward the second direction in each of the high fiber basis weight regions, and a content of fibers oriented toward the second direction in the fibers which make up the low fiber basis weight regions is greater than a content of fibers oriented toward the first direction in each of the low fiber basis weight regions.

In a second aspect of the absorbent body as described in the first aspect of the present invention, at least part of the high fiber basis weight regions are raised ridge portions raised in a thickness direction of the absorbent body, with a thickness, which is a length in the thickness direction, being greater than an average thickness of the absorbent body, and at least part of the low fiber basis weight regions are groove portions depressed in the thickness direction with a thickness that is less than the average thickness of the absorbent body.

In a third aspect of the absorbent body as described in either of the first and second aspects of the present invention, a plurality of low amount of fiber regions including at least one of a plurality of depressed portions and openings is formed in the low fiber basis weight regions.

In a fourth aspect of the absorbent body as described in the third aspect of the present invention, the thickness of side areas of the high fiber basis weight regions, which are disposed on both sides of the plurality of low amount of fiber regions, is less than the thickness of areas other than the side areas of the high fiber basis weight regions.

In a fifth aspect of the absorbent body as described in any one of the first to fourth aspects of the present invention, the absorbent body further contains an absorbent polymer.

In a sixth aspect of the absorbent body as described in the fifth aspect of the present invention, the absorbent polymer is disposed on a surface opposite to a surface on which the low fiber basis weight regions and the high fiber basis weight regions are formed.

In a seventh aspect of the absorbent body as described in either of the fifth and sixth aspects of the present invention, the absorbent polymer is disposed in the low fiber basis weight regions.

In an eighth aspect of the present invention an absorbent body containing a first absorbent body and a second absorbent body, wherein the first absorbent body is the absorbent body as described in the first to seventh aspects of the present invention, the second absorbent body is the absorbent body as described in the fifth to seventh aspects of the present invention, and the first absorbent body and the second absorbent body are layered and disposed so as for each of the surfaces on which the low fiber basis weight regions and the high fiber basis weight regions are formed face one another.

In a ninth aspect of the present invention a multilayer absorbent body containing a first fiber layer and an absorbent body containing absorbent fibers in which the absorbent body containing the absorbent fibers is layered and disposed on a first side of the first fiber layer, a plurality of groove portions formed along the first direction depressed in a thickness direction of the multilayer absorbent body in relation to a second side of the first fiber layer, and a plurality of raised ridge portions, formed adjacent to each of the groove portions, raised in the thickness direction with a fiber basis weight that is greater than that of areas which make up the base of the groove portions is formed, each of the first fiber layer and the absorbent body is layered and disposed in each of the areas which make up the base of the groove portions and the raised ridge portions, and the first fiber layer side of the absorbent body which make up each of the raised ridge portions is raised toward the same direction as the direction in which the second side of the first fiber layer is raised.

In a tenth aspect of the multilayer absorbent body as described in the ninth aspect of the present invention, a content of the fiber oriented toward the first direction in the fibers which make up the raised ridge portions is greater than a content of the fiber oriented toward a second direction perpendicular to the first direction in each of the raised ridge portions, and the content of the fiber oriented toward the second direction in the fibers which make up the groove portions is greater than the content of the fiber oriented toward the first direction in each of the groove portions.

In an eleventh aspect of the multilayer absorbent body as described in either of the ninth and tenth aspects of the present invention, a plurality of low amount of fiber regions including at least one of a plurality of depressed portions and openings is formed at regular intervals in an extended direction of the groove portions in each of the areas which make up the base of the groove portions, and at least part of sidewall portions which make up peripheral borders of each of the plurality of low amount of fiber regions are covered by the fibers which make up the first fiber layer.

In a twelfth aspect of the multilayer absorbent body as described in the ninth to eleventh aspects of the present invention, the multilayer absorbent body further contains the second fiber layer disposed on the side opposite to the first fiber layer in the absorbent body.

In a thirteenth aspect of the multilayer absorbent body as described in the twelfth aspect of the present invention, the first fiber layer and the second fiber layer are layered and formed by a card method, and the absorbent body is formed by layering fibers, which make up the absorbent body, on the first side of the first fiber layer by air-laid method.

In a fourteenth aspect of the present invention an absorbent article comprising a first fiber layer, an absorbent body containing absorbent fibers and a liquid-impermeable sheet wherein the absorbent body containing absorbent fibers is layered and disposed on a first side of the first fiber layer, the liquid-impermeable sheet is disposed on a side opposite to the first fiber layer in the absorbent body, a plurality of groove portions formed in the first direction depressed in the thickness direction of the multilayer absorbent body in relation to a second side of the first fiber layer, and a plurality of raised ridge portions formed adjacent to each of the groove portions raised in the thickness direction with a fiber basis weight that is greater than that of areas which make up a base of the groove portions are formed, the groove portions and the raised ridge portions contain the first fiber layer and the absorbent body, and the first fiber layer side of the absorbent body which make up each of the raised ridge portions is raised toward the same direction as the direction in which the second side of the first fiber layer is raised.

In a fifteenth aspect of the absorbent article as described in the fourteenth aspect of the present invention, a content of the fiber oriented toward the first direction, in the fibers which make up the raised ridge portions is greater than a content of the fiber oriented toward the second direction in each of the raised ridge portions, and a content of the fiber oriented toward the second direction, in the fibers which make up the groove portions is greater than a content of the fiber oriented toward the first direction in each of the groove portions.

In a sixteenth aspect of the absorbent article as described in either of the fourteenth and fifteenth aspects of the present invention, a plurality of low amount of fiber regions including at least one of a plurality of depressed portions and openings is formed at predetermined intervals in each of the groove portions, and at least part of the sidewall portions which make up peripheral borders of each of the plurality of low amount of fiber regions are covered by the fibers which make up the first fiber layer.

In a seventeenth aspect of the absorbent article as described in any one of the fourteenth to sixteenth aspects of the present invention, the absorbent article further contains a second fiber layer disposed between the absorbent body and the liquid-impermeable sheet.

In an eighteenth aspect of the present invention a method for manufacturing an absorbent body includes the step of, supporting a fiber aggregate of an absorbent body on a breathable support member from a first side by disposing the fiber aggregate of the absorbent body on a predefined surface of the breathable support member or layering and disposing the fibers containing absorbent fibers on the predefined surface, conveying the fiber aggregate of the absorbent body supported by the breathable support member in the first direction by means of a predefined conveying unit, and ejecting a fluid consisting mainly of gaseous matter to a second side of the fiber aggregate of the absorbent body, being conveyed in a first direction, by means of a predefined ejection unit, wherein the fiber aggregate of the absorbent body is formed in a sheet-like shape comprising absorbent fiber and is in a state where fibers composing the fiber aggregate have a degree of freedom.

In a nineteenth aspect of the present invention a method for manufacturing a multilayer absorbent body includes the steps of, supporting a multilayer fiber aggregate on a breathable support member from a first side by disposing the multilayer fiber aggregate on a predefined surface of the breathable support member or layering and disposing the fibers containing absorbent fibers and the first fiber layer on the predefined surface so as to form a multilayer fiber aggregate, conveying the multilayer fiber aggregate supported by the breathable support member in the first direction by means of a predefined conveying unit, and ejecting a fluid consisting mainly of gaseous matter to a second side of the multilayer fiber aggregate being conveyed in a first direction by means of a predefined ejection unit, wherein the multilayer fiber aggregate comprises a first fiber aggregate formed in a sheet like shape and being in a state where fibers composing the fiber aggregate have a degree of freedom, and a fiber aggregate of the absorbent body formed in a sheet like shape layered and disposed on a first side of the first fiber aggregate and being in a state where fibers composing the fiber aggregate have a degree of freedom.

In a twentieth aspect of the present invention a method for manufacturing a multilayer absorbent body includes the steps of, supporting a multilayer fiber aggregate on a breathable support member from a first side by disposing the multilayer fiber aggregate on a predefined surface of the breathable support member, conveying the multilayer fiber aggregate supported by the breathable support member in the first direction by means of a predefined conveying unit, and ejecting a fluid consisting mainly of gaseous matter to a second side of the multilayer fiber aggregate, being conveyed in a first direction, by means of a predefined ejection unit, wherein the multilayer fiber aggregate comprises a first fiber aggregate formed in a sheet like shape and being in a state where fibers composing the fiber aggregate have a degree of freedom, a fiber aggregate of the absorbent body formed in a sheet like shape layered and disposed on a first side of the first fiber aggregate and being in a state where fibers composing the fiber aggregate have a degree of freedom, and a second fiber aggregate formed in a almost sheet like shape and being in a state where fibers composing the fiber aggregate have a degree of freedom disposed on a side of the fiber aggregate of the absorbent body opposite to the first fiber layer.

In a twenty-first aspect of the method for manufacturing the multilayer absorbent body as described in the twentieth aspect of the present invention, supporting includes the steps of, disposing the second fiber aggregate on the predefined surface of the breathable support member, forming the fiber aggregate of the absorbent body by layering the fibers containing the absorbent fibers which constitute the fiber aggregate of the absorbent body, on a side of the second fiber aggregate opposite to the breathable support member, and forming the multilayer fiber aggregate by layering and disposing the first fiber aggregate on a side of the formed fiber aggregate of the absorbent body opposite to the second fiber aggregate.

In a twenty-second aspect of the method for manufacturing the multilayer absorbent body as described in the twenty-first aspect of the present invention, the fiber aggregate of the absorbent body is formed by an air-laid method.

Provided by the present invention is an absorbent body containing absorbent fiber in which fiber orientation is mainly adjusted, and fiber basis weight and shape are additionally adjusted.

BRIEF DESCRIPTION OF THE DRAWINGS

FIG. 1 shows a perspective view of a fiber web;
FIG. 2 shows a perspective cross section of an absorbent body in the first embodiment.

DETAILED DESCRIPTION OF THE INVENTION

The best embodiments of the present invention will be explained referring to figures below.

1. Absorbent Body

The embodiments of the absorbent body of the present invention will be explained referring to FIGS. 1 to 22.

1-1. First Embodiment

Figure 3A:
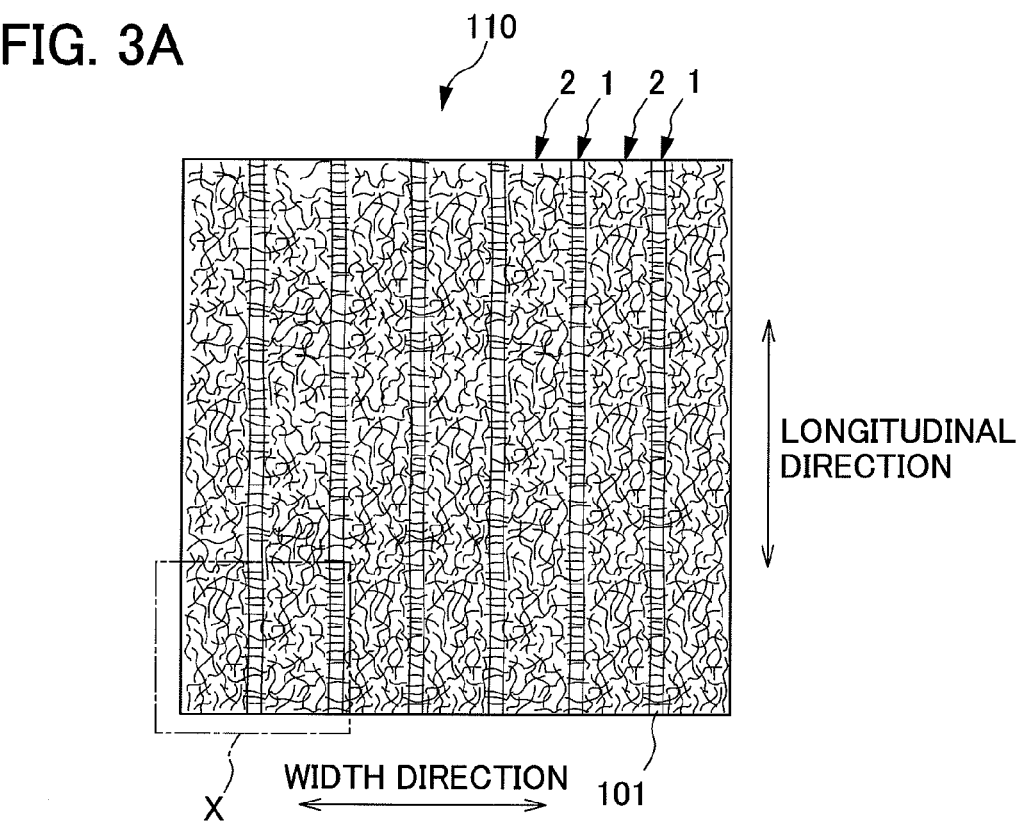
FIG. 3A shows a plan view of the absorbent body in the first embodiment and FIG. 3B shows a bottom view of the absorbent body in the first embodiment.
Figure 3B:
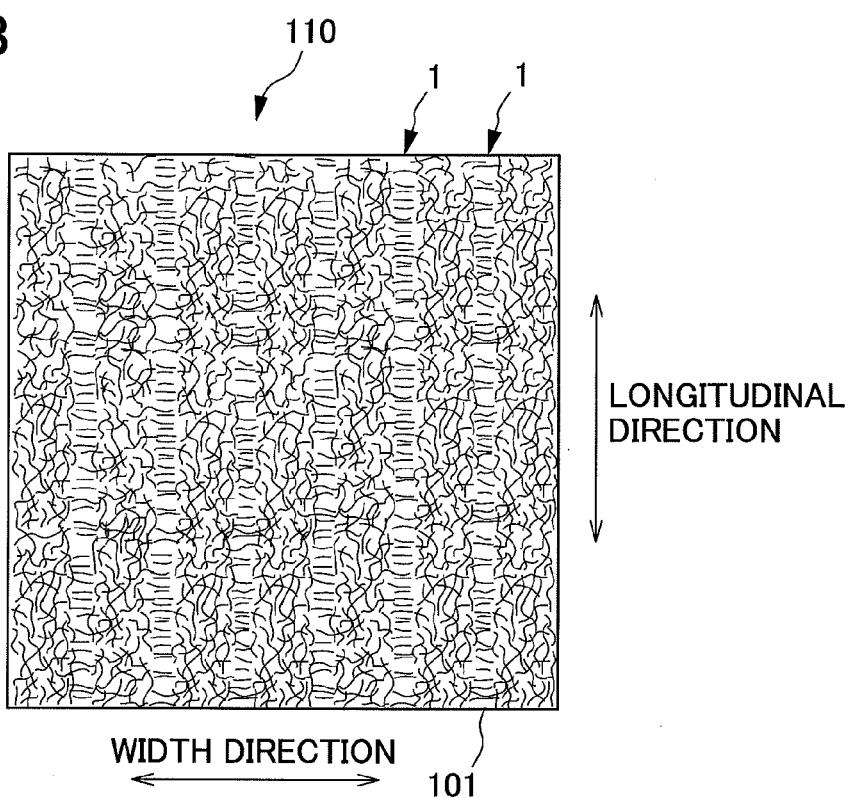

The absorbent body in the first embodiment will be explained referring to FIGS. 1 to 9.
1-1-1. Absorbent Body
As shown in FIGS. 2, 3A and 3B, the absorbent body 110 in the first embodiment is an absorbent body containing absorbent fibers, and a plurality of groove portions 1 are formed along the machine direction (longitudinal direction or first direction) so as to be in parallel with each other at almost regular intervals in relation to the cross direction (width direction or second direction) perpendicular to the machine direction on the first side of the absorbent body 110. Each of the raised ridge portions 2 is formed in between each of the groove portions 1 formed at almost regular intervals. The raised ridge portions 2 are formed in parallel with each other at almost regular intervals in relation to the cross direction as similar to the groove portions 1. Even though the groove portions 1 are formed in parallel with each other at almost regular intervals in the first embodiment, they are not limited to the above and the groove portions 1 may be formed at irregular intervals or may not be in parallel with each other and distances between groove portions 1 may vary in relation to the machine direction, for example.

Even though heights (in the thickness direction) of the raised ridge portions 2 of the absorbent body 110 in the first embodiment are approximately uniform, the raised ridge portions 2 may be formed so that the adjacent raised ridge portions 2 have different heights. For example, heights of the raised ridge portions 2 can be adjusted by regulating intervals of the ejection holes 913 of the manufacturing apparatus 90 as described below from which fluids consisting mainly of gaseous matter are ejected. For example, heights of the raised ridge portions 2 can be decreased by narrowing the intervals of the ejection holes 913, and reversely, heights of the raised ridge portions 2 can be increased by widening the intervals of the ejection holes 913. Furthermore, the raised ridge portions 2 having different heights can be formed alternately by forming the ejection holes 913 at narrow intervals and wide intervals in alternate fashion. If a multilayer nonwoven fabric on which the raised ridge portions 2 with different heights are formed alternately is disposed so as to be in contact with the body, contact area with skin is reduced as compared to the multilayer nonwoven fabric having the raised ridge portions 2 with uniform heights, thereby reducing adverse effects on the skin.

In the first embodiment, the raised ridge portions 2 are high fiber basis weight regions, and the areas which make up the base of the groove portions 1 are low fiber basis weight regions. The absorbent body 110 in the first embodiment has a plurality of low fiber basis weight regions formed continuously along the machine direction (longitudinal direction) with a fiber basis weight that is less than an average fiber basis weight of the absorbent body, and a plurality of high fiber basis weight regions formed on both sides of the low fiber basis weight regions along the low fiber basis weight regions in relation to the machine direction (longitudinal direction) with a fiber basis weight that is greater than the average fiber basis weight. Of the fiber which make up the high fiber basis weight regions, the content of fiber oriented toward the longitudinal direction of the absorbent body in the range of −45° to +45° in relation to the machine direction (longitudinal direction) is greater than the content of fiber oriented toward the width direction of the absorbent body, which are not the fiber oriented toward the longitudinal direction of the absorbent body, in each of the high fiber basis weight regions. Of the fibers which make up the low fiber basis weight regions, the content of fibers oriented toward the width direction of the absorbent body is greater than the content of fibers oriented toward the longitudinal direction of the absorbent body in each of the low fiber basis weight regions.

The measurement of fiber orientation was performed by the measurement method below using the digital microscope VHX-100 by Keyence Corporation. (1) A sample is set on the observation table in a way so that the length direction is in the longitudinal direction. (2) Fibers sticking out irregularly in front are removed and lens is focused on the nearest front fiber of the sample. (3) Depth is set and 3D image of the sample is created on the computer screen. Next, (4) the 3D image is converted to a 2D image. (5) A plurality of parallel lines are written on the screen equally dividing the length direction in the measurement range. (6) Fiber orientation in each cell divided by the parallel lines is observed and determined if it is in the length direction or width direction and the number of fibers oriented in each direction are measured. (7) The ratio of number of fibers oriented in the length direction and the ratio of number of fibers oriented in the width direction are calculated relative to the total number of fibers within the measurement range, thereby determining the fiber orientation.

When the absorbent body 110 in the first embodiment is used for absorbent articles such as sanitary napkins, etc., for example, liquids such as menstrual blood, etc. migrated from the surface sheets migrates along the extended direction of the raised ridge portions 2 because the fibers 101 which make up the raised ridge portions 2 as the high fiber basis weight regions are oriented in the direction (machine direction, longitudinal direction or first direction) toward which the raised ridge portions 2 are formed continuously. Furthermore, the low fiber basis weight regions which make up the base of the groove portions 1 and lie adjacent to the raised ridge portions 2, which are the high fiber basis weight regions, have less number of fiber per unit area thus lowering capillary force, and liquids such as menstrual blood, etc. are not likely to be absorbed in the width direction (cross direction) perpendicular to the extended direction of the raised ridge portions 2.

Moreover, the absorbent body 110 can easily bended at the groove portions 1 because the groove portions 1 are formed as the low fiber basis weight regions. This allows the absorbent articles to conform to the shape of the body to fit the body better. In addition, even though the areas which make up the base of the groove portions 1 have a low fiber basis weight, the fibers which make up the base of the groove portions 1 are oriented in the width direction of the groove portions 1, thereby increasing the strength in the width direction (width direction of the groove portions 1, or cross direction) of the absorbent body 110. This prevents the absorbent articles from being twisted or damaged by bodily movement during use.

The absorbent body comes in contact with the surface sheet disposed on the skin side of the absorbent body 110 and comes in contact mainly with the raised ridge portions 2 that are the high fiber basis weight regions. Stated differently, the surface sheets can prevent rewetting of menstrual blood from the absorbent body caused by external pressure, etc. because the surface sheets do not actually come in contact with the base of the groove portions 1 that are the low fiber basis weight regions.

1-1-2. Method for Manufacturing

Figure 4A:
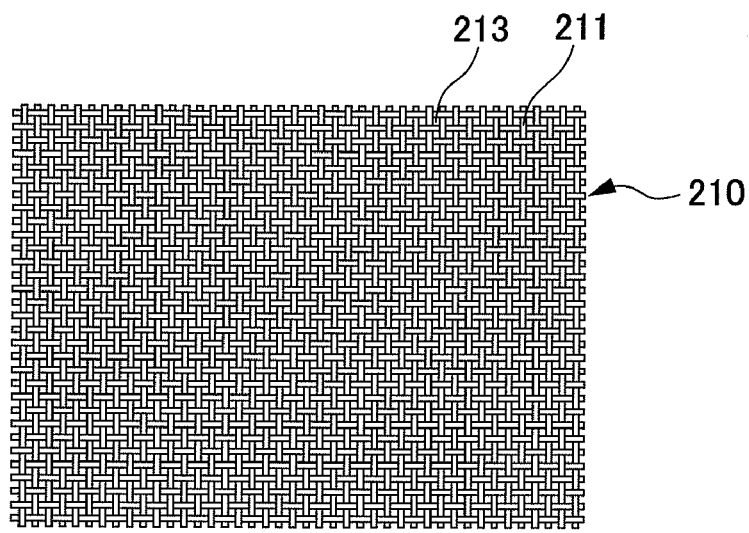
FIG. 4A shows a plan view of a net-like support member and FIG. 4B shows a perspective view of the net-like support member.
Figure 4B:
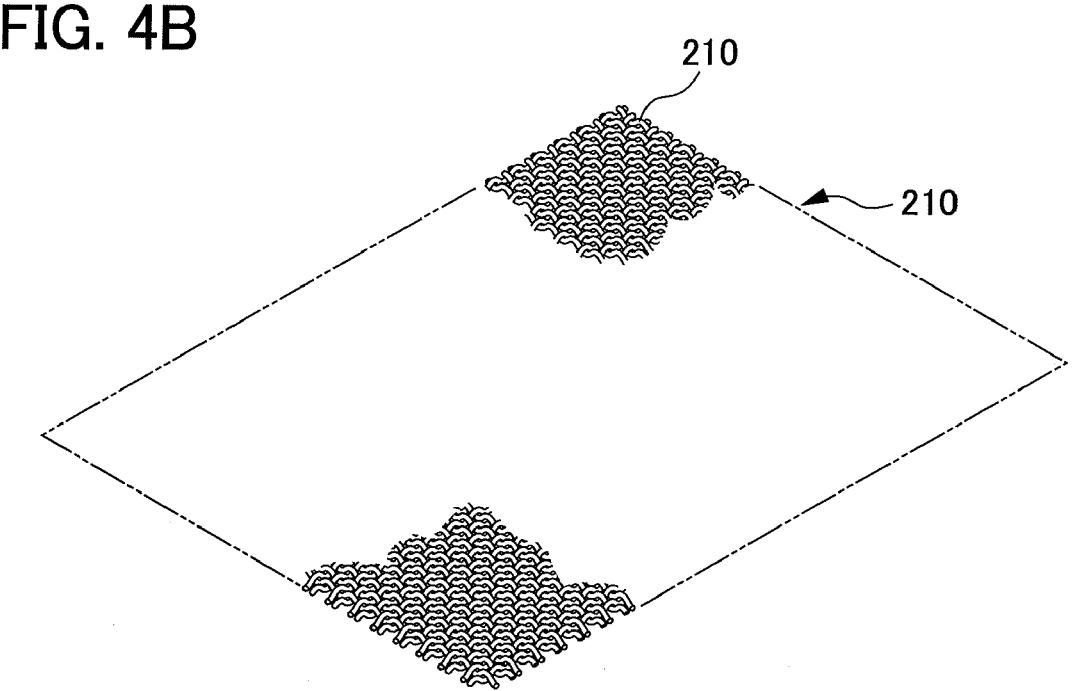
Figure 5:
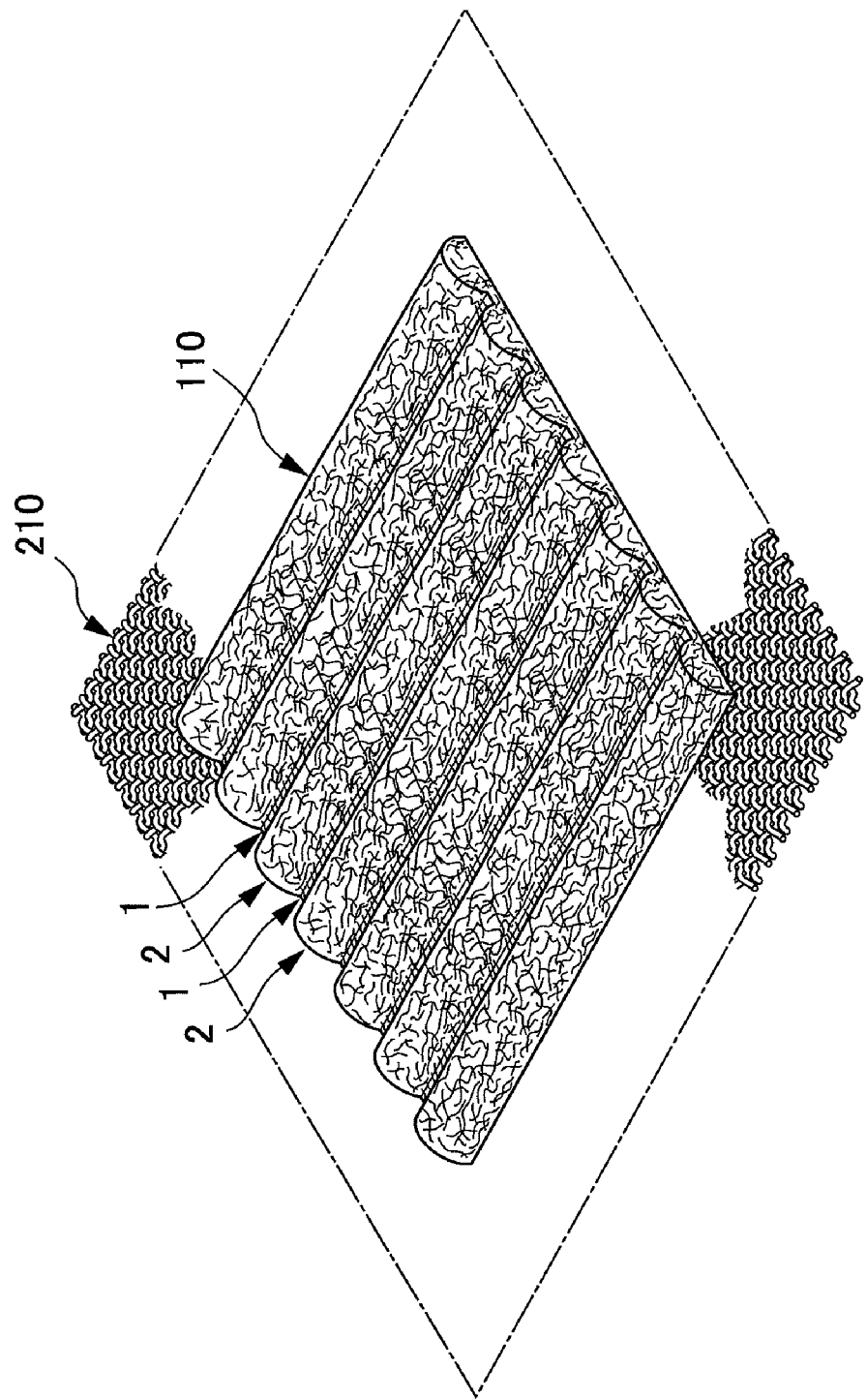
FIG. 5 is a view showing the absorbent body in the first embodiment as shown in FIG. 2 produced by ejecting a gaseous matter to an upper side of the fiber web as shown in FIG. 1 while the fiber web is being supported by the net-like support member, as shown in FIG. 4, from beneath.
Figure 6:
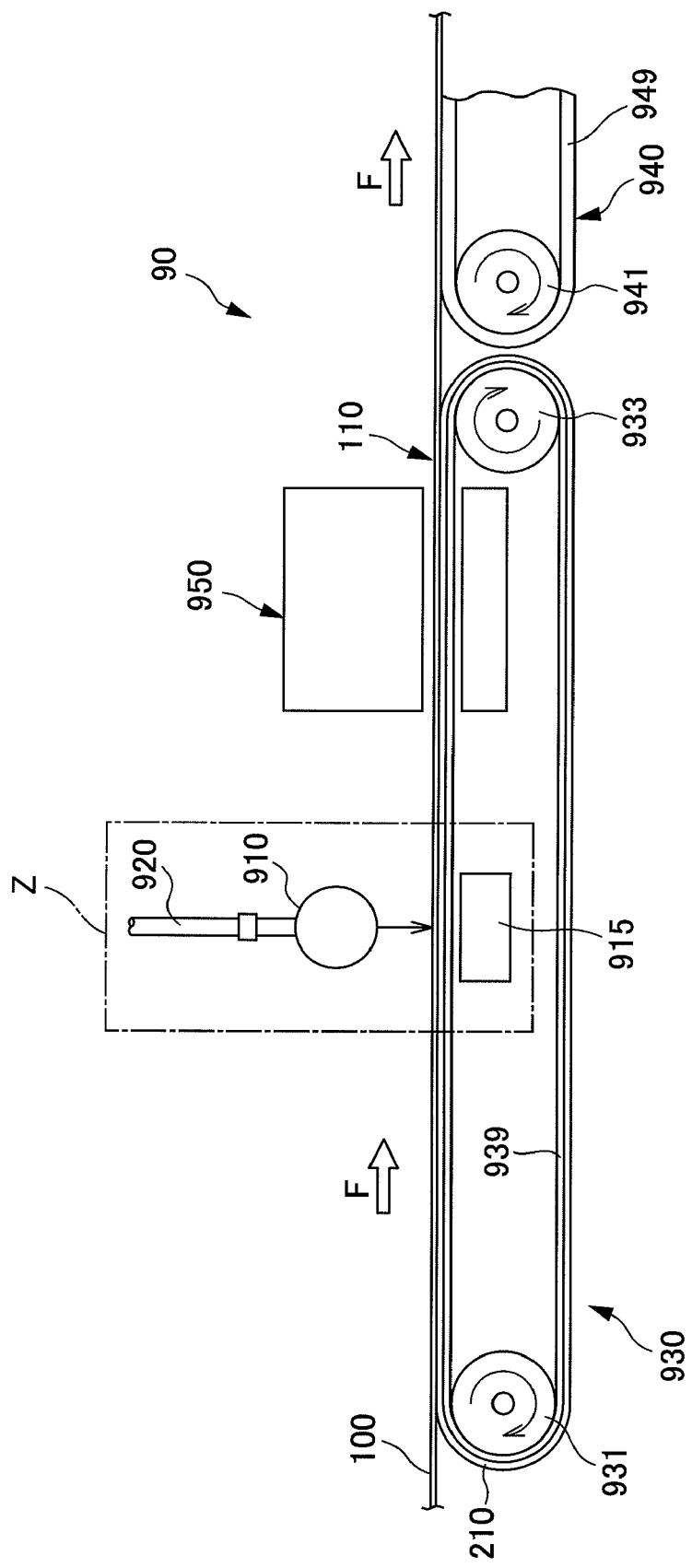
FIG. 6 shows a side view for explaining an absorbent body manufacturing apparatus.
Figure 7:
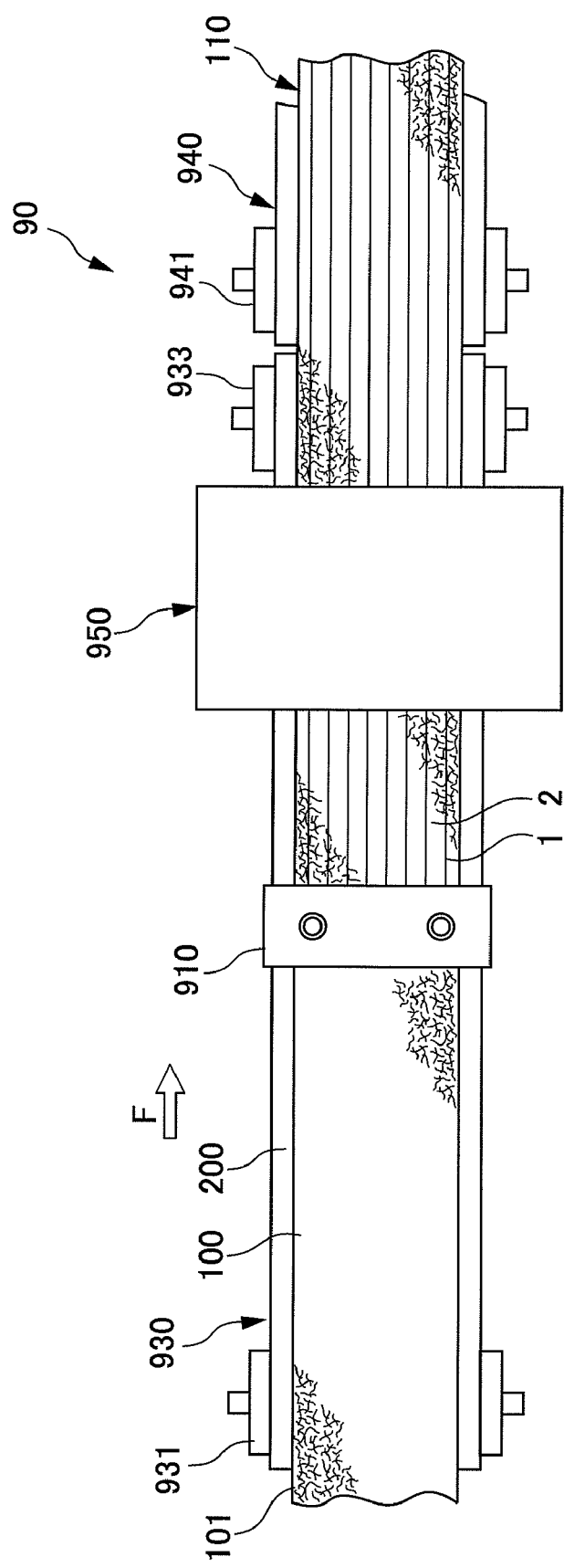
FIG. 7 shows a plan view for explaining an absorbent body manufacturing apparatus.
Figure 8:
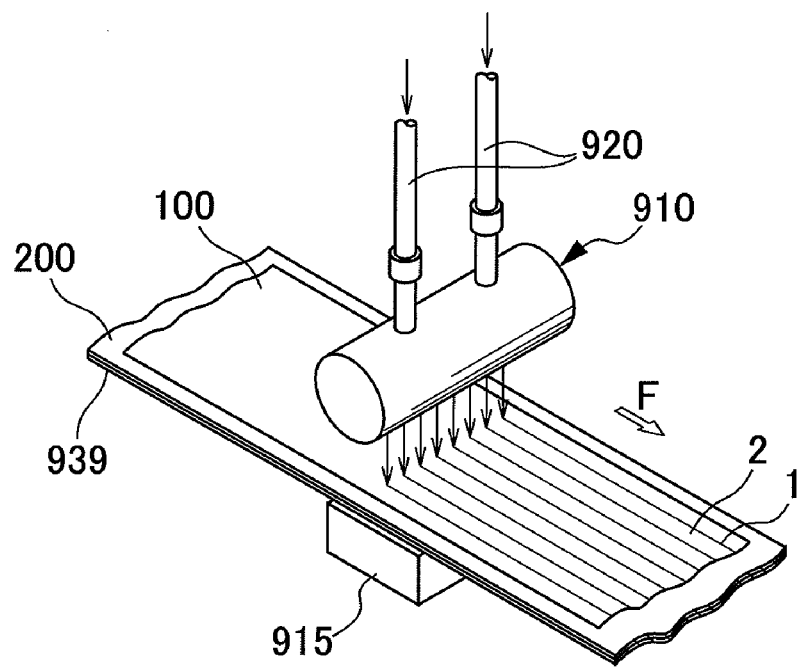
FIG. 8 shows an enlarged perspective view of an area Z as defined in FIG. 6.
Figure 9:
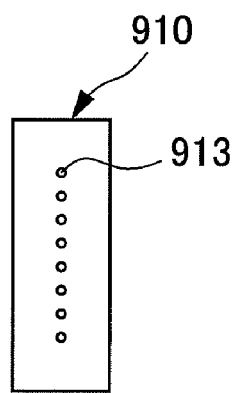
FIG. 9 shows a bottom view of an ejection unit in FIG. 6.
Figure 10:
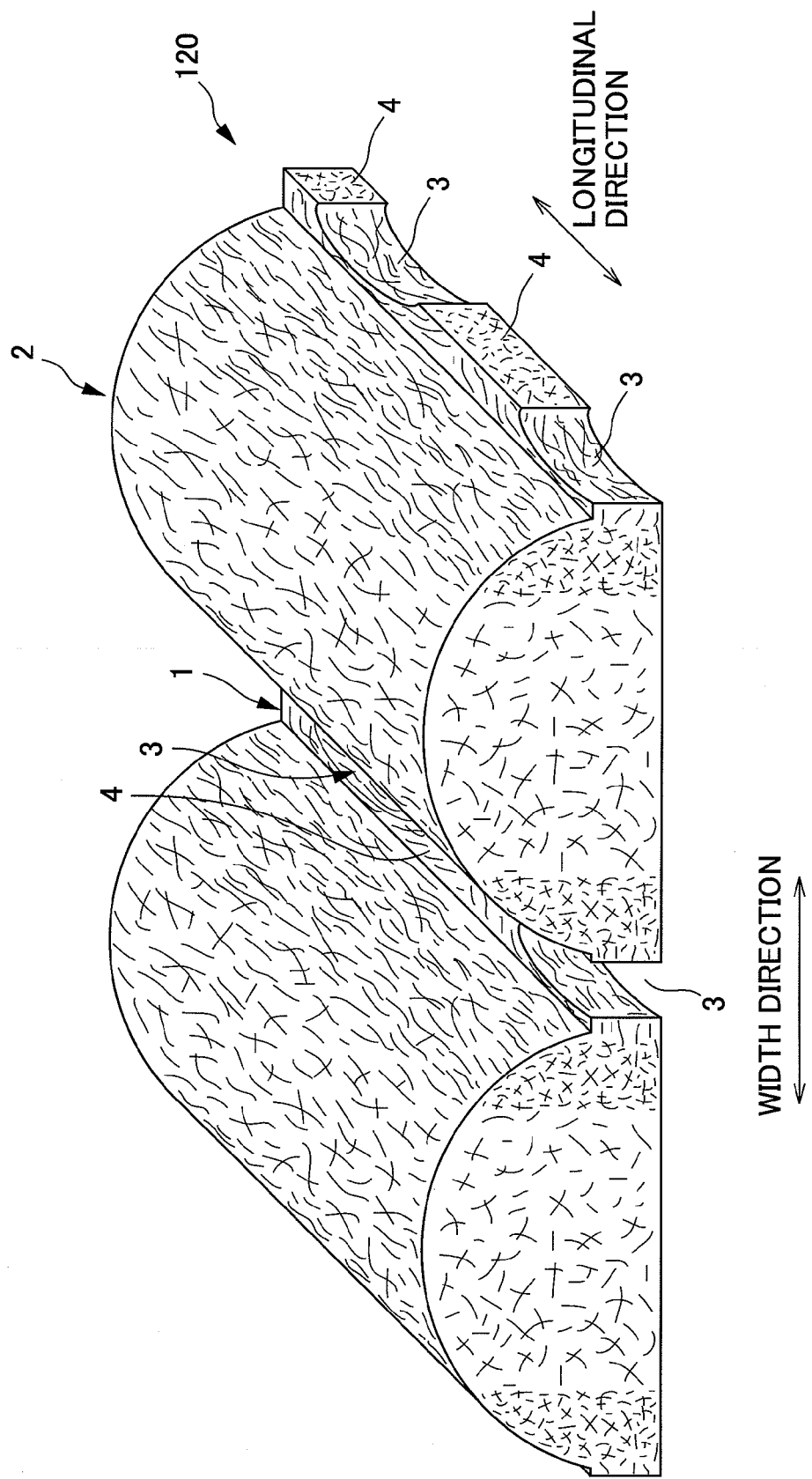
FIG. 10 shows a perspective cross section of an absorbent body in the second embodiment.

The method for manufacturing the absorbent body 110 will be explained referring to FIGS. 1, 6 and 9. First, a fiber web 100 containing absorbent fibers as shown in FIG. 1 is placed on an upper side of a net-like support member 210 as a breathable support member as shown in FIG. 4. Stated differently, the fiber web 100 is supported by the net-like support member 210 from beneath. Examples of the methods for placing the fiber web 110 on the net-like support member 210 include a method in which a sheet-like fiber web 100 is placed on the upper side of the net-like support member 210 and a method in which fibers containing absorbent fibers are layered on the upper surface of the net-like support member 210 by air-laid method.

The net-like support member 210 supporting the fiber web 100 is then conveyed in the machine direction, and a gaseous matter is ejected continuously to an upper side of the fiber web 100 being conveyed to manufacture the absorbent body 110 in the first embodiment.

Weaving a plurality of impervious wires 211 of a specific thickness forms the net-like support member 210 as shown in FIG. 4. A plurality of holes 213 are formed in the net-like support member 210 by weaving the wires 211 at predefined intervals to ensure ventilation.

A plurality of holes 213 with a small hole diameter are formed in the net-like support member 210 as described above, and the gaseous matter ejected to the upper side of the fiber web 100 and ventilated through the fiber web is ventilated downward (opposite of the disposed side of the fiber web) without being hampered by the net-like support member 210. The net-like support member 210 does not significantly change flow of ejected gaseous matter, and the fibers 101 are not displaced downward in the net-like support member 210.

Therefore, the fibers 101 in the fiber web 100 are displaced in a specified direction by the gaseous matter ejected mainly to the upper side. Specifically, the fibers 101 are displaced in a direction along the surface of the net-like support member 210 because downward displacement through the net-like support member 210 is restricted.

For example, the fibers 101 in an area where the gaseous matter is ejected are displaced to an adjacent area. And since the fiber web 100 moves in the machine direction while the gaseous matter is being ejected, the area where the fibers 101 are displaced in is formed along the machine direction. In other words, the fibers 101 are displaced to the side of the area where the gaseous matter is ejected.

This form the groove portions 1 while the fibers 101 mostly oriented toward the machine direction are displaced to the sides. And the fibers 101 oriented toward the cross direction perpendicular to the machine direction are left in the base of the groove portions 1. Moreover, the raised ridge portions 2 are formed on the sides of the groove portions 1, that is, in between the adjacent groove portions 1. The fiber density of the sides of the raised ridge portions 2, which are formed by moving the fibers 101 oriented in the machine direction from the area where the groove portions 1 are formed, is increased, and of the fibers 101 and 102, ratio of the fibers 101 oriented in the length direction is also increased.

The fiber web 100 may be made only of absorbent fibers, or may be made of a mixture of absorbent fibers and thermally adhesive fibers. Specifically, 80% by weight to 100% by weight of pulp and 20% by weight to 0% by weight of a fiber having a core-in-sheath structure of polyethylene and polypropylene are mixed and adjusted to have a fiber basis weight of 10 $g/m^2$ to 1,000 $g/m^2$ for use. An average fiber length of fibers which make up the fiber web 100 is 1 mm to 20 mm and preferably 2 mm to 10 mm.

The absorbent fibers are the fibers having a water-absorbing property, or the fibers provided with a water-absorbing property. Examples of the fibers having a water-absorbing property include cellulose fibers. Examples of the fibers provided with a water-absorbing property include synthesized fibers or contractile fibers provided with a hydrophilic property. The details are as described below.

Since the groove portions 1 and the raised ridge portions 2 are formed by ejecting a fluid consisting mainly of gaseous matter to a predefined surface of the fiber web 100 containing fibers with a short fiber length, it is preferable to perform suctioning (air intake) from an opposite side of the fiber web 100 on the net-like support member 210. For example, suctioning (air intake) can be started right before the fluid consisting mainly of gaseous matter is ejected to the predefined surface of the fiber web 100.

Performing suctioning (air intake) from an opposite side of the net-like support member 210 closely attaches the fiber web 100 to the net-like support member 210 and prevents fiber dispersal due to ejection of the fluid consisting mainly of gaseous matter. This allows the groove portions 1 and the raised ridge portions 2 to be formed on a predefined surface of the fiber web 100 in preferred shapes.

1-1-3. Absorbent Body Manufacturing Apparatus

The absorbent body manufacturing apparatus 90 for manufacturing the absorbent body 110 will be explained referring to FIGS. 6 to 9.

The absorbent body manufacturing apparatus 90 contains a breathable support member which supports the fiber web 100 as a fiber aggregate from the first side, an ejection unit 910 which makes up the ejection unit from which fluids consisting mainly of gaseous matter are ejected to the second side of the fiber web 100 supported by a breathable support member from beneath, an air supplying unit not shown in figures and a conveyer 930 as a conveying unit which conveys the fiber web 100 in a specified direction F, the machine direction.

The fiber web 100 is conveyed in the specified direction F by the conveyer 930 as a conveying unit while being supported by the breathable support member from the first side, and the fluid consisting mainly of gaseous matter is ejected to the second side of the fiber web 100 by the ejection unit 910 as an ejection unit and the air supplying unit (not shown) while being conveyed by the conveyer 930 in the specified direction F.

The fibers 101 which make up the fiber web 100 are displaced by the fluid consisting mainly of gaseous matter ejected from the ejection unit 910, and/or the fluid consisting mainly of gaseous matter ejected from the ejection unit 910 and ventilated through the fiber web 100 while impervious portions formed in the breathable support member as described below changing the direction of air flow. The displaced amount of the fibers 101 is adjusted in order to adjust fiber orientation, density or fiber basis weight of the fibers 101 to thereby form predefined groove portions 1 (and the raised ridge portions 2) or openings 3, which will be described later.

Transfer of the fibers 101 which make up the fiber web 100 can be adjusted by changing ejection condition of the fluid consisting mainly of gaseous matter. In other words, fiber orientation, density or fiber basis weight of the absorbent body 110, or shapes of the predefined groove portions 1 (and the raised ridge portions 2) or openings 3 described below can be adjusted by mainly adjusting ejection condition of the fluid consisting mainly of gaseous matter in addition to the shapes and arrangements of the breathable portions in the breathable support member and absorbent body.

1-2. Second Embodiment

An absorbent body in the second embodiment will be explained referring to FIGS. 11 to 15. The absorbent body 120 in the second embodiment is an absorbent body in which a plurality of openings 3 are formed at regular intervals in the base of the groove portions 1, which are the low fiber basis weight regions of the absorbent body 110 in the first embodiment. Meanwhile, the groove portions 1 in the second embodiment are formed in parallel with each other at almost regular intervals in relation to the cross direction, however, they are not limited to the above and may be formed at irregular intervals, or may not be in parallel with each other and the intervals between groove portions 1 may also vary in relation to the machine direction. Heights of the raised ridge portions 2 may not be uniform but different from each other. A plurality of openings 3 are formed in the second embodiment, however, a plurality of depressed portions (not shown) may be formed instead of the openings 3.

1-2-1. Absorbent Body

Figure 11:
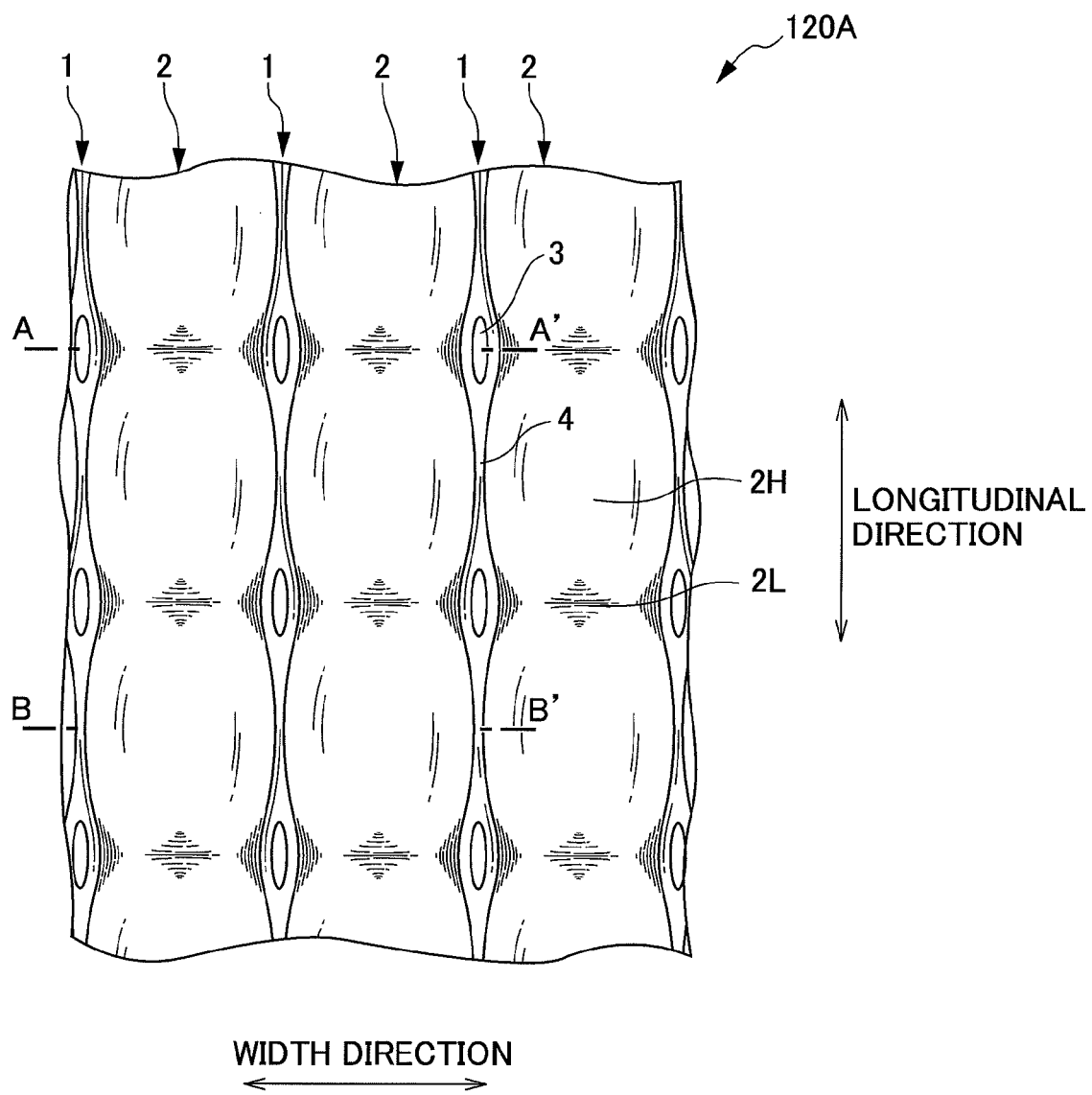
FIG. 11 shows a plan view of the absorbent body in the second embodiment.

The groove portions 1 in the absorbent body 120 in the second embodiment as shown in FIG. 11 are formed wider in the area where the openings 3 are formed and narrower in the area where the openings 3 are not formed. Adversely, the raised ridge portions 2 are formed narrower in the area where the openings 3 are formed and wider in the area where the openings 3 are not formed in relation to the cross direction.

Figure 12A:
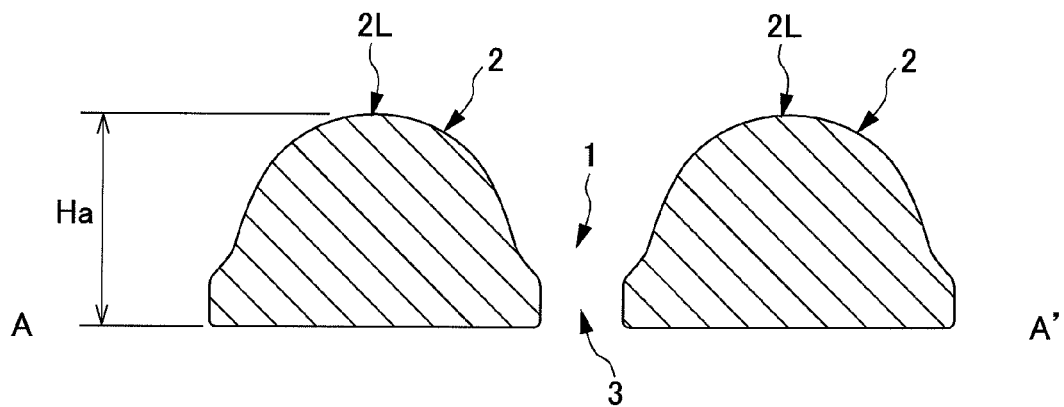
FIG. 12A shows a cross section of a line stretched from A to A' in FIG. 11
Figure 12B:
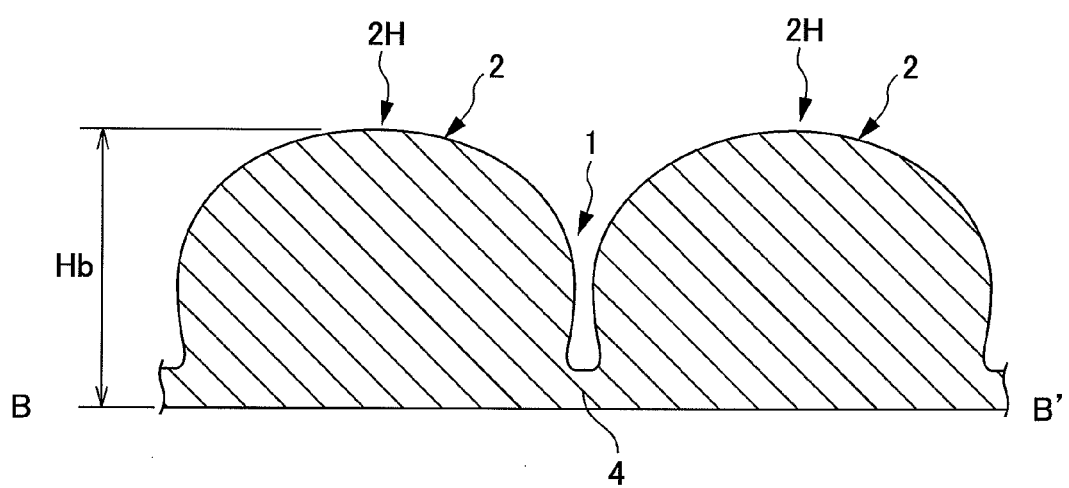
FIG. 12B shows a cross section of a line stretched from B to B' in FIG. 11.
Figure 13A:
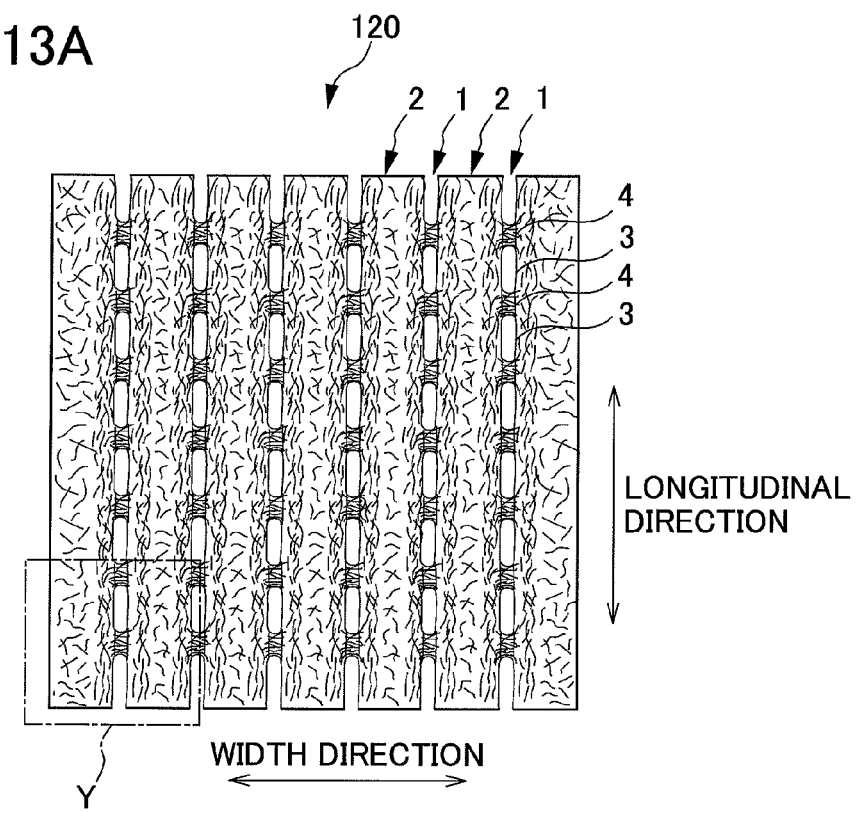
FIG. 13A shows a plan view of the absorbent body in the second embodiment and FIG. 13B shows a bottom view of the absorbent body in the second embodiment.
Figure 13B:
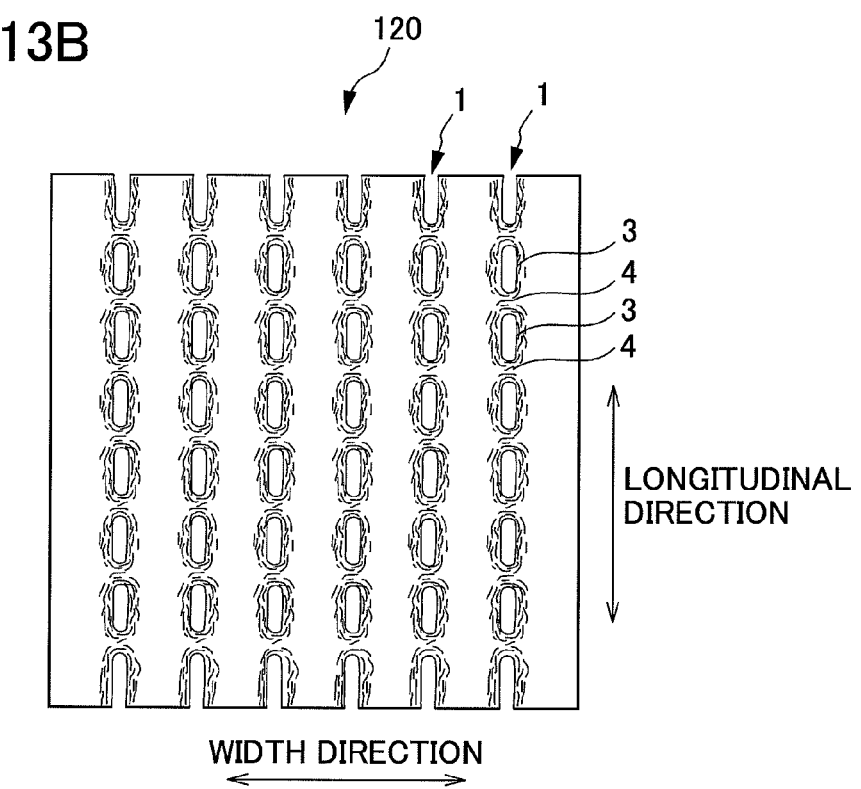

Heights of the raised ridge portions 2 (lengths in the thickness direction) are not uniform in the extended direction of the raised ridge portions 2. Stated differently, the height Ha of the raised ridge portions 2 which lie adjacent to the area where the openings 3 are formed in relation to the cross direction is lower than the height Hb of the raised ridge portions 2 which lie adjacent to the area where the openings 3 are not formed as shown in FIGS. 11, 12A and 12B. When the depressed portions are also formed in addition to the openings 3, thickness of the depressed portions (not shown) in the raised ridge portions 2, which are the high fiber basis weight regions in relation to the cross direction, and the side areas disposed on both sides of the openings 3 are thinner than the thickness of the areas other than the side areas of the raised ridge portions 2 as the high fiber basis weight regions.

The tops of the raised ridge portions 2 are corrugated moderately in the thickness direction in relation to the direction (machine direction) of the raised ridge portions 2 extended continuously. The raised ridge portions 2 are formed so that the first raised ridge portions 2L with heights decreasing in the thickness direction, and the second raised ridge portions 2H with heights increasing in the thickness direction alternate continuously in the extended direction of the raised ridge portions 2.

The fibers 101 disposed in peripheral borders of the openings 3 are oriented along the peripheral borders of the openings 3. Stated differently, edges of the openings 3 in relation to the length direction (machine direction) of the groove portions 1 are oriented in the cross direction perpendicular to the length direction. The sides of the openings 3 in relation to the length direction (machine direction) of the groove portions 1 are oriented along the length direction (machine direction).

A joint portion 4 is formed between adjacent openings 3 so as to connect adjacent raised ridge portions 2. Stated differently, a plurality of joint portions 4 formed at regular intervals are connecting the adjacent raised ridge portions 2.

The raised ridge portions 2 are adjusted so as to have the fibers 101 with a fiber basis weight that is greater than that of the areas which make up the base of the groove portions 1 as stated above. The fiber basis weight of the areas which make up the base of the groove portions 1 are adjusted to be less than an average fiber basis weight of the entire areas including the groove portions 1 and the raised ridge portions 2.

When the absorbent body 120 in the second embodiment is used for absorbent articles such as sanitary napkins, etc., menstrual blood can be fed into the openings 3 even if the menstrual blood of high viscosity is discharged near the openings 3 because the openings 3 are formed in the areas which make up the base of the groove portions 1 as the low fiber basis weight regions, so that the menstrual blood of high viscosity is prevented from covering entire surface of the absorbent body. This can prevent degradation of absorbability of the absorbent articles, for example.

Furthermore, since the heights of the raised ridge portions 2 in the thickness direction vary from high to low in the direction (machine direction or length direction) toward which the raised ridge portions 2 are formed continuously, the absorbent body can be easily bended in the direction toward which the raised ridge portions 2 are formed continuously, for example. This helps the absorbent body to conform to the shape of the body to fit better.

1-2-2. Manufacturing Method

Figure 14A:
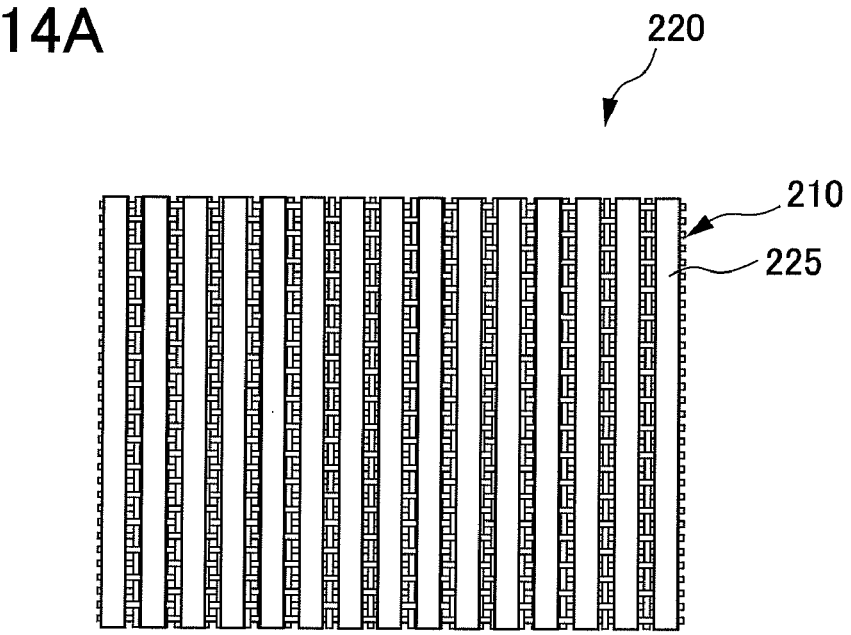
FIG. 14A shows a plan view of a support member in which slender members are disposed in parallel with each other at regular intervals on a net-like support member and FIG. 14B shows a perspective view of a support member in which slender members are disposed in parallel with each other at regular intervals on a net-like support member.
Figure 14B:
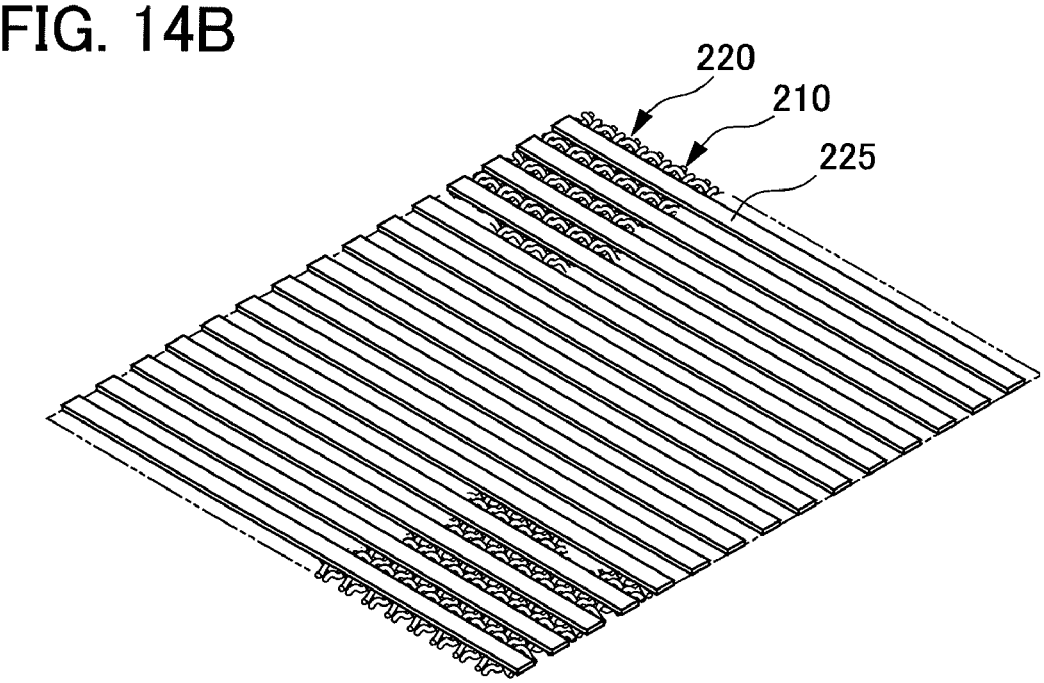
Figure 15:
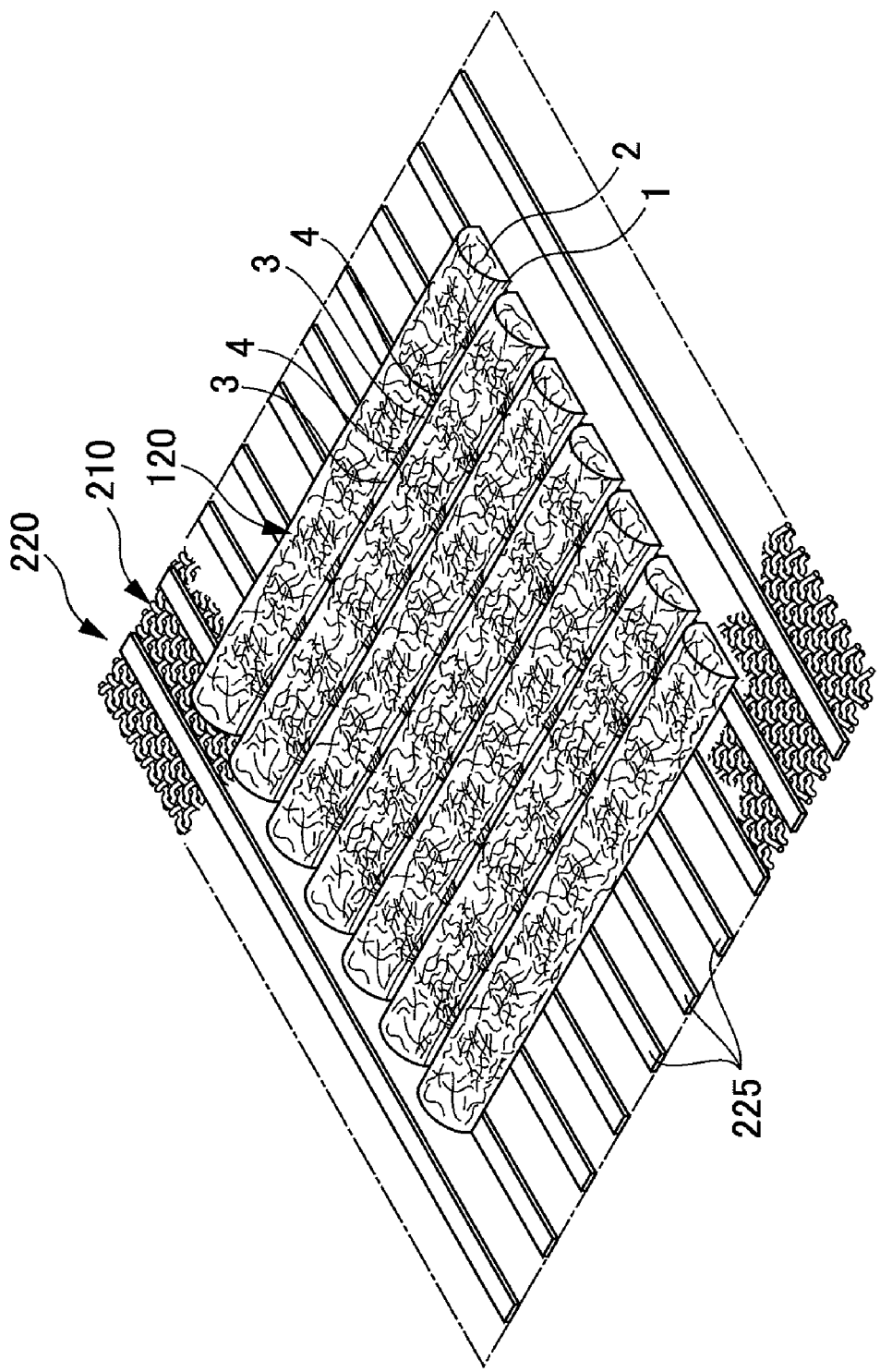
FIG. 15 is a view showing the absorbent body in the second embodiment as shown in FIG. 10 produced by ejecting a gaseous matter to an upper side of the fiber web as shown in FIG. 1 while the fiber web is being supported by the net-like support member as shown in FIG. 14 from beneath.

The method for manufacturing the absorbent body 120 in the second embodiment will be explained below. First, the fiber web 100 containing absorbent fibers is placed on an upper side of the support member 220 as a breathable support member as shown in FIG. 14. In other words, the fiber web 100 is supported by the support member 220 from beneath.

The absorbent body 120 in the second embodiment can be manufactured by conveying the support member 220 supporting the fiber web 100 in a specified direction, and ejecting a gaseous matter continuously to an upper side of the fiber web 100 being conveyed.

The support member 220 is placed on the conveyer so that the slender members 225 are placed along the cross direction perpendicular to the machine direction. The support member 220 on which the fiber web 100 is placed on upper side is conveyed in the machine direction. By this, a gaseous matter is ejected continuously to the upper side of the fiber web 100 in the direction approximately perpendicular to the extended direction of the slender members 225. Stated differently, the groove portions 1 are formed along the direction approximately perpendicular to the extended direction of the slender members 225, which is the machine direction. The openings 3 described below are then formed in the area disposed on the slender members 225 of the areas where the groove portions 1 are formed.

As described above, the support member 220 is a support member in which a plurality of slender members 225 are disposed approximately in parallel with each other at regular intervals on an upper side of the net-like support member 210. The slender members 225 are impervious members, and block the gaseous matter ejected from above (first side) so that it is not ventilated downward (second side). In other words, the gaseous matter ejected to the slender members 225 changes its flow direction.

Moreover, the slender members 225 block the fibers 101 which make up the fiber web 100 so that they are not displaced from upper side (first side) to the lower side (second side) of the support member 220.

The fibers 101 which make up the fiber web 100 are displaced by the gaseous matter ejected to an upper side of the fiber web 100 and/or ventilated through the fiber web 100 while flow direction thereof is being changed by the slender members 225.

For example, the fibers 101 in the areas where the gaseous matter is ejected are displaced to adjacent areas. Specifically, the fibers 101 oriented toward the machine direction (length direction) are displaced in the cross direction (width direction) perpendicular to the machine direction.

The groove portions 1 are formed as described above. The fibers 101 left unmoved are oriented in the cross direction to form the base of the groove portions 1. In other words, the fibers 101 which make up the base of the groove portions 1 are oriented toward the width direction (cross direction). In addition, raised ridge portions 2 are formed in between adjacent groove portions 1. The fiber density of the sides of the raised ridge portions 2 becomes greater than that of the displaced fibers 101 as described above, and the ratio of the fibers 101 placed so as to be oriented toward the length direction (machine direction) increases in the fibers 101 which make up the sides of the raised ridge portions 2.

Furthermore, the ejected gaseous matter ventilated through the fiber web 100 while flow direction thereof is being changed by the slender members 225 displaces the fibers 101 which make up the fiber web 100 in the direction different from the above direction.

The fibers 101 are displaced in the direction along the upper side of the support member 220 on which the fiber web 100 is placed because the net-like support member 210 and slender members 225 which make up the support member 220 restrict the fibers 101 from moving downward to the side opposite to the side on which fiber web 100 is placed on the support member 220.

Specifically, the gaseous matter ejected to the slender members 225 flows along the surface of the slender members 225 after changing its flow direction. The gaseous matter which changed its flow displaces the fibers 101 placed on the upper side of the slender members 225 to the surrounding areas. This forms the openings 3 of specific shapes, and one, two or more of the orientation, density, and fiber basis weight of the fibers 101 are adjusted.

Figure 24A:
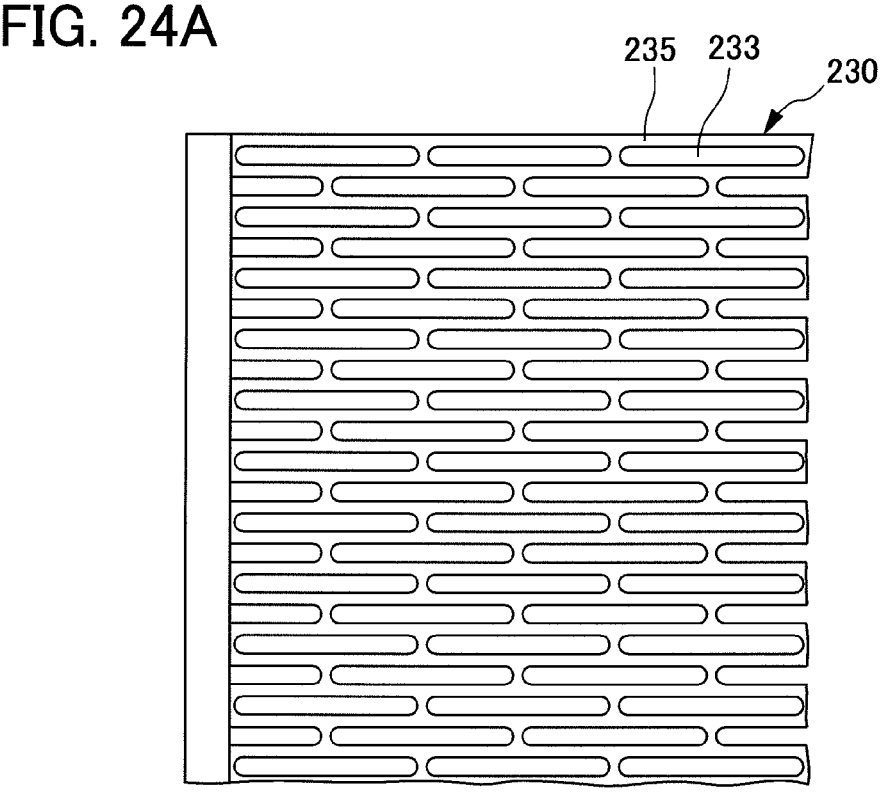
FIG. 24A shows a plan view of a plate-like support member in which a plurality of oval openings are formed and FIG. 24B shows a perspective view of the plate-like support member in which a plurality of oval openings are formed.
Figure 24B:
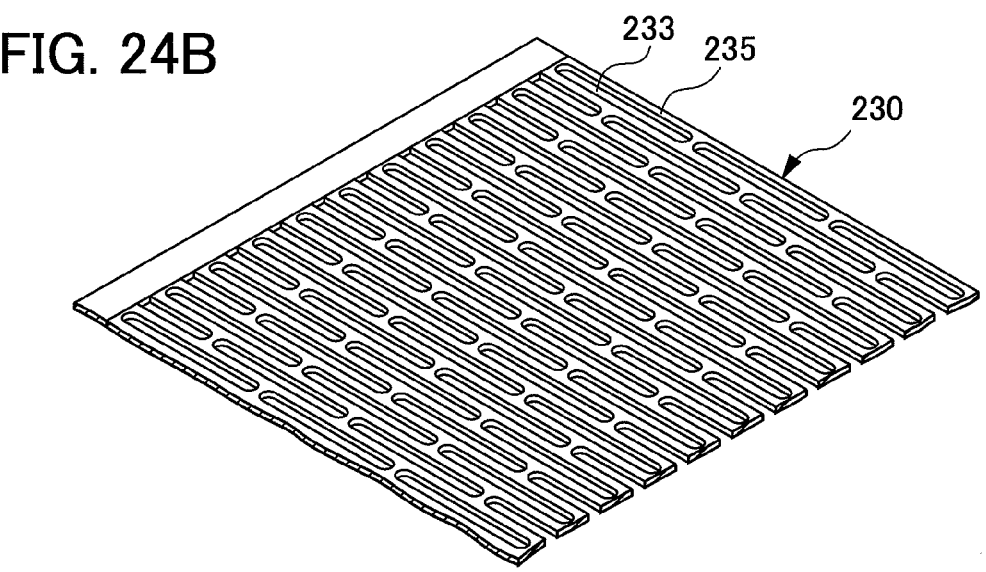

Moreover, the absorbent body 120 in the second embodiment can be obtained by adjusting temperature, volume or intensity of the fluid consisting mainly of gaseous matter ejected to the fiber web 100 and additionally adjusting moving speed of the fiber web 100 on the conveying unit and tension, etc. even if a plate-like support member 230 as shown in FIG. 24 is used.

The absorbent body 120 in the second embodiment can be manufactured by means of the above manufacturing apparatus 90. The operation of the manufacturing apparatus 90 in this case is as described above.

1-3. Third Embodiment

A multilayer absorbent body 140 in the third embodiment will be explained referring to FIG. 16. The multilayer absorbent body 140 in the third embodiment is a multilayer absorbent body containing a first fiber layer 141 and an absorbent body 142 layered and disposed on the first side of the first fiber layer 141. A plurality of groove portions 1A depressed in the thickness direction of the multilayer absorbent body 140, and a plurality of raised ridge portions 2A raised in the thickness direction and lie adjacent to each of the grove portions 1A in relation to the cross direction with a fiber basis weight that is greater than the fiber basis weight of the areas which make up the base of the groove portions 1A are formed on the second side of the first fiber layer 141. These groove portions 1A and the raised ridge portions 2A consist of the first fiber layer 141 and the absorbent body 142 in relation to the thickness direction. The first fiber layer 141 side of the absorbent body 142 which makes up the raised ridge portions 2A is raised on the same side as the second side of the first fiber layer 141. In addition, the first fiber layer 141 side of the absorbent body 142 which makes up the groove portions 1A is depressed on the same side as the second side of the first fiber layer 141.

The groove portions 1 of the multilayer absorbent body 140 in the third embodiment are formed in parallel with each other at approximately regular intervals, however, they are not limited to the above and may be formed at irregular intervals, or may not be in parallel with each other and intervals between groove portions 1 may also vary. Heights of the raised ridge portions 2A may also be different from each other instead of being uniform.

In each of the raised ridge portions 2A, the content of fibers oriented toward the longitudinal direction of the absorbent body in the fibers which make up the raised ridge portions 2A is greater than the content of fibers oriented toward the width direction of the absorbent body. And the content of fibers oriented toward the width direction of the absorbent body in the fibers which make up the base of the groove portions 1A is greater than the content of fibers oriented toward the longitudinal direction of the absorbent body in each of the groove portions 1A.

1-3-1. Shape

Figure 16:
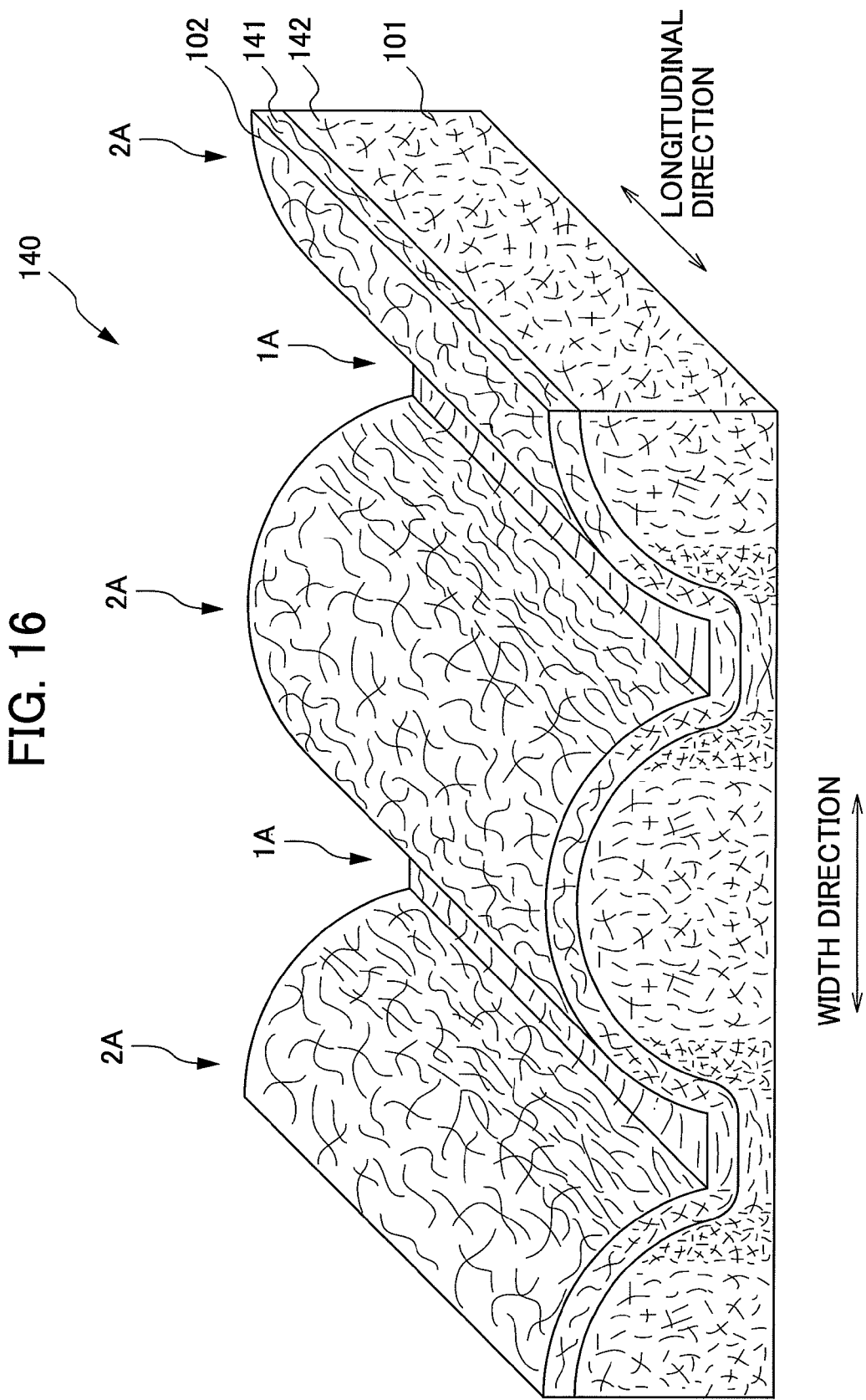
FIG. 16 shows a perspective cross section of a multilayer absorbent body in the third embodiment.

As shown in FIG. 16, the multilayer absorbent body 140 in the third embodiment is manufactured by layering and disposing the first fiber layer 141 and the absorbent body 142 as described above. The multilayer absorbent body 140 is an absorbent body in which a plurality of groove portions 1A are formed in parallel with each other at approximately regular intervals on the first side of the multilayer absorbent body 140, that is the first fiber layer 141 side of the multilayer absorbent body 140 in relation to the cross direction. And each of the raised ridge portions 2A is formed in between each of the groove portions 1A formed at approximately regular intervals in relation to the cross direction. The raised ridge portions 2A are formed in parallel with each other at approximately regular intervals as similar to the groove portions 1A. The groove portions 1A in the third embodiment are formed in parallel with each other at approximately regular intervals, however, they are not limited to the above and may be formed at irregular intervals, or may not be in parallel with each other and intervals between groove portions 1A may also vary in relation to the machine direction as described above.

These groove portions 1A and the raised ridge portions 2A consist of the first fiber layer 141 and the absorbent body 142. The absorbent body 142 in the multilayer absorbent body 140 is not simply a sheet-like absorbent body with a uniform thickness, but the shape thereof changes according to the shapes of the groove portions 1A, etc. formed on the first fiber layer 141 side.

The surface of the first fiber layer 141, which is opposite side of the surface on which the absorbent body 142 is disposed, makes up the surface of the raised ridge portions 2A. This surface is raised in U-like figure toward outside (upward in FIG. 16) of the multilayer absorbent body 140 in the thickness direction. The surface of the first fiber layer 141 on the absorbent body 142 side is also raised in U-like figure on the same side as the surface which makes up the surface of the raised ridge portions 2A.

The other surface (base) of the absorbent body 142, which is opposite side of the first fiber layer 141 side which makes up the other surface of the multilayer absorbent body 140, is formed flat. The surface of the absorbent body 142 on the first fiber layer 141 side is deformed so as to be raised along the surface of the first fiber layer 141 on the absorbent body 142 side. In other words, the surface of the absorbent body 142 on the first fiber layer 141 side is raised toward the same side as the outer surface of the first fiber layer 141 is raised in U-like figure.

Thickness of the first fiber layer 141 in the areas which make up the base of the groove portions 1A is less than the thickness of the absorbent body 142 in the raised ridge portions 2A.

The outer surface of the first fiber layer 141 in the groove portions 1A is depressed so as to become thinner in the thickness direction. In addition, the surface of the absorbent body 142 on the first fiber layer 141 side is depressed toward the same side as the outer surface of the first fiber layer 141.

Even though heights (in the thickness direction) of the multilayer absorbent body 140 in the raised ridge portions 2A are approximately uniform, the raised ridge portions 2A may be formed so that the adjacent raised ridge portions 2A have different heights, for example. For example, heights of the raised ridge portions 2A may be adjusted by controlling intervals of the ejection holes 913 from which fluids consisting mainly of gaseous matter are ejected. For example, heights of the raised ridge portions 2A can be decreased by narrowing the intervals of the ejection holes 913 in the absorbent body manufacturing apparatus 90 and reversely, heights of the raised ridge portions 2A can be increased by widening the intervals of the ejection holes 913. Furthermore, the raised ridge portions 2A having different heights can be formed alternately by forming the ejection holes 913 at a narrow interval and a wide interval in alternate fashion. When a multilayer nonwoven fabric in which the raised ridge portions 2A having different heights are formed alternately is placed in contact with the body, contact area with skin is reduced as compared to the case with a uniform height, thereby reducing adverse effects on the skin.

The height of the raised ridge portions 2A is preferably 0.3 mm to 15 mm and more preferably 0.5 mm to 5 mm. The width of the raised ridge portions 2A is preferably 0.5 m to 30 mm and more preferably 1.0 mm to 10 mm. The pitch between tops of the adjacent raised ridge portions 2A is preferably 0.5 mm to 30 mm and more preferably 3 mm to 10 mm.

The height (length in the thickness direction) of the absorbent body 142 in the raised ridge portions 2A is preferably 95% or less of the height of the raised ridge portions 2A, more preferably 20% to 90% and most preferably 40% to 70% of the height of the raised ridge portions 2A. The absorbent body 142 is formed so that the height (length in the thickness direction) in the raised ridge portions 2A is greater than the height in the groove portions 1A.

The height of the area which makes up the base of the groove portions 1A is preferably 90% or less of the height of the raised ridge portions 2A, more preferably 1% to 50% and most preferably 5% to 20% of the height of the raised ridge portions 2A. The width of the groove portions 1A is preferably 0.1 m to 30 mm and more preferably 0.5 mm to 10 mm. The pitch between adjacent groove portions 1A is preferably 0.5 mm to 20 mm and more preferably 3 mm to 10 mm. The height of the absorbent body (inner layer) 142 in the groove portions 1A is preferably 95% or less of the height (length in the thickness direction) of the groove portions 1A, more preferably 20% to 90% and most preferably 40% to 70% of the groove portions 1A.

The direction of measurement of height, pitch or width, etc. of the raised ridge portions 2A or the groove portions 1A is exemplified as follows. For example, a multilayer absorbent body 140 is placed on a table in a state free of external forces, cross sections of the multilayer absorbent body 140 are imaged by a microscope and measurement is performed from the cross sectional photograph or cross sectional images. The measurement sample of the multilayer absorbent body 140 is cut along the cross direction through tops of the raised ridge portions 2A and the groove portions 1A.

When height (length in the thickness direction) is measured, height is determined by measuring from the lowest point (surface of the table) of the multilayer absorbent body 140 to each highest point of the raised ridge portions 2A and the base of the groove portions 1A.

When pitch is measured, pitch of the raised ridge portions 2A is determined by measuring between tops of adjacent raised ridge portions 2A, and pitch of the groove portions 1A is determined by measuring between centers of adjacent groove portions 1A.

When width is measured, it is determined by measuring the maximum width from the lowest point (surface of the table) of the multilayer absorbent body 140 to the base of the raised ridge portion 2A and similarly, the maximum width of the base of the groove portion 1A is measured for determining width of the groove portions 1A.

The cross sectional shape of the raised ridge portions 2A is not particularly limited and may be in dome, trapezoidal, triangular, Ω-like and tetragonal shapes. It is preferable for sides and tops of the raised ridge portions 2A to be curved for improved texture when the absorbent body is used as a surface sheet of absorbent articles, for example. Moreover, in order to prevent raised ridge portions 2A from crushing under external pressure, or to retain the integrity of voids arising from groove portions 1A, it is preferable for the groove portions 1A to become narrower from the base to the top in width. Examples of preferable cross sectional shape include dome shape.

The cross section of the absorbent body (inner layer) 142 in the raised ridge portions 2A is not particularly limited and may be formed into a predefined shape as described above, and it is preferably having curved lines (curved surfaces) such as dome shape in order to prevent the absorbent body 142 from giving hard texture to users, for example.

Furthermore, making up the absorbent body 142 with hard fiber layers (fibers not easily crushed), for example, makes the raised ridge portions 2A unlikely to be crushed in the thickness direction.

The fibers 102 which make up the first fiber layer 141, for example, can be made to have more flexibility than an average flexibility of the fibers 101 and 102 which make up the multilayer absorbent body 140, and less flexibility than an average flexibility of the fibers 101 which make up the absorbent body 142. For example, flexibility of the fibers 101 which make up the absorbent body 142 can be adjusted to be less than the flexibility of the fibers 101 which make up the first fiber layer 141. The average flexibility of fibers is an average flexibility of the fibers 102 which make up the first fiber layer 141 and the fibers 101 which make up the absorbent body 142, for example.

Strength of cross points of the fibers 101 may vary partially in order to provide the fibers 102 which make up the first fiber layer 141 with high flexibility, for example. Specifically, the first fiber layer 141 can be adjusted so that joint strength is weakened, or not to form joints in all or part of the cross points between fibers which make up the first fiber layer 141.

For example, a plurality of fibers having different melting points of resin components may be combined in the surface of the fibers 102 in order to weaken joint strength or not to form joints in all or part of the cross points between fibers which make up the first fiber layer 141. For example, a fiber A containing a core-in-sheath structure of low-density polyethylene (melting point 110° C.) and polyethylene terephthalate and a fiber B containing a core-in-sheath structure of high-density polyethylene (melting point 135° C.) and polyethylene terephthalate may be mixed in a ratio of fiber A to fiber B of 70:30 to form a fiber web 100. When this fiber aggregate is heated in an oven, etc. at 120° C., fibers are heat-sealed because of the molten low-density polyethylene at cross points between fibers A or the fibers A and the fibers B in the fiber aggregate. The strength of cross points between fibers A becomes larger than the strength of cross points between fibers A and fibers B because large amount of low-density polyethylene is melted in cross points. In addition, heat sealing does not take place in cross points between fibers B because high-density polyethylene is not melted. Stated differently, fibers are heat-sealed so that the strength of cross points between fibers A is larger than the strength of cross points between fibers A and fibers B, and the strength of cross points between fibers A and fibers B is larger than the strength of cross points between fibers B. In this case, for example, if the absorbent body 142 is formed with a fiber having a melting point of 120° C. or less, strength of cross points between fibers in the absorbent body 142 can be increased more than the strength of cross points between fibers in the first fiber layer 141.

Fibers that are longer than an average fiber length of the multilayer absorbent body 140 can be used as the fibers 102 which make up the first fiber layer 141. In addition, fibers that are longer than the fibers 101 which make up the absorbent body 142 may be used as the fibers 102 which make up the first fiber layer 141. As the fiber length becomes greater, distances between fibers widen, and flexibility of the fibers is increases because fibers are unlikely to bump with each other.

Fibers that are shorter than an average fiber length of the multilayer absorbent body 140 can be used as the fibers 101 which make up the absorbent body 142. In addition, fibers that are shorter than the fibers 102 which make up the first fiber layer 141 may be used as the fibers 101 which make up the absorbent body 142. As the fiber length becomes less, distances between fibers narrows, and fiber density increases. This allows a density gradient to be built in the raised ridge portions 2A, and liquids such as menstrual blood can be transferred favorably to the absorbent body 142 even if a small amount of menstrual blood or sweat is attached to the tops of the raised ridge portions 2A. For example, fibers with a short fiber length containing a lot of pulp may be used.

The 3-dimensionally crimped fibers may be contained in the absorbent body 142, for example, for decreasing flexibility of the fibers 101 which make up the absorbent body 142. Examples of the 3-dimensional crimped shape include spiral shape, zigzag shape and Ω-like shape. If contained fibers are mostly oriented in a flat surface direction and partially oriented in the thickness direction, for example, the absorbent body is unlikely to be crushed by additional external pressure because buckling strength of the fiber itself works in the thickness direction.

Furthermore, it is preferable for the 3-dimensionally crimped fibers to have spiral shape because the second fiber layer 142 is likely to resume its original thickness after being freed from external pressure even if it is slightly crushed due to excessive external pressure because spiral shape is likely to resume its original shape after being freed from external pressure.

The 3-dimensionally crimped fiber can be formed by mechanical crimping and heat contraction.

Mechanical crimping forms 3-dimensionally crimped fibers from continuous and straight fibers by controlling the difference in circumferential velocity of line speed, heat and pressure after fiber spinning. As the number of crimping per unit length of crimped fibers increases, buckling strength under external pressure is increased. Specifically, number of crimping is selected from the range of 10 per inch to 35 per inch and in addition, from 15 per inch to 30 per inch.

For example, fibers made of two or more resins of different melting points are heated to form 3-dimensionally crimped fibers by heat contraction. Specifically, fibers designed to have different heat contraction percentage due to the difference in melting points are heated and crimped three dimensionally by the difference in heat contraction percentage. Examples of resin structure in the cross section of fibers include biased core type of core-in-sheath structure and side-by-side type with right and left components of different melting points. The heat contraction percentage of the above fibers is preferably in the range of 5% to 90% and more preferably in the range of 10% to 80%, for example.

The method for measuring heat contraction percentage is as follows. (1) A fiber web of 200 g/m² containing 100% of fiber is formed for measurement, (2) the fiber web is cut in a dimension of 250 mm×250 mm, (3) the cut sample is left unattended in an oven at 145° C. for 5 minutes for heating, (4) the length of the sample after contraction by heat is measured, and (5) heat contraction percentage is then calculated from the difference in lengths before and after heat contraction.

The content of 3-dimensionally crimped fibers in the absorbent body 142 is preferably 30% by weight or more and more preferably 50% by weight or more, for example. The content of 3-dimensionally crimped fibers is preferably 30% by weight or more because abilities to maintain shapes under compression and to recover shapes after compression are easily obtained for the absorbent body 142.

The 3-dimensionally crimped fibers may also be contained in the first fiber layer 141. The content of 3-dimensionally crimped fibers in the first fiber layer 141 is preferably 70% by weight or less, for example, and more preferably 50% by weight or less. The fiber density of the first fiber layer 141 can be decreased by containing 3-dimensionally crimped fibers as the fibers 102 which make up the first fiber layer 141. It is preferable because liquids are appropriately transferred from the first fiber layer 141 to the absorbent body 142. And 70% by weight or less content of 3-dimensionally crimped fibers in the first fiber layer 141 can protect skin from feeling a foreign body sensation while in contact with an edge (cut edge) of the 3-dimensionally crimped fibers.

Fibers with a Young's modulus higher than that of the fibers 102 which make up the first fiber layer 141 may be used as the fibers 101 which make up the absorbent body 142.

Fibers with a high fiber ratio may be used as the fibers 101 which make up the absorbent body 142 as the fibers with a high Young's modulus. For example, the fibers with a fiber ratio greater than the fiber ratio of the fibers 102 which make up the first fiber layer 141 may be used.

For example, fibers 101 with a low average content of inorganic matters may be used as the fibers 101 which make up the absorbent body 142. For example, fibers 102 with a lower average content of inorganic matters than that of the fibers which make up the first fiber layer 141 may be used. Examples of inorganic matters include inorganic fillers such as titanic oxide.

The absorbent body 142 can be formed by using fibers with a shorter fiber length than that of fibers which make up the first fiber layer 141 by air-laid method. The air-laid method is preferably performed when the absorbent body 142 is formed by layering the fibers 101 with a short fiber length in a predefined thickness.

When the fibers with a short fiber length are layered by air-laid method, fibers are likely to be oriented toward the thickness direction of the fiber layer. When the absorbent body (inner layer) 142 is formed by air-laid method for controlling fibers to be oriented toward the thickness direction, for example, liquids such as menstrual blood migrated to the absorbent body (inner layer) 142 can be prevented from dispersing in a flat surface direction of the surface of the multilayer absorbent body 140 because liquids such as menstrual blood are likely to be migrated along the fiber orientation. Moreover, it is preferable for the fibers in the absorbent body (inner layer) 142 to be oriented in the thickness direction because raised ridge portions are not likely to be crushed even under additional external pressure due to increased buckling strength.

1-3-2. Fiber Orientation, Density or Fiber Basis Weight 1-3-2-1. Fiber Orientation The fibers 101 and 102 which make up the base of the groove portions 1A are oriented approximately in the width direction (machine direction) as shown in FIG. 16. The fibers 101 and 102 in the first fiber layer 141 and the absorbent body 142 are wholly oriented in the width direction (cross direction). Each of the orientation of the fibers 102 in the first fiber layer 141 and the orientation of the fibers 101 in the absorbent body 142 can be adjusted respectively by controlling flexibilities or characteristics of the fibers 101 and 102 which make up the first fiber layer 141 and the absorbent body 142, or by controlling the intensity of the ejected fluid. For example, ratio of the fibers 102 oriented in the width direction of the first fiber layer 141 and ratio of the fibers 101 oriented in the width direction of the absorbent body 142 may be adjusted to be different.

The fibers 101 and 102 on the sides of the raised ridge portions 2A are oriented along the length direction (machine direction) of the raised ridge portions 2A. For example, the fibers 101 and 102 on the sides of the raised ridge portions 2A are oriented toward length direction as compared to the orientation of the fibers 101 and 102 in the center (areas between both sides) of the raised ridge portions 2A.

The content per unit area of the fibers oriented toward width direction of the absorbent body is greater in the areas which make up the base of the groove portions 1A than that of the center portions 9. The content per unit area of the fibers oriented toward the longitudinal direction of the absorbent body is greater in the side portions 8 than that of the center portions 9. And more amount of the fibers 101 and 102 oriented toward width direction is contained in the center portions 9 than in the areas which make up the base of the groove portions 1A or side portions 8. For this reason, even if the thickness of the raised ridge portions 2 is decreases due to load given to the center portions 9, for example, when the load is released, the raised ridge portions 2 are likely to resume their original height because of rigidity of the fibers 101 and 102 oriented in the thickness direction. More specifically, it is possible to form a nonwoven fabric having high ability to recover from compression.

1-3-2-2. Fiber Density

The areas which make up the base of the groove portions 1A as shown in FIG. 16 are adjusted to have densities of the fibers 101 and 102 less than that of the raised ridge portions 2A. The fiber density of the areas which make up the base of the groove portions 1A may be adjusted voluntarily by various conditions such as volume of the fluid consisting mainly of gaseous matter (hot air, for example) or tension.

The raised ridge portions 2A are adjusted to have densities of the fibers 101 and 102 greater than that of the areas which make up the base of the groove portions 1A as described above. The fiber density of the raised ridge portions 2A may be adjusted voluntarily by various conditions such as volume of the fluid consisting mainly of gaseous matter (hot air, for example) or tension.

1-3-2-3. Fiber Basis Weight

The areas which make up the base of the groove portions 1A as shown in FIG. 16 are adjusted to have a fiber basis weight of the fibers 101 and 102 less than that of the raised ridge portions 2A. In addition, the fiber basis weight of the areas which make up the base of the groove portions 1A is adjusted to be less than an average fiber basis weight of entire absorbent body including the groove portions 1A and the raised ridge portions 2A.

The raised ridge portions 2A are adjusted to have a fiber basis weight of the fibers 101 and 102 that is greater than that of the areas which make up the base of the groove portions 1A as described above.

The fiber basis weight of the entire multilayer absorbent body 140 is preferably 10 g/m² to 200 g/m² and more preferably 20 g/m² to 100 g/m². When the fiber basis weight of the entire multilayer absorbent body 140 is less than 10 g/m², the absorbent body may be damaged easily during use as a surface sheet as well as an absorbent body for absorbent articles such as sanitary napkins that are attached to the body, for example. When the fiber basis weight of entire multilayer absorbent body 140 is greater than 200 g/m², liquids may become less likely to be transferred downward smoothly if other absorbent body are disposed further down.

The fiber basis weight of the areas which make up the base of the groove portions 1A relative to the fiber basis weight of the raised ridge portions 2A is preferably 90% or less, more preferably 3% to 90% and most preferably 30% to 70%. When the fiber basis weight of the areas which make up the base of groove portions 1A relative to the fiber basis weight of the raised ridge portions 2A is greater than 90%, resistance against the liquid such as menstrual blood fed into the groove portions 1A is increased as it is transferred downward (opposite of the side where the liquid is fed), and the liquid may overflow from the groove portions 2A. When the fiber basis weight of the areas which make up the base of groove portions 1A relative to the fiber basis weight of the raised ridge portions 2A is less than 3%, strength of the multilayer absorbent body 140 is weakened making it unsuitable for a specific use. If the multilayer absorbent body 140 is used as a surface sheet of absorbent articles such as sanitary napkins, for example, the surface sheet may be damaged easily during use of the absorbent articles.

The fiber basis weight of the raised ridge portions 2A is preferably 15 g/m² to 250 g/m², for example, and more preferably 25 g/m² to 120 g/m². The fiber density of the raised ridge portions 2A is preferably 0.20 g/cm³ or less, more preferably 0.005 g/cm³ to 0.20 g/cm³ and most prefer ably 0.007 g/cm³ to 0.07 g/cm³.

When the fiber basis weight of the raised ridge portions 2A is less than 15 g/m², or when the density is less than 0.005 g/cm³ the raised ridge portions 2A may be likely to be crushed due to weight of the liquid such as menstrual blood or external pressure. Furthermore, blood once absorbed may reverse its course under additional pressure.

When the fiber basis weight of the raised ridge portions 2A is more than 250 g/m², or when the density is more than 0.20 g/cm³, menstrual blood discharged into the raised ridge portions 2A may be unlikely to be transferred downward and are collected in the raised ridge portions 2A.

The fiber basis weight of the areas which make up the base of the groove portions 1A is preferably 3 g/m² to 150 g/m², for example and more preferably 5 g/m² to 80 g/m². The fiber density of the areas which make up the base of the groove portions 1A is preferably 0.18 g/cm³ or less, more preferably 0.002 g/cm³ to 0.18 g/cm³ and most preferably 0.005 g/cm³ to 0.05 g/cm³.

When the fiber basis weight of the areas which make up the base of the groove portions 1A is less than 3 g/m², or when the density is less than 0.002 g/cm³, and if the multilayer absorbent body 140 is used as a surface sheet as well as an absorbent body, the multilayer absorbent body 140 may be damaged easily during use of the absorbent articles in which the multilayer absorbent body 140 is disposed as a surface sheet of the absorbent articles such as sanitary napkins, for example, as described above.

On the other hand, when the fiber basis weight of the areas which make up the base of the groove portions 1A is greater than 150 g/m², or when the density is greater than 0.18 g/cm³, liquids such as menstrual blood fed into the groove portions 1A may be collected in the groove portions 1A. In this case, liquids may overflow from the groove portions 1A.

The ratio of fiber basis weight of the first fiber layer 141 to fiber basis weight of the absorbent body 142 is preferably in the range of 10:90 to 90:10 and more preferably in the range of 20:80 to 50:50. When the multilayer absorbent body 140 is used as a surface sheet of absorbent articles such as sanitary napkins and also used as a surface sheet as well as an absorbent body, the first fiber layer may be damaged and the absorbent body may fall out if the fiber basis weight of the first fiber layer 141 is less than 10% of the fiber basis weight of the multilayer absorbent body 140. Reversely, when the fiber basis weight of the first fiber layer 141 is greater than 90% of the fiber basis weight of the multilayer absorbent body 140, absorbent capacity is low allowing even a small amount of excretory substance to leak.

When the groove portions 1A and the raised ridge portions 2A satisfy the above condition, it is possible to prevent menstrual blood from dispersing on the surface of the multilayer absorbent body 140 even if a large amount of menstrual blood is discharged or menstrual blood of high viscosity is discharged onto the multilayer absorbent body 140, for example. For example, if an external pressure is added to the multilayer absorbent body 140 slightly crushing the raised ridge portions 2A, voids are likely to be maintained by the groove portions (valleys) 1A and menstrual blood discharged in this condition may be prevented from dispersing broadly on the surface. Furthermore, even when menstrual blood once absorbed reverses its course under external pressure, contact area with the skin is small and menstrual blood can be prevented from broadly reattaching to the skin.

The fiber basis weight of the raised ridge portions 2A is adjusted to be high for increasing the number of fibers to thereby increase the number of sealed points to maintain porous structure.

When the multilayer absorbent body 140 in the third embodiment is used for absorbent articles such as sanitary napkins, there is no actual space between the first fiber layer 141 as a surface sheet and the absorbent body 142 because the first fiber layer 141 as a surface sheet and the absorbent body 142 are formed simultaneously. This allows migration of menstrual blood, etc. to be performed effectively from the surface layer of the absorbent article to the absorbent body. The same can be stated for the absorbent body in the fourth and fifth embodiments and absorbent articles, which will be described later.

1-3-3 Manufacturing Method

The method for manufacturing the multilayer absorbent body 140 in the third embodiment will be explained below. First, a fiber web 100 as a multilayer fiber aggregate (not shown) containing a first fiber aggregate (not shown), which is an almost sheet-like fiber aggregate made of fibers with flexibility, and a fiber aggregate for absorbent body (not shown), which is a sheet-like fiber aggregate containing absorbent fibers with flexibility layered and disposed on the first side of the first fiber aggregate, is disposed on an upper side of the net-like support member 210 as a breathable support member. Stated differently, the fiber web 100 is supported by the net-like support member 210 from beneath. Meanwhile, predefined fibers may be layered and disposed on a predefined surface of the net-like support member 210 to form the above multilayer fiber aggregate.

The net-like support member 210 supporting the fiber web 100 is conveyed in the machine direction. A gaseous matter is then ejected continuously to the upper side of the fiber web 100 being conveyed to form a multilayer absorbent body 140 in the third embodiment.

The multilayer absorbent body 140 in the third embodiment can be manufactured by means of the above absorbent body manufacturing apparatus 90. The method for manufacturing the absorbent body by means of the absorbent body manufacturing apparatus 90 can be referred to the above description.

1-4. Fourth Embodiment

A multilayer absorbent body 150 in the fourth embodiment will be explained referring to FIG. 17. The multilayer absorbent body 150 is a multilayer absorbent body in which a plurality of openings 3A are formed in the base of the groove portions 1A, which are the low fiber basis weight regions of the multilayer absorbent body 140 in the third embodiment, at regular intervals.

Even though the openings 3A, which are the low fiber basis weight regions, are formed in the base of the groove portions 1A of the multilayer absorbent body 150, depressed portions formed so that the thickness of the multilayer absorbent body 150 in the groove portions 1A is decreased may be formed instead of the openings 3A. Moreover, the openings 3A also include openings that are not opened completely in the thickness direction (only a part of the openings 3A is opened).

The base of the groove portions 1A in the multilayer absorbent body 150 varies in height along the formed direction of the groove portions 1A. The low fiber basis weight regions such as the groove portions 1A are preferably formed continuously at prescribed intervals in the formed direction of the groove portions 1A while having various heights along the formed direction of the groove portions 1A for preventing flow of liquids such as menstrual blood along the groove portions 1A.

Figure 17:
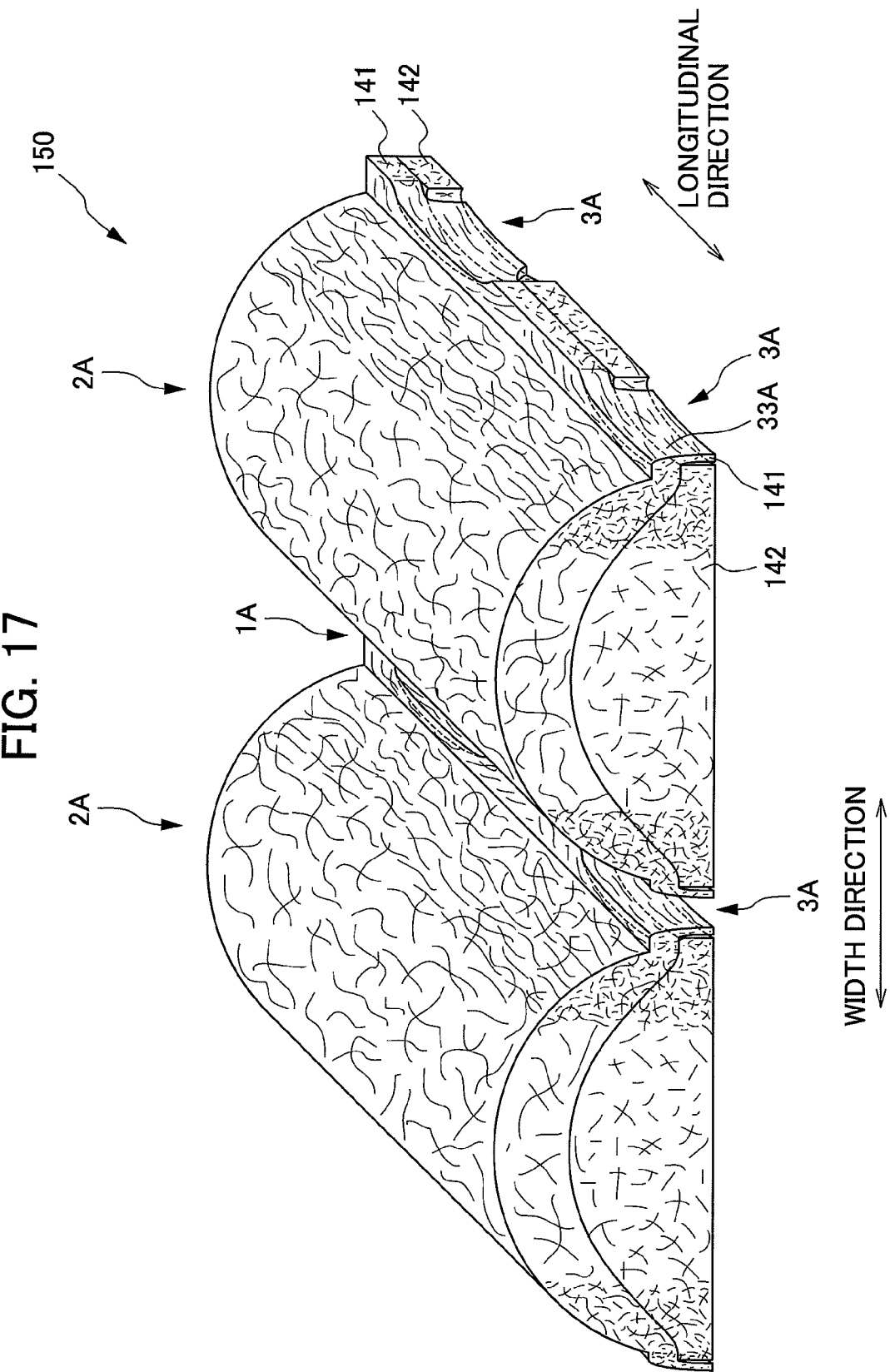
FIG. 17 shows a perspective cross section of a multilayer absorbent body in the fourth embodiment.
Figure 18:
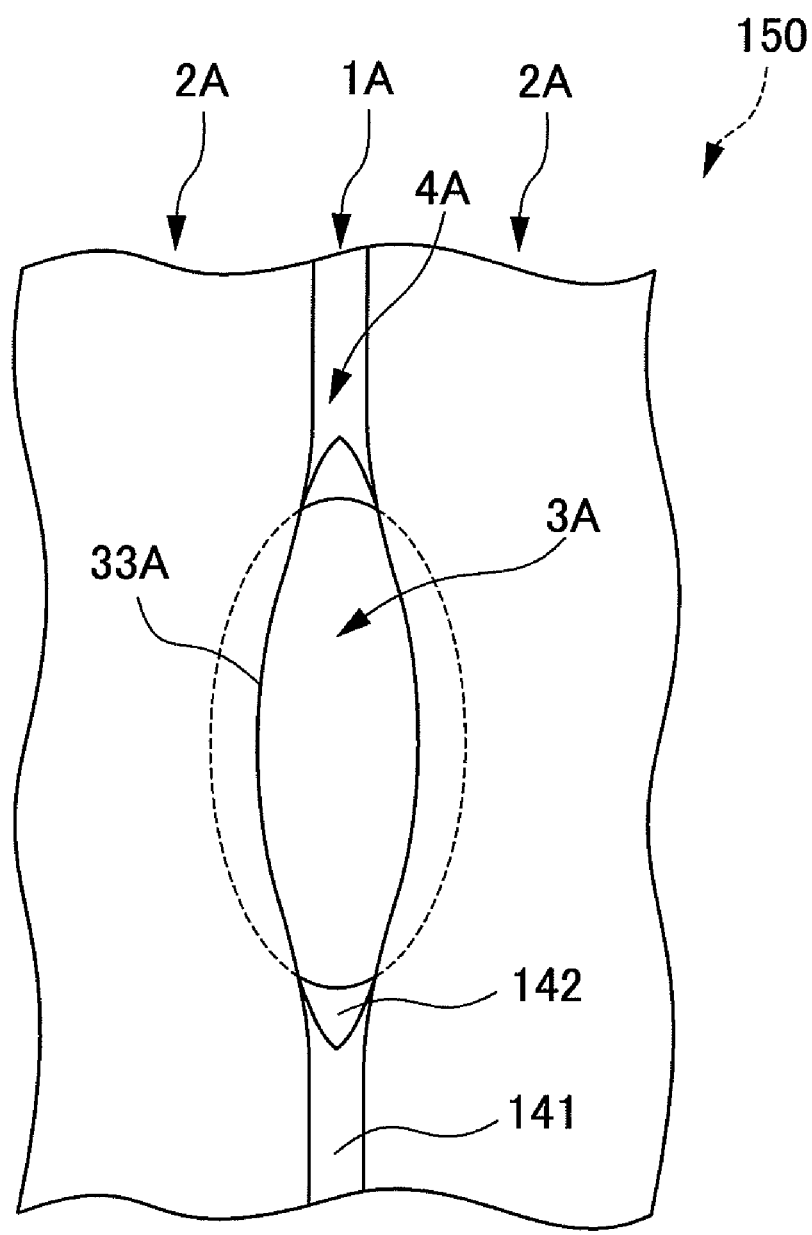
FIG. 18 shows a view for explaining a structure around an opening of the multilayer absorbent body in the fourth embodiment.

As shown in FIGS. 17 and 18, all or part of sidewall portions 33A which make up the peripheral border of each of the openings 3A are covered by part of the first fiber layer 141.

The sidewall portions 33A on both sides of the openings 3A in relation to the extended direction (machine direction) of the groove portions 1A are covered by the first fiber layer 141, for example, and the sidewall portions 33A on edges of the openings 3A in relation to the extended direction (machine direction) of the groove portions 1A are not covered by the first fiber layer 141. And the absorbent body 142 disposed in lower layers is exposed in the areas of the sidewall portions 33A that are not covered by the first fiber layer 141.

As shown in FIG. 18, the base of the groove portions 1A where the openings 3A are not formed contains the areas consist of the first fiber layer 141 and the areas consist of the absorbent body 142. Specifically, there are areas not covered by the first fiber layer 141 around the edges of peripheral borders of the openings 3A in the groove portions 1A in relation to the extended direction (machine direction) of the groove portions 1A. The absorbent body 142 is exposed in the above areas.

A plurality of groove portions are formed in the first fiber layer 141 as well as a plurality of openings formed in the areas corresponding to the openings 3A of the multilayer absorbent body 150. These openings are formed in shape of oval in relation to the extended direction (machine direction) of the groove portions 1A, more oblong than the openings 3A in the multilayer absorbent body 150.

When the multilayer absorbent body 150 in the fourth embodiment is used for absorbent articles such as sanitary napkins, etc., controlling degradation of absorbability or improving compatibility with the body can be achieved as similar to the above absorbent body 120 in the second embodiment.

Furthermore, when the first fiber layer 141 consists mainly of synthesized fibers and the absorbent body 142 consists mainly of absorbent fibers, liquids such as menstrual blood, etc. fed into the depressed portions (not shown) and/or openings 3A are not likely to be absorbed by both sides of the sidewall portions 33A of the depressed portions and/or openings 3A in relation to the machine direction. Stated differently, liquids such as menstrual blood, etc. fed into the depressed portions (not shown) and/or openings 3A are not likely to be migrated from both sides of the sidewall portions 33A in relation to the machine direction to the absorbent fibers of the absorbent body 142 because all or part of the sidewall portions 33A, which make up the peripheral borders of the depressed portions (not shown) and/or openings 3A formed in the areas which make up the base of the groove portions 1A as the low fiber basis weight regions, are covered by the first fiber layer 141. The liquid such as menstrual blood are then migrated from the edges of the groove portions 1A in relation to the direction toward which the groove portions 1A are formed continuously (machine direction) to the absorbent fibers of the absorbent body 142. This can further prevent liquids such as menstrual blood from being absorbed in the width direction.

1-5. Fifth Embodiment

Figure 19:
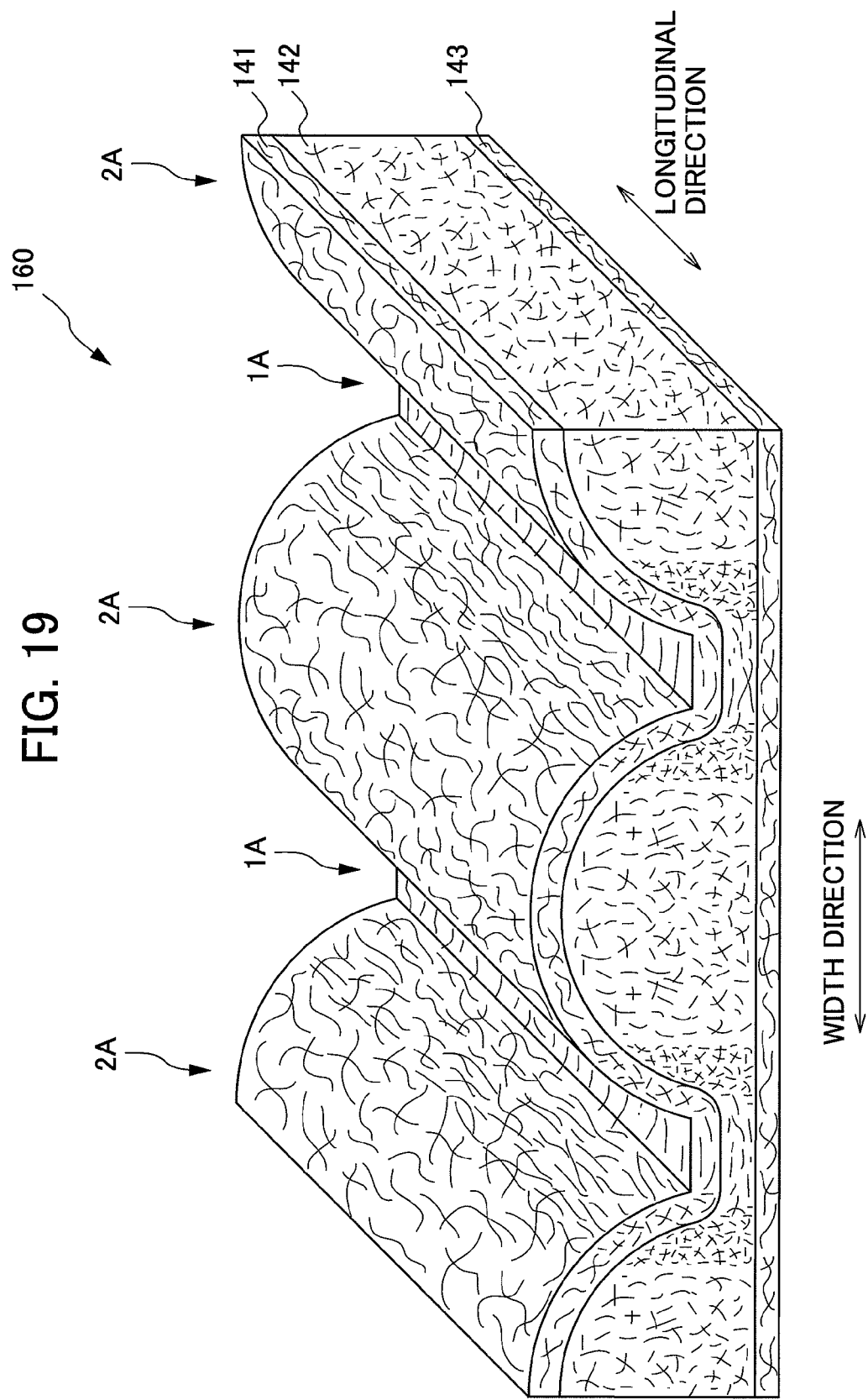
FIG. 19 shows a perspective cross section of a multilayer absorbent body in the fifth embodiment.

A multilayer absorbent body 160 in the fifth embodiment will be explained referring to FIG. 19. The multilayer absorbent body 160 is a multilayer absorbent body in which a second fiber layer is further disposed in the multilayer absorbent body 140 in the third embodiment. It is the multilayer absorbent body in which a second fiber layer 143 is further disposed on a surface opposite of the first fiber layer 141 side of the absorbent body 142 in the multilayer absorbent body 140 in the third embodiment.

The first fiber layer 141 is preferably layered and formed by card method. The absorbent body 142 is preferably formed by layering fibers which make up the absorbent body 142 on the first side of the first fiber layer 141 by air-laid method.

The second fiber layer 143 is preferably layered and formed by card method. It is possible to provide predefined functions or strength by further disposing the second fiber layer 143. For example, disposing the second fiber layer 143 can enhance an ability to maintain shapes or cushioning properties, for example.

The method for manufacturing the multilayer absorbent body 160 in the fifth embodiment will be explained below. First, a multilayer fiber web containing a first fiber web, which is a sheet-like fiber web made of fibers with flexibility, a fiber web for absorbent body, which is an almost sheet-like fiber web containing absorbent fibers with flexibility layered and disposed on the first side of the first fiber web, and a second fiber web, which is an almost sheet-like fiber web containing fibers with flexibility disposed on a side opposite of the first fiber layer in the fiber web for absorbent body, is disposed on a predefined surface of the net-like support member 210 as shown in FIG. 4 to be supported by the net-like support member 210 from the first side of the multilayer fiber aggregate.

The multilayer fiber aggregate supported by the net-like support member 210 is conveyed in a specified direction (machine direction) by means of a predefined conveying unit. A fluid consisting mainly of gaseous matter is then ejected to the second side of the multilayer fiber aggregate being conveyed in a specified direction by means of an ejection unit, for example.

The fiber web for absorbent body is formed by disposing the second fiber web on a predefined surface of the net-like support member 210, and layering fibers containing absorbent fibers which make up the fiber web for absorbent body on a side opposite of the net-like support member 210 side of the second fiber web. The multilayer fiber web is then formed by layering and disposing the first fiber web on a side opposite of the second fiber web side of the formed fiber web for absorbent body. The fiber web for absorbent body is formed on a predefined surface of the second fiber aggregate by air-laid method, for example.

1-6. Sixth Embodiment

An absorbent body 111 in the sixth embodiment will be explained referring to FIG. 20. The absorbent body 111 is an absorbent body 110 in the first embodiment further containing a absorbent polymer 103.

Figure 20:
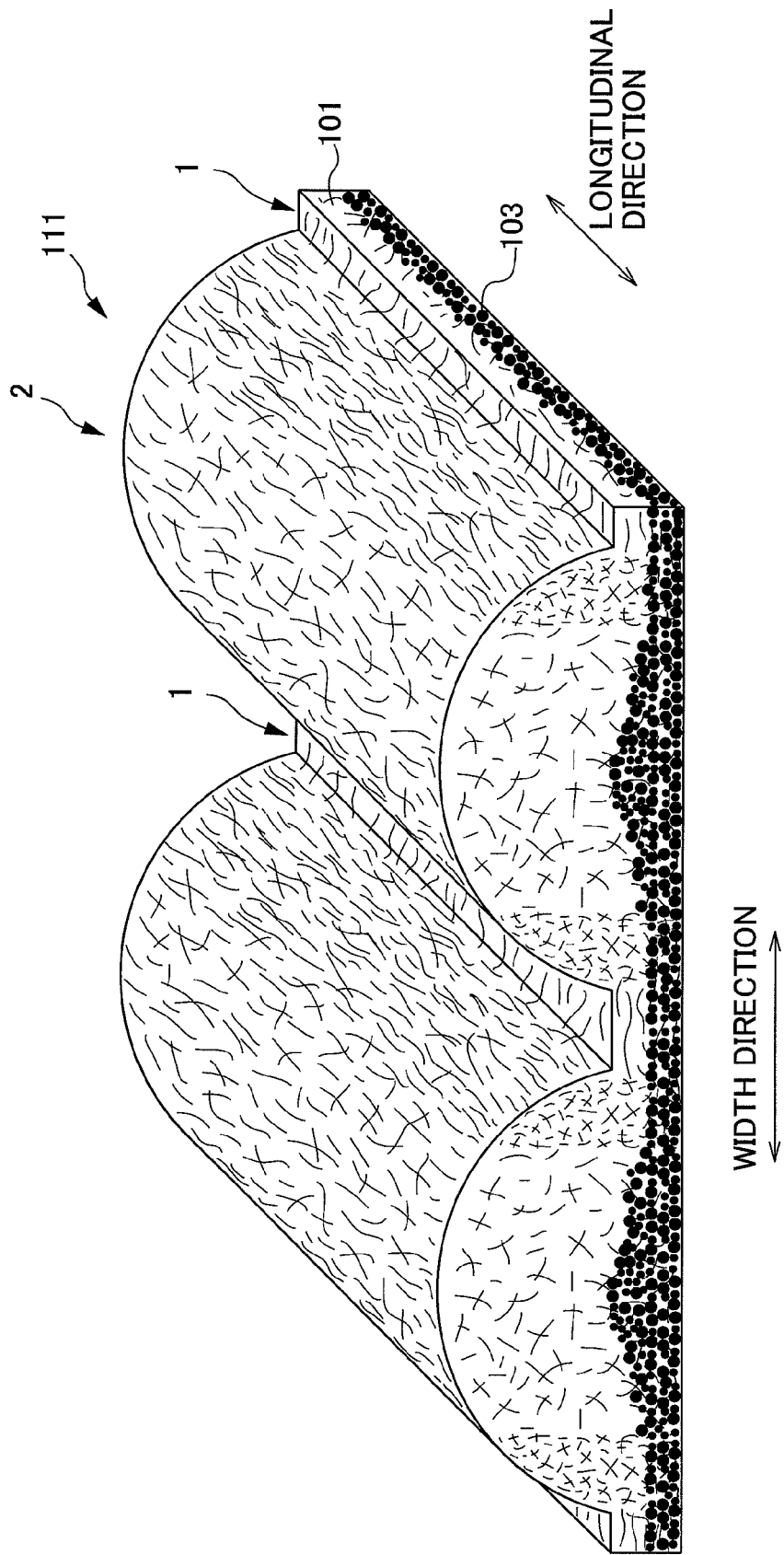
FIG. 20 shows a perspective cross section of an absorbent body in the sixth embodiment.

As shown in FIG. 20, the absorbent polymer 103 is disposed disproportionately on a side opposite of the side on which the areas which make up the base of the groove portions 1 as the low fiber basis weight regions, and the raised ridge portions 2 as the high fiber basis weight regions, are formed. The absorbent polymer 103 is contained as mixed with the fibers 101 which make up the absorbent body 111. The shape of the absorbent polymer 103 is not particularly limited and may be powdery, granular or fibrous in shape.

The absorbent body 111 in the sixth embodiment can be obtained by ejecting a fluid consisting mainly of gaseous matter to the first side of the fiber web 100 formed by mixing the fibers 101 containing absorbent fibers and the absorbent polymer 103. The groove portions 1 and the raised ridge portions 2 can be formed on the first side of the fiber web 100 by ejecting the fluid consisting mainly of gaseous matter while the absorbent polymer 103 is displaced to the second side.

When the absorbent body 111 is manufactured by the above method, the absorbent polymer 103 is preferably fibrous, for example, so that the absorbent polymer 103 is not blown off outside of the absorbent body 111 by the fluid consisting mainly of gaseous matter.

If liquids (menstrual blood, for example) are dripped continuously or on and off on the side where the groove portions 1 and the raised ridge portions 2 of the absorbent body 111 in the sixth embodiment are formed, the liquids are first absorbed by the absorbent fiber. And the liquids not absorbed by the absorbent fiber are absorbed by the absorbent polymer 103. Meanwhile, since the absorbent polymer 103 is disposed disproportionately on a side opposite of the side on which the groove portions 1 and the raised ridge portions 2 are formed, shapes of the groove portions 1 and the raised ridge portions 2 are not likely to be crushed even if the absorbent polymer 103 is expanded due to absorption of liquid.

1-7. Seventh Embodiment

An absorbent body 112 in the seventh embodiment will be explained referring to FIG. 21. The absorbent body 112 is an absorbent body in which the absorbent polymer 103 is disposed in the groove portions 1 of the absorbent body 110 in the first embodiment.

Figure 21:
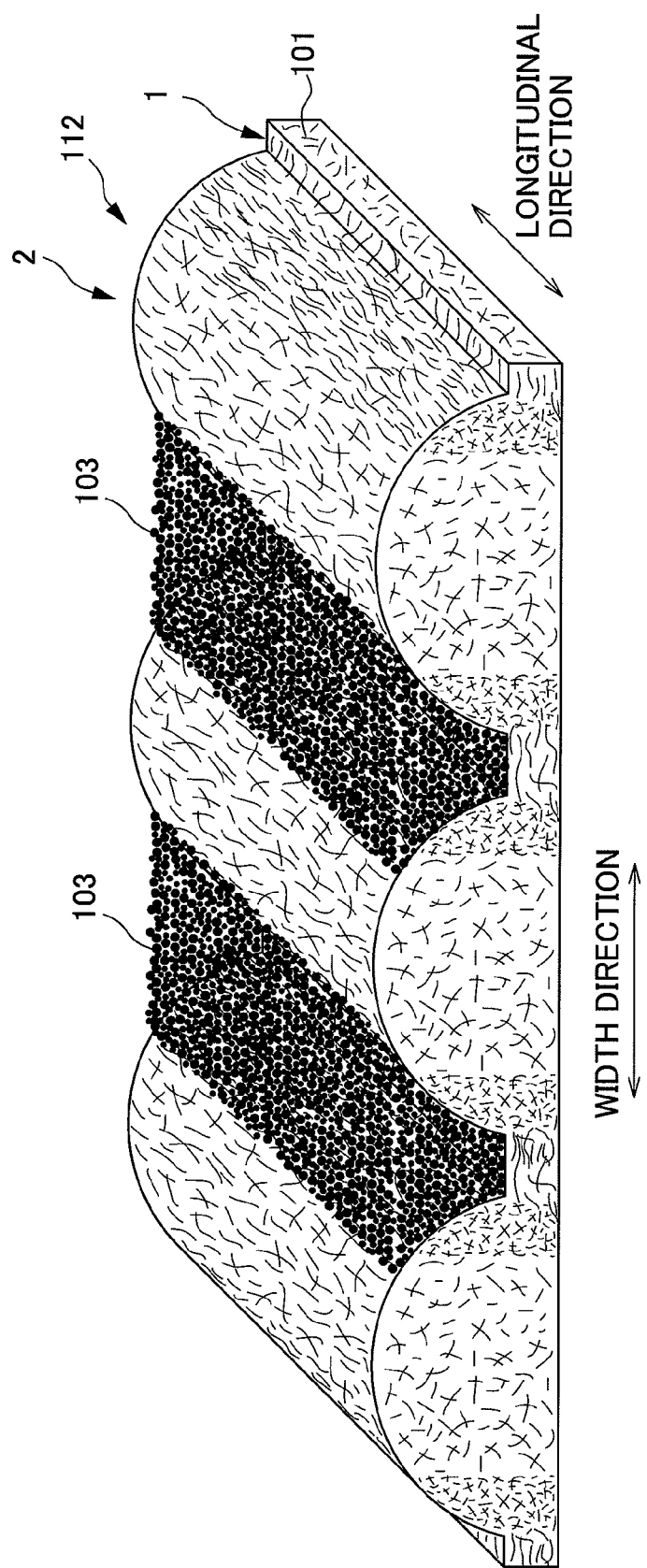
FIG. 21 shows a perspective cross section of an absorbent body in the seventh embodiment.

As shown in FIG. 21, the absorbent polymer 103 is disposed on the groove portions 1 of the absorbent body 112 in the seventh embodiment. Specifically, the absorbent polymer is disposed as filling in the hollow of the groove portions 1. By doing this, tops of the raised ridge portions 2 and the absorbent polymer 103 are exposed on upper side of the absorbent body 112. The absorbent body 112 in the seventh embodiment can be obtained by filling the absorbent polymer 103 in the hollow of the groove portions 1 of the absorbent body 110 in the first embodiment.

If liquids (menstrual blood, for example) are dripped continuously or on and off on the side where the groove portions 1 and the raised ridge portions 2 of the absorbent body 112 in the seventh embodiment are formed, the liquids dripped in the raised ridge portions 2 are absorbed by the absorbent fiber, and the liquids dripped in the absorbent polymer 103 are absorbed directly by the absorbent polymer 103.

1-8. Eighth Embodiment

An absorbent body 113 in the eighth embodiment will be explained referring to FIG. 22. The absorbent body 113 is an absorbent body in which the absorbent body 110 in the first embodiment is layered and disposed on the upper side of the absorbent body 112 in the seventh embodiment so that the groove portions 1, etc. are facing the absorbent body 112.

Figure 22:
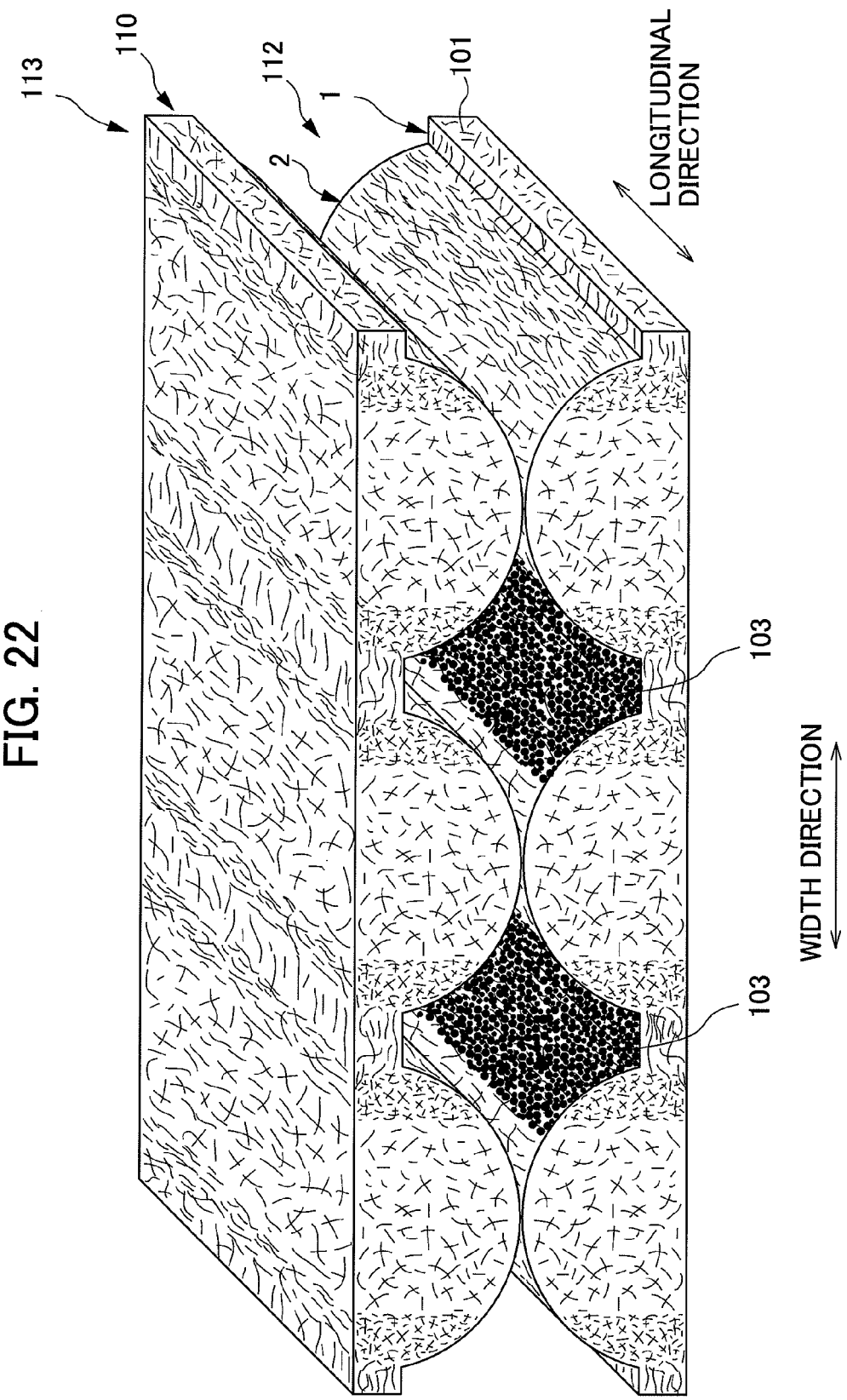
FIG. 22 shows a perspective cross section of an absorbent body in the eighth embodiment.

As shown in FIG. 22, the absorbent polymer 103 is disposed so as to fill the space between the layered absorbent body 112 and the absorbent body 110 in the absorbent body 113 in the eighth embodiment. Specifically, the absorbent body 113 can be obtained by layering and disposing the surface on which the groove portions 1 and the raised ridge portions 2 of the absorbent body 112 are formed and the surface on which the groove portions 1 and the raised ridge portions 2 of the absorbent body 110 are formed so that the tops of each raised ridge portion 2 face one another. The absorbent polymer 103 is then disposed in an area where the groove portions 1 of the absorbent body 112 and the groove portions 1 of the absorbent body 110 face one another in the absorbent body 113.

If liquids (menstrual blood, for example) are dripped continuously or on and off on the first side of the absorbent body 113 in the eighth embodiment, the liquids are first absorbed by the absorbent fiber, and the liquids not absorbed by the absorbent fiber are absorbed by the absorbent polymer 103. Since the absorbent polymer 103 are contained in the absorbent body 113 with an expandable space, the liquids are not leaked outside even if the absorbent polymer 103 expands due to absorption of liquids, and therefore the entire shape of the absorbent body 113 is not deformed significantly.

1-9. Fiber Structure

The fiber structure of the first fiber layer, the second fiber layer and the absorbent body in the above embodiments will be exemplified as follows.

The first fiber layer is exemplified by a blended fiber layer containing a fiber A coated with hydrophilic and lipophilic agents having a core-in-sheath structure of low-density polyethylene (melting point: 110° C.) and polyethylene terephthalate, an average fineness of 3.3 dtex and an average fiber length of 51 mm, and a fiber B coated with water and oil repellent agents having a core-in-sheath structure of high-density polyethylene (melting point: 135° C.) and polyethylene terephthalate, an average fineness of 3.3 dtex and an average fiber length of 51 mm. The mixing ratio of the fiber A and the fiber B is 70:30, and the fiber basis weight is adjusted to 15 g/m². The absorbent body is made with 100% crushed pulp and has a fiber basis weight of 100 g/m². The first fiber layer is opened by card method, and the absorbent body is opened by air-laid method. The second fiber layer can be exemplified by a fiber layer made with 100% fiber coated with hydrophilic and lipophilic agents having a core-in-sheath structure of high-density polyethylene and polyethylene terephthalate, an average fineness of 4.4 dtex and an average fiber length of 38 mm. The fiber basis weight of the fiber layer is 25 g/m².

The first fiber layer can be exemplified by a fiber layer made with 100% fiber coated with hydrophilic and lipophilic agents having a core-in-sheath structure of high-density polyethylene (melting point: 135° C.) and polyethylene terephthalate, an average fineness of 2.2 dtex, an average fiber length of 51 mm, 2% by weight of titanic oxide blended in the core and 3% by weight of titanic oxide blended in the sheath relative to each weight. The fiber basis weight of the fiber layer is 20 g/m². The absorbent body can be exemplified by a fiber layer containing a fiber C coated with hydrophilic and lipophilic agents having a core-in-sheath structure of biased core type of high-density polyethylene and polyethylene terephthalate, an average fineness of 5.6 dtex, an average fiber length of 51 mm and 1% by weight of titanic oxide blended relative to the weight of the core, and a fiber D of rayon having an average fineness of 3.3 dtex and an average fiber length of 45 mm. The mixing ratio of the fiber C and the fiber D is 50:50, and the fiber basis weight is 100 g/m². The second fiber layer can be exemplified by a fiber layer made with 100% fiber coated with hydrophilic and lipophilic agents having a core-in-sheath structure of high-density polyethylene and polyethylene terephthalate, an average fineness of 2.2 dtex and an average fiber length of 38 mm. The fiber basis weight of the second fiber layer is 20 g/m². Both of the first fiber layer and the second fiber layer are opened by card method.

The fiber structure of each fiber layer in the multilayer absorbent body in which the first fiber layer consist of a fiber aggregate by card method, the absorbent body consist of a fiber aggregate by air-laid method and the second fiber layer consist of a fiber aggregate by card method will be exemplified as follows.

The first fiber layer can be exemplified by a fiber layer made with 100% fiber coated with hydrophilic and lipophilic agents having a core-in-sheath structure of high-density polyethylene and polyethylene terephthalate, an average fineness of 3.3 dtex, an average fiber length of 51 mm, 1% by weight of titanic oxide blended in the core and 2% by weight of titanic oxide blended in the sheath relative to each weight. The fiber layer is formed by card method so as to have a fiber basis weight of 15 g/m².

The absorbent body can be exemplified by a fiber layer layered and formed by air-laid method by mixing crushed pulp and 10% by weight of the absorbent polymer in powdery form relative to the crush pulp so as to have a fiber basis weight of 110 g/m².

The second fiber layer can be exemplified by a fiber layer containing a fiber C and a fiber D of rayon having an average fineness of 3.3 dtex and an average fiber length of 45 mm. The fiber layer is layered and formed by card method so as to have a fiber basis weight of 20 g/m² with a mixing ratio of the fiber C and the fiber D being 50:50.

2. Absorbent Article

Figure 23:
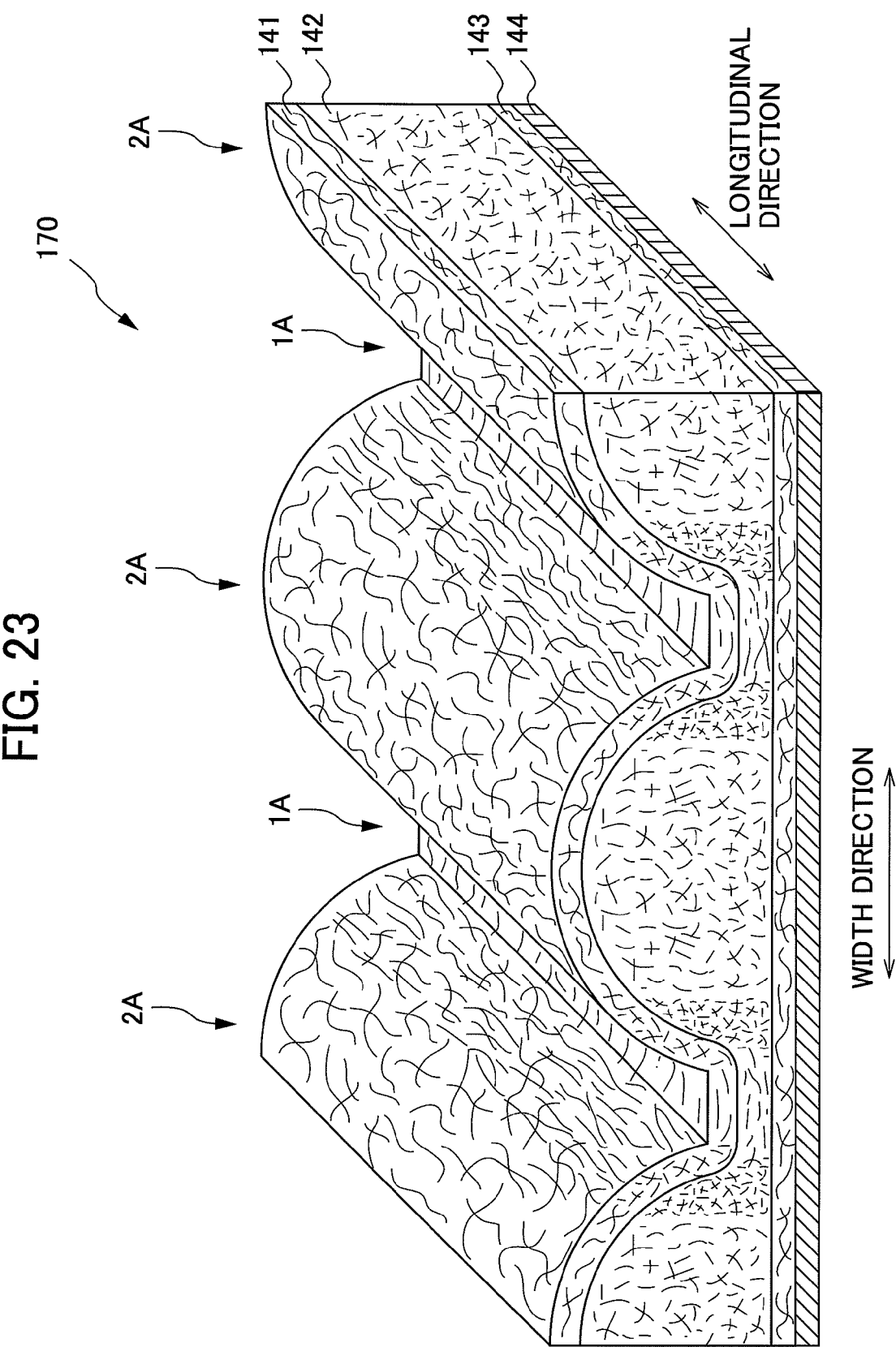
FIG. 23 shows a perspective cross section of an absorbent article of the present invention.

An absorbent article 170 will be explained referring to FIG. 23. The absorbent article 170 is equipped with a first fiber layer 141, an absorbent body 142 layered and disposed on the first side of the first fiber layer 141 and a liquid-impermeable sheet 144 disposed on a side of the absorbent body 142 opposite of the first fiber layer 141. In addition, a second fiber layer 143 is disposed in between the absorbent body 142 and the liquid-impermeable sheet 144.

A plurality of groove portions 1A depressed in the thickness direction of the absorbent article 170, and a plurality of raised ridge portions 2A, which are raised in the thickness direction and lie adjacent to each of the groove portions 1A with a fiber basis weight that is greater than the fiber basis weight of the areas which make up the base of the groove portions 1A, are formed on the second side of the first fiber layer 141.

The first fiber layer 141 and the absorbent body 142 are layered and disposed respectively in the groove portions 1A and the raised ridge portions 2A. The first fiber layer 141 side of the absorbent body 142 in the raised ridge portions 2A are raised on the same side as the second side of the first fiber layer 141 in the absorbent article 170.

The content of fibers oriented toward the longitudinal direction of the absorbent body in each of the raised ridge portions 2A (particularly sides thereof) is greater than the content of fibers oriented toward width direction of the absorbent body. The content of fibers oriented toward width direction of the absorbent body in the areas which make up the base of the groove portions 1A in each of the groove portions 1A is greater than the content of fibers oriented toward the longitudinal direction of the absorbent body.

A plurality of depressed portions (not shown) and/or openings may be formed in each of the groove portions 1A at predefined intervals. All or part of sidewall portions which make up the peripheral borders of each of the depressed portions and/or openings are covered by the first fiber layer 141.

The absorbent article of the present invention can be obtained, for example, by disposing a liquid-impermeable sheet on a predefined surface of the absorbent article or multilayer absorbent body in the above embodiments as described above. In particular, it is preferable to dispose a liquid-impermeable sheet on a predefined surface of the multilayer absorbent body in the above third to fifth embodiments for easily obtaining the absorbent article of the present invention.

3. Example

3-1. Example 1

<Fiber Structure>

A blended fiber layer containing a fiber A coated with hydrophilic and lipophilic agents having a core-in-sheath structure of low-density polyethylene (melting point: 110° C.) and polyethylene terephthalate, an average fineness of 3.3 dtex and an average fiber length of 51 mm, and a fiber B coated with water and oil repellent agents having a core-in-sheath structure of high-density polyethylene (melting point: 135° C.) and polyethylene terephthalate, an average fineness of 3.3 dtex and an average fiber length of 51 mm are used as a first fiber layer. The mixing ratio of the fiber A and the fiber B is 70:30 and the fiber layer is adjusted to have a fiber basis weight of 15 g/m$^2$.

A mixture of a fiber C coated with hydrophilic and lipophilic agents having a core-in-sheath structure of biased core type of high-density polyethylene and polyethylene terephthalate, an average fineness of 5.6 dtex, an average fiber length of 51 mm and 1% by weight of titanic oxide blended in relative to the weight of the core, and a fiber D of rayon having an average fineness of 3.3 dtex and an average fiber length of 45 mm is used as an absorbent body. The mixing ratio of the fiber C and the fiber D is 50:50 and the fiber basis weight is 100 g/m$^2$.

<Manufacture Condition>

A plurality of ejection holes 913 having a diameter of 1.0 mm are formed at a pitch of 6.0 mm. The shape of the ejection holes 913 is perfect circle, and the cross-sectional shape of the ejections holes 913 is circular. The width of the ejection unit 910 is 500 mm. Hot air is ejected at a temperature of 105° C. and an air volume of 1,200 L/minute.

An original fabric with the above fiber structure is then opened by means of a card apparatus at a speed of 20 m/minute to form multilayer fiber webs, and the multilayer fiber webs are cut to give each multilayer fiber web a width of 450 mm. The fiber webs are then placed and conveyed on a breathable net of 20 mesh being conveyed at a speed of 3 m/minute in a specified direction. The above hot air is ejected to the first side of the multilayer fiber webs from the ejection unit 910 described above while hot air is being suctioned from beneath the breathable net in a volume less than the hot air ejected. After irregularities (groove portions and raised ridge portions) are formed as above, the fiber webs are conveyed on the breathable net through inside an oven set at a temperature of 125° C. and a hot air volume of 10 Hz for approximately 30 seconds.

<Result>

Raised ridge portions: 131 g/m$^2$ fiber basis weight, 3.4 mm thickness (2.3 mm thickness at the top), 0.06 g/cm$^3$ fiber density, 4.6 mm width per raised ridge portion, 5.9 mm pitch Absorbent body in the raised ridge portions: 2.9 mm thickness (1.3 mm thickness at the top)

Groove portions: 58 g/m$^2$ fiber basis weight, 1.7 mm thickness, 0.03 g/cm$^3$ fiber density, 1.2 mm width per groove portion, 5.8 mm pitch Shape: The reverse side of the groove portions is positioned as the most reverse side of the absorbent body, and the shape of the reverse side of the raised ridge portions are raised upward and disposed in the position not forming the most reverse side of the absorbent body. The raised ridge portions are formed in dome shape, and the raised ridge portions and the groove portions are formed continuously so as to be extended along the length direction and formed alternately in relation to the width direction. The outermost surfaces of the raised ridge portions are formed in a way so that the strength of cross points between fibers differs partially, and the fiber density becomes the lowest.

3-2. Example 2

<Fiber Structure>

The fiber structure in Example 2 is the same as the fiber structure in Example 1.

<Manufacture Condition>

Hot air at a temperature of 105° C. and an air volume of 1,000 L/minute is ejected to the multilayer fiber webs in the above nozzle condition while almost equivalent or a slightly greater volume of air relative to the volume of hot air is suctioned from beneath the breathable net.

<Result>

The obtained absorbent body will be described below.

Raised ridge portions: 129 g/m$^2$ fiber basis weight, 2.5 mm thickness, 0.05 g/cm$^3$ fiber density, 4.7 mm width per raised ridge portion, 6.1 mm pitch Absorbent body in the raised ridge portions: 2.9 mm thickness Groove portions: 33 g/m fiber basis weight, 1.8 mm thickness, 0.02 g/cm$^3$ fiber density, 1.4 mm width per groove portion, 6.1 mm pitch Shape: The reverse side of the raised ridge portions are formed flat.

3-3. Example 3

<Fiber Structure>

A fiber layer made with 100% fiber coated with hydrophilic and lipophilic agents and formed by card method to have a core-in-sheath structure of high-density polyethylene and polyethylene terephthalate, an average fineness of 3.3 dtex, an average fiber length of 51 mm and 1% by weight of titanic oxide blended in the core, 2% by weight of titanic oxide blended in the sheath relative to each weight of core and sheath, and a fiber basis weight of 15 g/m² is used as a first fiber layer.

An absorbent body made with 100% crushed pulp with a fiber basis weight of 100 g/m² is used.

A fiber layer can be exemplified as containing a fiber C coated with hydrophilic and lipophilic agents having a core-in-sheath structure of biased core type of high-density polyethylene and polyethylene terephthalate, an average fineness of 5.6 dtex, an average fiber length of 51 mm, 1% by weight of titanic oxide blended relative to the weight of the core, and a fiber D of rayon having an average fineness of 3.3 dtex and an average fiber length of 45 mm. The mixing ratio of the fibers C and D in the fiber layer is 50:50, and the fiber layer is layered and formed by card method so as to have a fiber basis weight of 20 g/m².

<Manufacture Condition>

The manufacture condition is as similar to the one in Example 1.

<Result>

The obtained absorbent body will be described as follow.
Raised ridge portions: 162 g/m² fiber basis weight, 2.9 mm thickness, 0.06 g/cm³ fiber density, 4.7 mm width per raised ridge portion, 6.1 mm pitch
First fiber layer, absorbent body and second fiber layer in the groove portions: The first fiber layer has a thickness of 1.0 mm, the absorbent body has a thickness of 1.3 mm and the second fiber layer has a thickness of 0.6 mm.
Groove portions: 88 g/m² fiber basis weight, 1.8 mm thickness, 0.05 g/cm³ fiber density, 1.4 mm width per groove portion, 6.1 mm pitch

3-4. Example 4

<Fiber Structure>

The fiber structure is as similar to the one in Example 1.

<Manufacture Condition>

The manufacture condition of Example 4 is similar to the one in Example 1 except for using a support member described below instead of using a breathable net.

<Support Member>

A plate-like support member 230 in which holes 233 of 2 mm length×70 mm width are formed at intervals of 3 mm as shown in FIG. 24 is used. The plate-like support member 230 has a thickness of 0.5 mm and made of stainless steel.

<Manufacture Condition>

The manufacture condition is as similar to the one in Example 1.

<Result>

The obtained absorbent body will be described below.
Raised ridge portions: 155 g/m² fiber basis weight, 2.8 mm thickness, 0.06 g/cm³ fiber density, 4.7 mm width per raised ridge portion, 6.5 mm pitch
Absorbent body in raised ridge portions: 1.5 mm thickness
Groove portions: 77 g/m fiber basis weight, 1.2 mm thickness, 0.06 g/cm³ fiber density, 1.8 mm width per groove portion, 6.5 mm pitch
Slightly raised portion in the groove portions: 93 g/m² fiber basis weight, 1.9 mm thickness, 0.05 g/cm³ fiber density, 1.8 mm width per slightly raised portion, 1.5 mm length per slightly raised portion, 6.5 mm pitch in the cross direction, 5.0 mm pitch in the machine direction
Slightly depressed portion (opening) in the groove portions: oblong openings with round corners of 0 g/m² fiber basis weight, 0 mm thickness, 0 g/cm³ fiber density, 1.8 mm width per slightly depressed portion, 3.2 mm length per slightly depressed portion, 6.5 mm pitch in the cross direction, 5.0 mm pitch in the machine direction, 4.2 mm² opening area per slightly depressed portion
Shape: Slightly raised portions and slightly depressed portions (openings) are formed in the groove portions 1.

4. Examples of Application

For example, the absorbent body of the present invention can be used for absorbent articles such as sanitary napkins, panty liners and diapers. The absorbent body can be used as an absorbent body, or a surface sheet as well as an absorbent body of the above absorbent articles. In this case, the raised ridge portions may be facing the side which comes in contact with the skin or reverse; however, by making the raised ridge portions facing the side which comes in contact with the skin, the contact area with the skin is reduced making it unlikely for the users to feel wet from the body fluid. The absorbent body may also be used for various purposes such as wipers for removing dusts or dirt attached to the floor or body, wet tissues or wet wipers soaked in medicinal agents in advance, masks and breast milk pads, etc.

An exemplary absorbent article of the present invention in which raised ridge portions of an absorbent body, which contains absorbent fibers and irregularities on the first side wherein a fiber basis weight of the base of groove portions is relatively low and most of the fibers in the groove portions are oriented in the width direction, are disposed on the surface sheet side will be described below.

The areas which make up the base of the groove portions have relatively low fiber basis weight because fibers are displaced during forming of the groove portions 1. In addition, side portions 8 of the raised ridge portions 2 contain more fibers oriented in the longitudinal direction (length direction or machine direction) because side portions 8 are formed mostly of displaced fibers. This prevents dispersing of liquid in the width direction (cross direction) as well as induction of leakage thereby improving absorption efficiency of liquid by the absorbent body because the liquid dripped or migrated to the side portions 8 are guided in the length direction. Furthermore, the absorbent article can be easily deformed at the groove portions thus exhibiting high compatibility with the body making it unlikely for users to feel a foreign body sensation. In addition, side portions 8 of the raised ridge portions 2 have a high rigidity because fibers are closely packed. Furthermore, because the center portions 9 of the raised ridge portions 2 contain a lot of fibers oriented in the thickness direction, the raised ridge portions 2 are not easily crushed easily even with an additional weight in the thickness direction. And if the raised ridge portions are crushed by additional weight, they resume their original height easily because of their high ability to recover from compression. This makes liquid once absorbed unlikely to reverse its course and reversed liquid is unlikely to be reattached to the skin.

5. Structure Material

5-1. Fiber Aggregate

The fiber aggregates (fiber webs) formed into approximate sheet-like form contain fibers with flexibility which make up the fiber aggregates. Stated differently, they are fiber aggregates in which fibers are free from each other. Stated differently, they are fiber aggregates with fibers in which at least part of the fibers are free from each other. Moreover, at least a part of fibers which make up the multilayer fiber aggregates can change their relative positions. For example, the fiber aggregates may be formed by blowing out mixed fibers in which multiple fibers are mixed to form fiber layers of predetermined thickness. In addition, each of the different fibers is blown out for multiple times to form fiber layers, for example.

Examples of the fiber aggregates of the present invention include fiber webs formed by card method or fiber webs with heat sealed fibers prior to solidification. Moreover, examples also include webs formed by air-laid method, or fiber webs with heat sealed fibers prior to solidification. In addition, fiber webs embossed by point bonding method with heat sealed fibers prior to solidification, fiber aggregates formed by spun-bond method prior to embossing, or embossed fiber aggregates with heat sealed fibers prior to solidification may be included in examples. Furthermore, examples also include fiber webs formed by needle punching and half confounded, fiber webs formed by spunlace method and half confounded, fiber aggregates formed by melt blown method with heat sealed fibers prior to solidification, and fiber aggregates formed by solvent welding with fibers prior to solidification by solvents. Or these fiber aggregates may be layered to form a multilayer fiber aggregates.

The fiber aggregates for absorbent body are preferably manufactured by air-laid method when fiber aggregates are formed of fibers with a short fiber length or formed mostly of fibers with a short fiber length. Moreover, when fiber aggregates are formed of fibers with a long fiber length or formed mostly of fibers with a long fiber length, the fiber aggregates for absorbent body are preferably manufactured by card method.

The favorable fiber webs in which fibers are easily rearranged by air (gaseous matter) flow include webs formed only by confounding with fibers of high flexibility prior to heat sealing. In addition, it is preferable to use through-air method in which thermoplastic fibers contained in fiber aggregates are heat sealed by heating by means of a specified heating apparatus, etc. in order to form absorbent body after forming groove (irregular) portions, etc. by multiple air (gaseous matter) flow, which will be described below, while maintaining shapes thereof.

5-2. Fiber

The absorbent body and the absorbent article of the present invention at least contain absorbent fibers. The absorbent fibers are fibers equipped with a water-absorbing property and fibers provided with a water-absorbing property. Examples of fibers equipped with a water-absorbing property include cellulose fibers. Examples of cellulose fibers include semisynthetic cellulose such as crushed pulp or triacetate. These may be used alone or in combination.

Examples of fibers provided with a water-absorbing property include thermoplastic resins such as low-density polyethylene or polyamide. Moreover, hydrophilic agent may be kneaded into or applied, or hydrophilic property may be provided by corona or plasma treatment. Examples of the above fibers include fibers using various resins independently and composite fibers formed by structurally composing multiple resins.

Examples of composite fibers include a core-in-sheath type in which a melting point of core component is higher than that of sheath component, a biased core type of core-in-sheath structure and a side-by-side type in which left and right components have different melting points. Moreover, hollow type, flat, different types such as Y or C, three-dimensional crimped fibers by potential crimping or actual crimping, and divided fibers, etc. divided by physical load such as water flow, heat or embossing may also be used.

When fibers provided with a water-absorbing property or fibers equipped with a water-absorbing property are used for absorbent body, fineness is preferably in the range of 2.2 dtex to 8.8 dtex in consideration of liquid intrusion or liquid holding ability, and it is preferably in the range of 1.1 dtex to 8.8 dtex in consideration of liquid intrusion or texture when the fibers come in direct contact with the skin as the first fiber layers.

In addition, inorganic fillers such as titanic oxide, barium sulfate and calcium carbonate may be contained in the absorbent body for improved lightening. In the case of composite fibers of core-in-sheath type, inorganic fillers may be contained only in the core or both in core and sheath.

Furthermore, predetermined crimped fibers by actual crimping or potential crimping may be combined to form a 3-dimensional crimped shape. Examples of 3-dimensional crimped shape include spiral shape, zigzag shape and Ω-like shape, and the fibers are partially oriented in the thickness direction even though most fibers are oriented in a flat surface direction. This makes buckling strength of the fiber itself to work in the thickness direction and the thickness is likely to be maintained without being crushed by additional external pressure. Furthermore, having spiral shape makes it easier to resume its original thickness after being freed from external pressure even if thickness of the nonwoven fabric is slightly decreased due to excessive external pressure because spiral shape is likely to resume its original shape after being freed from external pressure.

The fiber formed by actual crimping is a general term for fibers formed by mechanical crimping, biased core types of core-in-sheath structure and side-by-side types which have been crimped in advance. The fibers formed by potential crimping are the fibers crimped by heat.

In mechanical crimping, continuous and straight fibers after forming are controlled by the difference in circumferential velocity of the speed in machine direction, heat or pressure. As the number of crimping per unit length of fibers increases, buckling strength under external pressure is increased. For example, the number of crimping per unit length of fibers is preferably in the range of 10 per inch to 35 per inch and more preferably in the range of 15 per inch to 30 per inch.

Examples of fibers formed by heat contraction include fibers made of two or more resins of different melting points. These fibers are crimped three dimensionally by the change in heat contraction percentage caused by heat. Examples of resin structure in the fibers formed by heat contraction include a biased core type of core-in-sheath structure in which a core is displaced from a center of cross section and a side-by-side type in which melting points of resins which make up a half of cross section and of resins which make up the other half thereof differ from each other. The heat contraction percentages of these fibers are preferably in the range of 5% to 90% and more preferably in the range of 10% to 80%, for example.

The method for measuring heat contraction percentage is as follows. (1) A fiber web of 200 gsm (g/m$^2$) containing 100% of fiber is formed for measurement, (2) the fiber web is cut in a dimension of 250 mm×250 mm to prepare a sample, (3) the sample is left unattended in an oven at 145° C. (418.15K) for 5 minutes, (4) the length of the sample after heat contraction is measured, and (5) a heat contraction percentage is then calculated from the difference in lengths before and after heat contraction.

As mentioned above, fibers may be rearranged easily by air flow in a web formed only by confounding with fibers of high flexibility prior to heat sealing, and when an absorbent body is formed after forming groove (irregular) portions, etc. by multiple air flows while keeping the shapes thereof, through-air method in which thermoplastic fibers are heat sealed by heat is preferable. The fibers suitable for this method are fibers of core-in-sheath structure or side-by-side structure for heat sealing the cross points of fibers, and it is preferable for the fibers of core-in-sheath structure in which sheaths are likely to be heat sealed steadily to be contained. In particular, using composite fibers of core-in-sheath structure made of polyethylene terephthalate and polyethylene or polypropylene and polyethylene is preferable. These fibers may be used alone or in combination. The length of fibers is preferably 20 mm to 100 mm and more preferably 35 mm to 65 mm.

5-3. Absorbent Polymer

Examples of absorbent polymer blended in fiber aggregates or contained in groove portions, etc. include polymer absorbent body of starch, carboxymethyl cellulose, polyacrylic acid and poval. Among them, sodium polyacrylate is preferable.

5-4. Fluid Consisting Mainly of Gaseous Matter

Examples of the fluid consisting mainly of gaseous matter in the present invention include gaseous matters with temperatures adjusted to a room temperature or a predefined temperature or aerosols with gaseous matters containing particles of solid matter or liquid.

Examples of gaseous matters include air and nitrogen. In addition, gaseous matters contain vapor of liquids such as water vapor.

Aerosols are gaseous matters in which liquids or solid matters are dispersed, and examples are as follows. Examples include gaseous matters in which inks for coloring, softeners such as silicon for improving flexibility, hydrophilic or water-repellent activators for preventing charging or controlling moistness, inorganic fillers such as titanic oxide and barium sulfate for increasing the energy of fluid, powder bonds such as polyethylene for increasing the energy of fluid as well as improving ability to maintain irregularities during heat treatment, antihistamines such as diphenhydramine hydrochloride and isopropyl methylphenol for antiitching, moisturizing agents or disinfection agents are dispersed. The solid matter includes gelatinous matters.

Temperatures of the fluid consisting mainly of gaseous matter can be adjusted accordingly. Temperatures are adjusted according to characteristic of the fibers which make up the fiber aggregates, fiber orientation, density or fiber basis weight of the absorbent body being manufactured or the shapes of predefined groove portions and openings.

It is preferable for the temperature of the fluid consisting mainly of gaseous matter to be high in some measure because it improves flexibility of the fibers which make up the fiber aggregates for moving the fibers which make up the fiber aggregates favorably. Moreover, when the thermoplastic fibers are contained in the fiber aggregates, the temperature of the fluid consisting mainly of gaseous matter is set at a temperature at which the thermoplastic fibers can be softened in order to soften or melt as well as to resolidify the thermoplastic fibers placed in the area where the fluid consisting mainly of gaseous matter is ejected.

By setting the temperature as above, fiber orientation, density or fiber basis weight of the absorbent body being manufactured or the shapes of predefined groove portions and openings are maintained by ejecting the fluid consisting mainly of gaseous matter, for example. In addition, strength by which the fiber aggregates (absorbent body) are protected from dispersing during moving of the fiber aggregates by means of a predetermined conveying unit is provided.

Flow volume of the fluid consisting mainly of gaseous matter can be adjusted according to fiber orientation, density or fiber basis weight of the absorbent body being manufactured or the shapes of predefined groove portions and openings. Specific examples of fiber aggregates in which fibers are freely movable include fiber web 100 formed by blending fibers of core-in-sheath structure with sheath made of high-density polyethylene and core made of polyethylene terephthalate, having a fiber length of 20 mm to 100 mm or preferably 35 mm to 65 mm and a fineness of 1.1 dtex to 8.8 dtex or preferably 2.2 dtex to 5.6 dtex, and rayon fibers made of rayon selected from the fibers having the same fiber length and fineness. If fiber spreading is performed by card method, fibers with a fiber length of 20 mm to 100 mm or preferably 35 mm to 65 mm are used, and if it is performed by air-laid method, fibers with a fiber length of 1 mm to 50 mm or preferably 3 mm to 20 mm are used to form a fiber web 100 adjusted to be in the range of 10 g/m$^2$ to 1,000 g/m$^2$ or preferably 15 g/m$^2$ to 100 g/m$^2$. The exemplary ejection condition of the fluid consisting mainly of gaseous matter is as follows. Hot air at a temperature of 15° C. to 300° C. (288.15 K to 573.15K) or preferably 100° C. to 200° C. (373.15K to 473.15K) is ejected to the fiber web 100 with a volume of 3 L/minute per hole to 50 L/minute per hole or preferably 5 L/minute per hole to 20 L/minute per hole from an ejection unit 910 in which a plurality of ejection holes 913, which are perfect circle, ellipse or rectangle having a diameter of 0.1 mm to 30 mm or preferably 0.5 mm to 5 mm, a pitch of 0.5 mm to 30 mm or preferably 0.1 mm to 10 mm are formed. For example, it is preferable for the fiber aggregate of the present invention to have fibers which can change positions or orientations thereof when the fluid consisting mainly of gaseous matter is ejected on the above condition. The multilayer nonwoven fabrics described above can be formed, for example, by using the above fibers under above manufacturing condition. The dimensions and fiber basis weights of the areas which make up the base of the groove portions 1 and the raised ridge portions 2 are as follows. The thickness of the groove portions 1 is in the range of 0.05 mm to 10 mm or preferably 0.1 mm to 5 mm, width is in the range of 0.1 mm to 30 mm or preferably 0.5 mm to 5 mm, fiber basis weight is in the range of 2 g/m$^2$ to 900 g/m$^2$ or preferably 10 g/m$^2$ to 90 g/m$^2$. The thickness of the raised ridge portions 2 is in the range of 0.1 mm to 15 mm or preferably 0.5 mm to 10 mm, width is in the range of 0.5 mm to 30 mm or preferably 1.0 mm to 10 mm, fiber basis weight is in the range of 5 g/m$^2$ to 1,000 g/m$^2$ or preferably 10 g/m$^2$ to 100 g/m$^2$. The absorbent body can be formed in the range of approximately above numerical values; however, it is not limited to the above range.

5-5. Manufacturing Apparatus-Related 5-5-1. Breathable Support Member

The breathable support member is a support member through which the fluid consisting mainly of gaseous matter ejected from the ejection unit 910 and ventilated through the fiber web 100 can be ventilated to a side opposite of the side on which the fiber web 100 is placed.

For example, the net-like support member 210 can be exemplified as a support member through which the fluid consisting mainly of gaseous matter can be ventilated without changing flow thereof. The net-like support member 210 can be manufactured, for example, by a fine net-like member formed by weaving slender wires. In addition, the net-like support member 210 is a breathable support member in which a net-like member, a first ventilation unit described later is disposed entirely.

The breathable support member may contain breathable portions where the fluid consisting mainly of gaseous matter ejected to the upper side of the fiber web 100 can be ventilated downward to a side opposite of the side of the breathable support member on which the fiber web 100 is placed, and impervious portions where the fluid consisting mainly of gaseous matter ejected to the upper side of the fiber web 100 cannot be ventilated downward of the breathable support member and fibers 101 which make up the fiber web 100 cannot be displaced to the opposite side of the breathable support member.

Examples of such breathable support member include support members in which impervious members are disposed on a predefined net-like member by prescribed patterning, or support members in which a plurality of predefined holes are formed in an impervious plate-like member.

Examples of the support member in which impervious portions are disposed on a predefined net-like member by prescribed patterning include a support member 220 in which slender members 225 as impervious members are disposed in parallel with each other at regular intervals on the first side of the net-like support member 210. Meanwhile, above support members in which shapes or arrangements of the slender members 225 as impervious members are changed accordingly may be exemplified as other embodiments. Impervious portions can be formed by disposing slender members 225 on the first side of the net-like support member 210 or filling net-like portions as the breathable portions by soldering or with resins, etc., for example.

Examples of impervious plate-like members in which a plurality of predefined holes are formed include a plate-like support member 230 in which a plurality of oval holes 233 as breathable portions are formed. The plate-like support members in which shape, size and arrangement of the holes 233 are adjusted accordingly may be exemplified as other embodiments. Stated differently, plate-like support members in which shapes of the impervious plate 235 are adjusted accordingly may be exemplified as other embodiments.

The breathable portions in the breathable support member include a first breathable portion where fibers 101 which make up the fiber web 100 cannot actually be displaced to a side (downward) opposite of the side of the breathable support member on which the fiber web 100 is placed, and a second breathable portion where the fibers which make up the fiber aggregates can be displaced to an opposite side of the breathable support member.

Examples of the first breathable portion include a net-like area in the net-like support member 210. Moreover, examples of the second breathable portion include holes 233 in the plate-like support member 230.

The net-like support member 210 can be exemplified as a breathable support member containing a first breathable portion. The support member 220 can be exemplified as a breathable support member containing an impervious portion and a second breathable portion. The plate-like support member 230 can be exemplified as a breathable support member containing an impervious portion and a first breathable portion.

Other examples include a breathable support member consist of a first breathable portion and a second breathable portion, and a breathable support member equipped with an impervious support member and the first and second breathable portions. Examples of breathable support members containing first and second breathable portions include breathable support members in which a plurality of openings are formed in the net-like support member 210. Moreover, examples of breathable support members containing an impervious support member and the first and second breathable portions include breathable support members in which a plurality of openings are formed in a net-like area of the support member 220.

Examples of the breathable support member 200 include support members with the supporting side of the fiber web 100 being almost flat or curved and the flat surface or curved surface thereof is almost flat. Examples of almost flat or curved shape include plate-like or cylindrical shape. And being almost flat means that irregularities are not formed on the surface of the support member on which the fiber web 100 is placed, for example. Specific examples of the support member include the net-like support member 210 with flat net.

Examples of the breathable support member include plate-like support members or cylindrical support members. Specifically, examples include the above-mentioned net-like support member 210, the support member 220, the plate-like support member 230 and breathable support drums.

The breathable support member can be placed onto the absorbent body manufacturing apparatus 90 as detachable. This enables to place a suitable breathable support member according to fiber orientation, density or fiber basis weight of desired absorbent body, or predefined groove portions or openings. Stated differently, the breathable support member placed onto the absorbent body manufacturing apparatus 90 is replaceable with other breathable support members selected from different breathable support members. The present invention includes an absorbent body manufacturing system equipped with the absorbent body manufacturing apparatus 90 and different breathable support members.

The net-like portion of the net-like support member 210 or the support member 220 will be explained below. Examples of the breathable net-like portion include a net made of resin threads such as polyester, polyphenylene sulfide, nylon, conductive monofilament, etc. or metal threads such as stainless steel, copper and aluminum that are woven by flat weaving, twill weaving, sateen weaving, double weaving and spiral weaving, etc.

The ventilation rate of the breathable net can be changed partially by partially changing the weaving method, thread thickness or thread shape, for example. Specifically, it may be exemplified by spiral-woven breathable mesh of polyester and spiral-woven breathable mesh woven with flat and circular threads of stainless steel.

In addition, silicon resins, etc. may be patterned and applied to a breathable net, or impervious materials may be joined partially instead of slender members 225 disposed on the first side of the support member 220. For example, silicon resins may be applied to a breathable net of 20 mesh flatly woven with polyester so as to be extended in the width direction and alternate in the line direction. The areas coated with silicon resins or connected with impervious materials become impervious portion, and other areas become the first breathable portion. Moreover, the surface of the impervious portion is preferably flat for improving smoothness of the surface.

Examples of the plate-like support member 230 include sleeves made of metals such as stainless steel, copper and aluminum. For example, sleeves may be of the above metal plate from which predefined pattern is partially cut out. The area from which the metal has been cut out becomes a second breathable portion, and the area from which the metal has not been cut out becomes an impervious portion. Moreover, the surface of the impervious portion is preferably flat for improving smoothness of the surface as described above.

Examples of sleeves include stainless steel sleeves having a thickness of 0.3 mm on which lateral rectangle holes with rounded corners having a length of 3 mm and a width of 40 mm formed by cutting metal out are disposed in lattice-like arrangement at intervals of 2 mm in the line flow direction (moving direction) and at intervals of 3 mm in the width direction.

Examples also include sleeves on which holes are disposed in a zigzag arrangement. For example, stainless steel sleeves of 0.3 mm thickness on which circular holes having a diameter of 4 mm formed by cutting metal out are disposed at a pitch of 12 mm in the line flow direction (moving direction) and at a pitch of 6 mm in the width direction in a zigzag arrangement. As described above, cut out patterns (formed holes) and arrangements may be decided accordingly.

Furthermore, examples also include a breathable support member with predefined roughness. For example, the breathable support member having areas where the fluid consisting mainly of gaseous matter is not ejected directly and alternate roughness (corrugated shape, for example) are formed in the line flow direction (moving direction) may be included. By using the breathable support member as described above, it is possible to obtain an absorbent body in which fiber orientation, density and fiber basis weight are adjusted, and predetermined groove portions or openings as well as alternate roughness (corrugated shape, for example) are formed entirely.

The fiber orientation, density or fiber basis weight of the fibers 101 in the fiber web 100 or shape and size of the formed groove portions or openings become completely different depending on the structure of the breathable support member even if a gaseous matter is ejected from the ejection unit 910 under similar condition. Stated differently, absorbent body adjusted to have desired fiber orientation, density or fiber basis weight, or absorbent body in which predetermined groove portions or openings are formed can be obtained by selecting a suitable breathable support member.

The absorbent body manufacturing apparatus 90 of the present invention can be characterized by being able to manufacture an absorbent body in which fiber orientation, density and fiber basis weight are adjusted and predetermined groove portions or openings are formed by ejecting a fluid consisting mainly of gaseous matter continuously to the fiber web 100 as a fiber aggregate from an ejection unit.

5-5-2. Conveying Unit

The conveying unit conveys the fiber web 100 as a fiber aggregate in a specified direction while it is being supported by the above breathable support member from the first side. Specifically, the fiber web 100 to which the fluid consisting mainly of gaseous matter is ejected is conveyed in the specified direction F. Examples of conveying unit include a conveyer 930. The conveyer 930 contains a horizontally long, ring-shaped breathable belt unit 939 on which the breathable support member is disposed, and rotating units 931 and 933, which rotates the horizontally long, ring-shaped breathable belt unit 939 in a specified direction and disposed inside of the horizontally long, ring-shaped breathable belt unit 939 that is on both sides in the length direction. If the breathable support member is the net-like support member 210 or support member 220, the above breathable belt unit 939 may not be disposed. When a support member in which large holes are formed as in the plate-like support member 230 is used as the breathable support member, for example, it is preferable to dispose the breathable belt unit 939 for preventing fibers which make up the fiber web 100 from falling from the holes and migrating into the apparatus used in the process. Examples of the breathable belt unit 939 include net-like belt units.

The conveyer 930 conveys the breathable support member in a specified direction F while the breathable support member is supporting the fiber web 100 from beneath as described above. Specifically, the fiber web 100 is moved so as to pass through beneath the ejection unit 910. Furthermore, the fiber web 100 is moved so as to pass through inside of the heater unit 950 in which both sides are opened as a heating unit.

Examples of conveying unit include a combination of multiple conveyers. By combining multiple conveyers, the speed moving toward the ejection unit 910 and away from the ejection unit 910 can be adjusted accordingly to thereby adjust fiber orientation, density or fiber basis weight, or shapes of the groove portions or openings in the absorbent body 115.

The absorbent body 115 manufactured by heat by means of the heater unit 950 is conveyed to a cutting step in which the absorbent body 115 is cut in a specified shape or to a rewinding step by the conveyers 930 and 940 running in a specified direction F. The conveyer 940 may contain a belt unit 949 and a rotating unit 941 as similar to the conveyer 930.

5-5-3. Ejection Unit

The ejection unit contains an air supplying unit (not shown) and an ejection unit 910. The air supplying unit not shown in figures is connected to the ejection unit 910 through an air supplying tube 920. The air supplying tube 920 is connected to an upper side of the ejection unit 910 as breathable. A plurality of ejection holes 913 are formed at predetermined intervals in the ejection unit 910.

The gaseous matter supplied from the air supplying unit (not shown) to the ejection unit 910 through the air supplying tube 920 is ejected from the ejection holes 913 formed in the ejection unit 910. The gaseous matter ejected from the ejection holes 913 is ejected continuously to an upper side of the fiber web 100 supported by the breathable support member from beneath. Specifically, the gaseous matter ejected from the ejection holes 913 is ejected continuously to the upper side of the fiber web 100 being conveyed in the specified direction F by means of the conveyer 930.

An air suctioning unit 915 disposed beneath the breathable support member, which is beneath the ejection unit 910, suctions gaseous matter ejected from the ejection unit 910 and ventilated through the breathable support member. It is also possible to position the air suctioning unit 915 to make the fiber web 100 stick to the breathable support member by suction force of the air suctioning unit 915. Furthermore, the fiber web 100 can be conveyed inside of the heater unit 950 by suctioning while shapes of the groove portions (irregularities), etc. formed by air flow are being well maintained. In this case, the fiber web 100 is preferably conveyed to the heater unit 950 while being formed by air flow and suctioned.

For example, an absorbent body 110 in which groove portions 1 are formed on upper side of the fiber web 100 at predetermined intervals by the fluid consisting mainly of gaseous matter ejected from the ejection holes 913 formed at regular intervals in the width direction of the fiber web 100 is manufactured.

Examples of the ejection unit 910 include an ejection unit in which ejection holes 913 with a diameter of 0.1 mm to 30 mm or preferably 0.3 mm to 10 mm formed at a pitch between ejection holes 913 of 0.5 mm to 20 mm or preferably 3 mm to 10 mm are formed.

Shapes of the ejection holes 913 are not limited and may be exemplified as being substantially circle, ellipse, square or rectangle. The cross sectional shape of the ejection holes 913 is not limited and may be exemplified as being cylindrical, trapezoidal and inverted trapezoidal. The shapes of the ejection holes 913 are preferably substantially circle and cross sectional shapes are preferably cylindrical considering the fact that air can be ejected to the fiber web 100 more effectively.

The ejection holes 913 can be designed according to the desired fiber orientation, density or fiber basis weight, or predetermined groove portions or openings of the absorbent body. Moreover, diameter and shape of each of the ejection holes 913 may be different, and the ejection holes 913 may be formed so as to form a plurality of lines in the ejection unit 910.

Temperatures of the fluid consisting mainly of gaseous matter ejected from each of the ejection holes 913 may be a room temperature as described above, however, in order to improve formability of the groove portions (irregularities) or openings, for example, the temperature may be adjusted to at least more than softening points of thermoplastic fibers which make up the fiber aggregate, and preferably at a temperature greater than the softening points and at melting points +50° C. or less. If the fibers are softened, the shapes of the fibers reoriented are easily maintained by air flow, etc. because repulsive force of the fibers themselves is lowered, and if the temperature is further increased, shapes of the groove portions (irregularities), etc. are more easily maintained because heat sealing between fibers begins. This makes conveying of the fiber into the heater unit 950 while maintaining the shapes of the groove portions (irregularities) easy.

Moreover, the fiber web 100 can be conveyed into the heater unit 950 right after forming the groove portions (irregularities), etc. by air flow, etc. or during forming, or the fiber web 100 can be conveyed into the heater unit 950 after cooling by cool air, etc. right after forming the groove portions (irregularities), etc. by hot air (air flow at a specified temperature) while well maintaining the shapes of the groove portions (irregularities), etc. formed by air flow, etc.

As other elements for adjusting fiber orientation, density or fiber basis weight, or shape and size of formed groove portions or openings of the fibers 101 by moving the fibers 101 in the fiber web 100, flow rate or flow volume of the gaseous matter ejected from the ejection unit 910 may be exemplified other than the structures of the above breathable support member. The flow speed or flow volume of ejected gaseous matter can be adjusted, for example, by volume of air supplied from the air supplying unit (not shown), or numbers or diameters of the ejection holes 913 formed in the ejection unit 910.

Intervals between groove portions 1 in formed irregularities or heights of the raised ridge portions in formed irregularities can be adjusted accordingly by making the ejection unit 910 enable to change directions of the fluid consisting mainly of gaseous matter. In addition, shapes of the groove portions, etc. can be adjusted to have corrugated, zigzag or other shapes accordingly by making the above fluid direction automatically changeable. Moreover, shapes or formed patterns of the groove portions or openings can be adjusted accordingly by adjusting volume of ejected fluid consisting mainly of gaseous matter or ejection time. The ejected angle of the fluid consisting mainly of gaseous matter relative to the fiber web 100 may be perpendicular, or tilted at a specific angle in the line flow direction, which is the moving direction F of the fiber web 100, or tilted at a specific angle in the direction opposite of the line flow direction.

5-5-4. Heating Unit

The heater unit 950 as a heating unit has openings on both sides in relation to the specified direction F. By these openings, the fiber web 100 (multilayer nonwoven fabric 110) placed on the breathable support member being conveyed by the conveyer 930 is moved to a heated space formed within the heater unit 950 and conveyed outside after staying in the heated space for a predetermined time. When thermoplastic fibers are contained in the fibers 101 which make up the fiber web 100 (multilayer nonwoven fabric 110), a multilayer nonwoven fabric in which fibers are heat sealed in the heating unit 950, and sealed at cross points between fibers after being conveyed outside and cooled can be obtained.

Examples of method for bonding fibers 101 and 102 in the multilayer nonwoven fabric 110 in which fiber orientation, density or fiber basis weight are adjusted and/or one or more of predefined groove portions, openings or raised ridge portions are formed include bonding by needle punching, spunlace method and solvent welding, or heat bonding by point bonding method or through-air method. Of these, through-air method is preferable for bonding fibers while maintaining adjusted fiber orientation, density or fiber basis weight, or formed shape of predefined groove portions, openings or raised ridge portions. And heat treatment by through-air method by means of the heater unit 950 is preferable, for example.

While preferred embodiments of the present invention have been described and illustrated above, it is to be understood that they are exemplary of the invention and are not to be considered to be limiting. Additions, omissions, substitutions, and other modifications can be made thereto without departing from the spirit or scope of the present invention. Accordingly, the invention is not to be considered to be limited by the foregoing description and is only limited by the scope of the appended claims.

What is claimed is:

1. An absorbent body comprising:
a first absorbent body; and
a second absorbent body includes an absorbent polymer, wherein
each of the first and the second absorbent body includes:
  a plurality of low fiber basis weight regions; and
  a plurality of high fiber basis weight regions,
  wherein
  the low fiber basis weight regions, which are formed continuously along a first direction have a fiber basis weight that is less than an average fiber basis weight of the absorbent body,
  the high fiber basis weight regions, which are formed on both sides of the low fiber basis weight regions in a second direction perpendicular to the first direction along the low fiber basis weight regions, have a fiber basis weight that is greater than the average fiber basis weight of the absorbent body,
  a content of fibers oriented toward the first direction, in the fibers which make up each of the high fiber basis weight regions is greater than a content of fibers oriented toward the second direction in each said high fiber basis weight region, and
  a content of fibers oriented toward the second direction, in the fibers which make up each of the low fiber basis weight regions is greater than a content of fibers oriented toward the first direction in each said low fiber basis weight region,
the first absorbent body and the second absorbent body are layered in a thickness direction of the absorbent body,
the low fiber basis weight regions of the first absorbent body and the second absorbent body face each other in the thickness direction, and the high fiber basis weight regions of the first absorbent body and the second absorbent body face each other in the thickness direction.

2. The absorbent body according to claim 1, wherein
the high fiber basis weight regions have raised ridge portions raised in a thickness direction of the absorbent body, with a thickness, which is a length in the thickness direction, being greater than an average thickness of the absorbent body, and
the low fiber basis weight regions have groove portions depressed in the thickness direction with a thickness being less than the average thickness of the absorbent body.

3. The absorbent body according to claim 1, wherein the low fiber basis weight regions comprise at least one of a plurality of depressed portions and openings.

4. The absorbent body according to claim 2, wherein the high fiber basis weight regions further have side areas disposed on both sides of the low fiber basis weight regions, and
a thickness of each of the side areas in the thickness direction is less than that of each of the raised ridge portions.

5. The absorbent body according to claim 1, wherein the absorbent body further comprises an absorbent polymer.

6. The absorbent body according to claim 5, further comprising a first side and a second side opposite to the first side, wherein the low fiber basis weight regions and the high fiber basis weight regions are formed on the first side and the absorbent polymer is disposed on the second side.

7. The absorbent body according to claim 5, wherein the absorbent polymer is disposed in the low fiber basis weight regions.

8. An absorbent article, comprising:
a multilayer absorbent body comprising,
    a first fiber layer having a first side and a second side opposite to the first side;
    an absorbent body comprising absorbent fibers, wherein the absorbent body is layered and disposed on the first side of the first fiber layer; and
    a liquid-impermeable sheet,
wherein the absorbent body is located between the first fiber layer and the liquid-impermeable sheet,
wherein each of said first fiber layer and said absorbent body further including
    a plurality of groove portions formed along a first direction and depressed in a thickness direction of the multilayer absorbent body from the second side toward the first side, and
    a plurality of raised ridge portions each formed adjacent to one of the groove portions in a second direction perpendicular to the first direction and said raised, ridge portions being raised in the thickness direction from the first side toward the second side,
wherein a fiber basis weight of said raised ridge portions is greater than that of the groove portions and wherein the absorbent article further comprises a second fiber layer disposed between the absorbent body and the liquid-impermeable sheet.

9. The absorbent article according to claim 8, wherein
a content of the fiber oriented toward the first direction, in the fibers which make up each of the raised ridge portions, is greater than a content of the fiber oriented toward the second direction in each said raised ridge portion, and
a content of the fiber oriented toward the second direction, in the fibers which make up each of the groove portions, is greater than a content of the fiber oriented toward the first direction in each said groove portion.

10. The absorbent article according to claim 8, wherein the groove portions include
at least one of a plurality of depressed portions and openings formed at predetermined intervals in the first direction, and
sidewall portions defining peripheral borders of each of the groove portions and covered by the first fiber layer.

11. The absorbent article according to claim 8, further comprising a second fiber layer, wherein said absorbent body is sandwiched between the first fiber layer and the second fiber layer.

12. The absorbent article according to claim 11, wherein
the first fiber layer and the second fiber layer are layered and formed by a card method, and
the absorbent body is formed by layering fibers of the absorbent body, on the first side of the first fiber layer by an air-laid method.

13. The absorbent article according to claim 8, wherein a content of the fiber oriented toward the first direction, in the fibers which make up each of the raised ridge portions, is greater than a content of the fiber oriented toward the second direction in each said raised ridge portion, and
a content of the fiber oriented toward the second direction, in the fibers which make up each of the groove portions, is greater than a content of the fiber oriented toward the first direction in each said groove portion.

14. The absorbent article according to claim 8, wherein a plurality of low amount of fiber regions including at least one of a plurality of depressed portions and openings is formed at predetermined intervals in each of the groove portions, and
at least part of the sidewall portions which make up peripheral borders of each of the plurality of low amount of fiber regions are covered by the fibers which make up the first fiber layer.

15. The absorbent body according to claim 5, wherein the absorbent polymer is filled in the low fiber basis weight regions.

16. The absorbent body according to claim 5, wherein the absorbent polymer is filled in the low fiber basis weight regions without being presented in the high fiber basis weight regions.

17. The absorbent body according to claim 1, wherein the absorbent polymer is filled in the low fiber basis weight regions of the second absorbent body.

* * * * *